United States Patent
Hori et al.

(10) Patent No.: US 9,618,845 B2
(45) Date of Patent: Apr. 11, 2017

(54) METHOD FOR FORMING RESIST PATTERN, RESIST PATTERN SPLITTING AGENT, SPLIT PATTERN IMPROVING AGENT, RESIST PATTERN SPLITTING MATERIAL, AND POSITIVE RESIST COMPOSITION FOR FORMING SPLIT PATTERN

(71) Applicant: TOKYO OHKA KOGYO CO., LTD., Kawasaki-shi (JP)

(72) Inventors: Yoichi Hori, Kawasaki (JP); Takayoshi Mori, Kawasaki (JP); Ryoji Watanabe, Kawasaki (JP); Rikita Tsunoda, Kawasaki (JP)

(73) Assignee: TOKYO OHKA KOGYO CO., LTD., Kawasaki-Shi (JP)

( * ) Notice: Subject to any disclaimer, the term of this patent is extended or adjusted under 35 U.S.C. 154(b) by 0 days.

(21) Appl. No.: 14/864,099

(22) Filed: Sep. 24, 2015

(65) Prior Publication Data
US 2016/0091790 A1 Mar. 31, 2016

(30) Foreign Application Priority Data

Sep. 26, 2014 (JP) .................. 2014-197463
Mar. 27, 2015 (JP) .................. 2015-066200
May 27, 2015 (JP) .................. 2015-107303

(51) Int. Cl.
*G03F 7/11* (2006.01)
*G03F 7/40* (2006.01)
(Continued)

(52) U.S. Cl.
CPC .............. *G03F 7/11* (2013.01); *C07C 321/28* (2013.01); *C07D 213/79* (2013.01);
(Continued)

(58) Field of Classification Search
CPC ... G03F 7/004; G03F 7/11; G03F 7/20; G03F 7/30; G03F 7/32; G03F 7/40;
(Continued)

(56) References Cited

U.S. PATENT DOCUMENTS

2009/0197204 A1  8/2009  Shiono et al.
2009/0317743 A1  12/2009  Shiono et al.
(Continued)

FOREIGN PATENT DOCUMENTS

JP   2006303504 A  * 11/2006
JP   A-2010-002870    1/2010
(Continued)

*Primary Examiner* — Amanda C Walke
(74) *Attorney, Agent, or Firm* — Knobbe Martens Olson & Bear LLP

(57) ABSTRACT

A method of forming a resist pattern, including: a step A in which a positive resist composition is applied to a substrate to form a positive resist film, the positive resist film is exposed and the positive resist film is subjected to an alkali development to form a first resist pattern; a step B in which a solution containing an acid or a thermoacid generator is applied to the substrate whereon the first resist pattern is formed, so as to cover the first resist pattern, to form a structure having the first resist pattern and a first layer covering the first resist pattern; a step C in which the structure is heated and the solubility of the first resist pattern in an organic solvent is changed under action of the acid or under action of acid generated from the thermoacid generator; and a step D in which the structure after heating is developed with the organic solvent to remove a region of the first resist pattern other than the region of the first resist pattern where the solubility in the organic solvent is changed, so as to form a second resist pattern.

14 Claims, 4 Drawing Sheets

(51) Int. Cl.

| | | |
|---|---|---|
| *G03F 7/004* | (2006.01) | |
| *C07C 321/28* | (2006.01) | |
| *G03F 7/20* | (2006.01) | |
| *G03F 7/32* | (2006.01) | |
| *C07D 295/155* | (2006.01) | |
| *G03F 7/30* | (2006.01) | |
| *C07D 295/26* | (2006.01) | |
| *C07D 213/79* | (2006.01) | |
| *G03F 7/039* | (2006.01) | |

(52) U.S. Cl.
CPC ....... *C07D 295/155* (2013.01); *C07D 295/26* (2013.01); *G03F 7/0045* (2013.01); *G03F 7/0046* (2013.01); *G03F 7/0397* (2013.01); *G03F 7/20* (2013.01); *G03F 7/30* (2013.01); *G03F 7/32* (2013.01); *G03F 7/325* (2013.01); *G03F 7/40* (2013.01); *G03F 7/405* (2013.01)

(58) Field of Classification Search
CPC .......... G03F 7/0048; G03F 7/38; G03F 7/325; C07D 295/26; C07D 295/155; C07D 213/79; C07C 321/28
USPC ...... 430/270.1, 271.1, 273.1, 322, 325, 329, 430/330, 331, 913; 560/1, 8, 14
See application file for complete search history.

(56) References Cited

U.S. PATENT DOCUMENTS

| | | | |
|---|---|---|---|
| 2010/0310985 A1 | 12/2010 | Mori et al. | |
| 2011/0117499 A1 | 5/2011 | Matsumiya et al. | |
| 2011/0129652 A1* | 6/2011 | Burns | G03F 7/40 428/195.1 |
| 2011/0183269 A1* | 7/2011 | Zhu | G03F 7/405 430/319 |
| 2012/0282548 A1* | 11/2012 | Enomoto | G03F 7/0045 430/284.1 |
| 2013/0059252 A1* | 3/2013 | Maruyama | G03F 7/091 430/296 |
| 2013/0171825 A1* | 7/2013 | Xu | H01L 21/0274 438/694 |
| 2013/0209941 A1 | 8/2013 | Motoike et al. | |
| 2014/0017617 A1* | 1/2014 | Arai | G03F 7/0045 430/325 |
| 2014/0186772 A1* | 7/2014 | Pohlers | G03F 7/405 430/311 |
| 2015/0253670 A1* | 9/2015 | Fukami | G03F 7/168 430/325 |
| 2016/0011513 A1* | 1/2016 | Kiridoshi | G03F 7/30 430/322 |
| 2016/0209749 A1* | 7/2016 | Yamamoto | G03F 7/40 430/311 |

FOREIGN PATENT DOCUMENTS

| | | |
|---|---|---|
| JP | A-2010-032994 | 2/2010 |
| JP | A-2010-277043 | 12/2010 |
| JP | A-2011-013569 | 1/2011 |
| JP | A-2011-128226 | 6/2011 |
| JP | A-2013-164509 | 8/2013 |

* cited by examiner

METHOD FOR FORMING RESIST PATTERN, RESIST PATTERN SPLITTING AGENT, SPLIT PATTERN IMPROVING AGENT, RESIST PATTERN SPLITTING MATERIAL, AND POSITIVE RESIST COMPOSITION FOR FORMING SPLIT PATTERN

FIELD OF THE INVENTION

The present invention relates to a method of forming a resist pattern, a resist pattern splitting agent, a split pattern improving agent, a resist pattern splitting material, and a positive resist composition for forming split pattern.

Priority is claimed on Japanese Patent Application No. 2014-197463, filed Sep. 26, 2014, Japanese Patent Application No. 2015-66200, filed Mar. 27, 2015, and Japanese Patent Application No. 2015-107303, filed May 27, 2015, the contents of which are incorporated herein by reference.

BACKGROUND OF THE INVENTION

In lithography techniques, for example, a resist film composed of a resist material is formed on a substrate, and the resist film is subjected to selective exposure of radial rays such as light or electron beam through a mask having a predetermined pattern, followed by development, thereby forming a resist pattern having a predetermined shape on the resist film.

A resist material in which the exposed portions become soluble in a developing solution is called a positive-type, and a resist material in which the exposed portions become insoluble in a developing solution is called a negative-type.

In recent years, in the production of semiconductor elements and liquid crystal display elements, advances in lithography techniques have led to rapid progress in the field of pattern miniaturization.

Typically, these miniaturization techniques involve shortening the wavelength (increasing the energy) of the exposure light source. Conventionally, ultraviolet radiation typified by g-line and i-line radiation has been used, but nowadays KrF excimer lasers and ArF excimer lasers are starting to be introduced in mass production of semiconductor elements. Furthermore, research is also being conducted into lithography techniques that use an exposure light source having a wavelength shorter (energy higher) than these excimer lasers, such as electron beam, extreme ultraviolet radiation (EUV), and X ray.

As a technique for providing a finer pattern, there is proposed a double patterning process for forming a resist pattern by performing patterning more than once. According to the double patterning process, for example, a first resist pattern is formed on a support by performing patterning using a first resist composition, then patterning is further performed on the support, on which the first resist pattern is formed, using a second resist composition, and thereby a resist pattern having higher resolution than the resist pattern formed by single patterning can be formed.

In JP-A-2013-164509, there is disclosed a method of forming a resist pattern, in which a first resist pattern is formed on a support, a $SiO_2$ film is formed on the surface whereon the first resist pattern has formed, etching is performed using the $SiO_2$ film as a sacrificial film, and then the first resist pattern is removed, thereby forming a second pattern of the $SiO_2$ film.

PRIOR ART

Patent Literature

[PTL 1] Japanese Unexamined Patent Application, First Publication No. 2013-164509

SUMMARY OF THE INVENTION

However, the above method is problematic in that multiple courses of exposure are required, and processing is complicated due to a large number of processes. Further, there is still room for improvement in a method of forming a fine pattern.

The present invention has been accomplished in consideration of the above-described problem, with an object of providing a method of forming a pattern, in which a fine pattern can be formed through a simple process.

According to a first aspect of the present invention, there is provided a method of forming a resist pattern including: a step A in which a positive resist composition is applied to a substrate to form a positive resist film, the positive resist film is exposed and the positive resist film is subjected to an alkali development to form a first resist pattern; a step B in which a solution containing an acid or a thermoacid generator is applied to the substrate whereon the first resist pattern is formed, so as to cover the first resist pattern, to form a structure having the first resist pattern and a first layer covering the first resist pattern; a step C in which the structure is heated and the solubility of the first resist pattern in an organic solvent is changed under action of the acid or under action of acid generated from the thermoacid generator; and a step D in which the structure after heating is developed with the organic solvent to remove a region of the first resist pattern other than the region of the first resist pattern where the solubility in the organic solvent is changed, so as to form a second resist pattern.

According to a second aspect of the present invention, there is provided a resist pattern splitting agent, which is used to cover a resist pattern and split the resist pattern, comprising at least: a solvent; and an acid or a thermoacid generator.

According to a third aspect of the present invention, there is provided a split pattern improving agent, which is used to further cover a resist pattern after covering the resist pattern using the resist pattern splitting agent according to the second aspect of the present invention, comprising at least: an organic solvent; and an acid diffusion control agent.

According to a fourth aspect of the present invention, there is provided a resist pattern splitting material, comprising: the resist pattern splitting agent according to the second aspect of the present invention; and a split pattern improving agent, which is used to further cover a resist pattern after covering the resist pattern using the resist pattern splitting agent, comprising at least: an organic solvent; and an acid diffusion control agent.

According to a fifth aspect of the present invention, there is provided a positive resist composition for forming a split pattern, which is used in the method of forming a resist pattern according to the first aspect of the present invention, and the positive resist composition generating acid upon exposure and exhibiting increased solubility in a developing solution under action of acid, wherein the positive resist composition comprises an acid diffusion control agent, and the acid diffusion control agent contains an acid having an acid dissociation constant (pKa) of 3.0 or more.

Effect of the Invention

According to the present invention, it is possible to provide a method of forming a pattern, by which a fine pattern can be formed through a simple process.

DETAILED DESCRIPTION OF THE INVENTION

Figure 1:
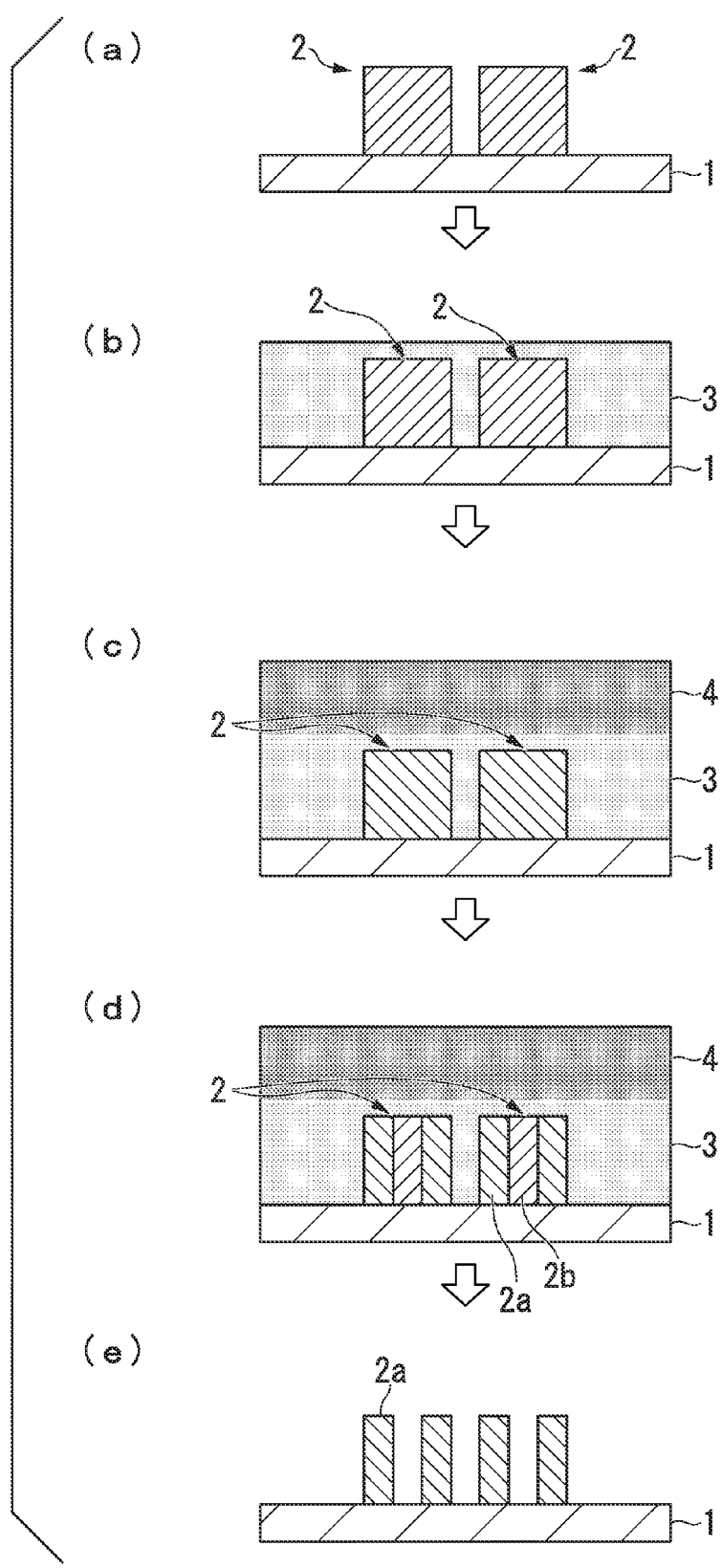
FIG. 1 shows an example of schematic steps of the method of forming a resist pattern (I) according to the present invention.

In the present description and claims, the term "aliphatic" is a relative concept to the term "aromatic", and refers to a group, compound, or the like that has no aromaticity.

The term "alkyl group" includes linear, branched or cyclic monovalent saturated hydrocarbon group, unless otherwise specified.

The term "alkylene group" includes linear, branched or cyclic divalent saturated hydrocarbon group, unless otherwise specified. The same applies to the alkyl group within an alkoxy group.

A "halogenated alkyl group" is a group in which part or all of the hydrogen atoms of an alkyl group is substituted with a halogen atom. Examples of the halogen atom include a fluorine atom, a chlorine atom, a bromine atom, and an iodine atom.

A "fluorinated alkyl group" or a "fluorinated alkylene group" is a group in which part or all of the hydrogen atoms of an alkyl group or an alkylene group is substituted with a fluorine atom.

The term "structural unit" refers to a monomer unit that contributes to the formation of a polymeric compound (resin, polymer, copolymer).

A "structural unit derived from an acrylic ester" refers to a structural unit that is formed by the cleavage of the ethylenic double bond of an acrylic ester.

An "acrylic ester" refers to a compound in which the terminal hydrogen atom of the carboxy group of acrylic acid ($CH_2=CH-COOH$) is substituted with an organic group.

The acrylic ester may have the hydrogen atom bonded to the carbon atom on the α-position substituted with a substituent. The substituent ($R^\alpha$) with which the hydrogen atom bonded to the carbon atom at the α-position is substituted is an atom other than the hydrogen atom or a group, and examples thereof include an alkyl group having 1 to 5 carbon atoms, a halogenated alkyl group having 1 to 5 carbon atoms, and a hydroxyalkyl group. A carbon atom on the α-position of an acrylic ester refers to the carbon atom bonded to the carbonyl group, unless specified otherwise.

Hereafter, an acrylic ester having the hydrogen atom bonded to the carbon atom on the α-position substituted with a substituent is sometimes referred to as "α-substituted acrylic ester". Further, acrylic esters and α-substituted acrylic esters are collectively referred to as "(α-substituted) acrylic ester" in some cases.

A "structural unit derived from a hydroxystyrene derivative" refers to a structural unit that is formed by the cleavage of the ethylenic double bond of hydroxystyrene or a hydroxystyrene derivative.

The term "hydroxystyrene derivative" includes compounds in which the hydrogen atom at the α-position of hydroxystyrene is substituted with another substituent such as an alkyl group or a halogenated alkyl group; and derivatives thereof. Examples of the derivatives thereof include compounds in which the hydrogen atom of the hydroxy group of hydroxystyrene, of which the hydrogen atom on the α-position may be substituted with a substituent, is substituted with an organic group; and compounds in which a substituent other than a hydroxy group is bonded to the benzene ring of hydroxystyrene, of which the hydrogen atom on the α-position may be substituted with a substituent. Here, the α-position (carbon atom on the α-position) refers to the carbon atom having the benzene ring bonded thereto, unless specified otherwise.

As the substituent which substitutes the hydrogen atom on the α-position of hydroxystyrene, the same substituents as those described above for the substituent on the α-position of the aforementioned α-substituted acrylic ester can be mentioned.

A "structural unit derived from vinylbenzoic acid or a vinylbenzoic acid derivative" refers to a structural unit that is formed by the cleavage of the ethylenic double bond of vinylbenzoic acid or a vinylbenzoic acid derivative.

The term "vinylbenzoic acid derivative" includes compounds in which the hydrogen atom at the α-position of vinylbenzoic acid is substituted with another substituent such as an alkyl group, a halogenated alkyl group, or the like; and derivatives thereof. Examples of the derivatives thereof include compounds in which the hydrogen atom of the carboxy group of vinylbenzoic acid, of which the hydrogen atom on the α-position may be substituted with a substituent, is substituted with an organic group; and compounds in which a substituent other than a hydroxy group and a carboxy group is bonded to the benzene ring of a vinylbenzoic acid, of which the hydrogen atom on the α-position may be substituted with a substituent. Here, the α-position (carbon atom on the α-position) refers to the carbon atom having the benzene ring bonded thereto, unless specified otherwise.

The term "styrene derivative" refers to a compound in which the hydrogen atom at the α-position of styrene is substituted with other substituent such as an alkyl group and a halogenated alkyl group.

A "structural unit derived from styrene" or "structural unit derived from a styrene derivative" refers to a structural unit that is formed by the cleavage of the ethylenic double bond of styrene or a styrene derivative.

As the alkyl group as a substituent on the α-position, a linear or branched alkyl group is preferable, and specific examples include alkyl groups having 1 to 5 carbon atoms, such as a methyl group, an ethyl group, a propyl group, an isopropyl group, an n-butyl group, an isobutyl group, a tert-butyl group, a pentyl group, an isopentyl group, and a neopentyl group.

Specific examples of the halogenated alkyl group as the substituent on the α-position include groups in which part or all of the hydrogen atoms of the aforementioned "alkyl group as the substituent on the α-position" are substituted with halogen atoms. Examples of the halogen atom include a fluorine atom, a chlorine atom, a bromine atom, an iodine atom, and a fluorine atom is particularly preferable.

Specific examples of the hydroxyalkyl group as the substituent on the α-position include groups in which part or all of the hydrogen atoms of the aforementioned "alkyl group as the substituent on the α-position" are substituted with a hydroxy group. The number of hydroxy groups within the hydroxyalkyl group is preferably 1 to 5, and most preferably 1.

The case of describing "may have a substituent" includes both of the case where the hydrogen atom (—H) is substituted with a monovalent group and the case where the methylene group (—CH$_2$—) is substituted with a divalent group.

The term "exposure" is used as a general concept that includes irradiation with any form of radiation.

<<First Aspect: Method of Forming Resist Pattern>>

The method of forming a resist pattern according to the first aspect of the present invention includes a step A in which a positive resist composition is applied to a substrate to form a positive resist film, the positive resist film is exposed and the positive resist film is subjected to an alkali development to form a first resist pattern; a step B in which a solution containing an acid or a thermoacid generator is applied to the substrate whereon the first resist pattern is formed, so as to cover the first resist pattern, to form a structure having the first resist pattern and a first layer covering the first resist pattern; a step C in which the structure is heated and the solubility of the first resist pattern in an organic solvent is changed under action of the acid or under action of acid generated from the thermoacid generator; and a step D in which the structure after heating is developed with the organic solvent to remove a region of the first resist pattern other than the region of the first resist pattern where the solubility in the organic solvent is changed, so as to form a second resist pattern.

Hereinbelow, the present invention will be described in accordance with specific embodiments.

First Embodiment

Method of Forming a Resist Pattern (I)

The method of forming a resist pattern according to the first embodiment of the present invention (hereafter, sometimes referred to as "method of forming a resist pattern (I)") includes a step A in which a positive resist composition is applied to a substrate to form a positive resist film, the positive resist film is exposed and the resist film is subjected to an alkali development to form a first resist pattern; a step B in which a solution containing an acid or a thermoacid generator is applied to the substrate whereon the first resist pattern is formed, so as to cover the first resist pattern, to form a structure having the first resist pattern and a first layer covering the first resist pattern; a step B1 in which a solution containing a solvent is applied, so as to cover the structure; a step C in which the structure is heated and the solubility of the first resist pattern in an organic solvent is changed under action of the acid or under action of acid generated from the thermoacid generator; and a step D in which the structure after heating is developed with the organic solvent to remove a region of the first resist pattern other than the region of the first resist pattern where the solubility in the organic solvent is changed, so as to form a second resist pattern.

Hereinbelow, the method of forming a resist pattern (I) according to the present invention will be described with reference to the accompanying drawing.

FIG. 1 shows schematic steps of the resist pattern forming method (I) according to the first embodiment. FIG. 1(a) to (e) show a cross-sectional view of the resist pattern. Firstly, as shown in FIG. 1(a), a resist pattern 2 having a line and space pattern is formed on a substrate 1 using the positive resist composition (step A).

Subsequently, as shown in FIG. 1(b), a solution containing an acid or a thermoacid generator is applied, so as to cover the resist pattern 2, to form a structure having the first resist pattern 2 and a first layer 3 covering the first resist pattern 2 (step B).

Further, as shown in FIG. 1(c), a solution containing a solvent is applied, so as to cover the structure to form a solution layer 4 containing the solvent (step B1).

Then, as shown in FIG. 1(d), the solubility of the first resist pattern 2 surface in a developing solution is changed by heating the structure having the first resist pattern which is formed in the step A to C (step C).

Thereafter, a development with an organic solvent is conducted to remove the region shown as 2b in FIG. 1(d), so as to form a fine pattern in which the first resist pattern is split into line, space and line (hereafter, sometimes referred to as "split pattern") as shown in FIG. 1(e) (step D).

Step A

Step A is a step of forming a positive-type resist film on a support, exposing the positive-type resist film to light, and alkali-developing the light-exposed positive-type resist film to form a first resist pattern. In step A, as shown in FIG. 1(a), a first resist pattern 2 is formed on a support 1.

[Support]

The support is not particularly limited, and a conventionally known support can be used as the support. For example, substrates for electronic components, and such substrates having predetermined wiring patterns formed thereon can be used. Specific examples of the material of the support include a substrate made of metals such as silicon wafer, copper, chromium, iron and aluminum; and a glass substrate. Examples of materials for the wiring pattern include copper, aluminum, nickel, and gold.

Further, as the support, any one of the above-mentioned supports provided with an inorganic and/or organic film on the surface thereof may be used. As the inorganic film, an inorganic antireflection film (inorganic BARC) can be used. As the organic film, an organic antireflection film (organic BARC) and an organic film such as a lower-layer organic film used in a multilayer resist method can be used.

Here, a "multilayer resist method" is method in which at least one layer of an organic film (lower-layer organic film) and at least one layer of a resist film (upper resist film) are provided on a substrate, and a resist pattern formed on the upper resist film is used as a mask to conduct patterning of the lower-layer organic film. This method is considered as being capable of forming a pattern with a high aspect ratio. More specifically, in the multilayer resist method, a desired thickness can be ensured by the lower-layer organic film, and as a result, the thickness of the resist film can be reduced, and a fine pattern with a high aspect ratio can be formed.

The multilayer resist method is broadly classified into a method in which a double-layer structure consisting of an upper-layer resist film and a lower-layer organic film is formed (double-layer resist method), and a method in which a multilayer structure having at least three layers consisting of an upper-layer resist film, a lower-layer organic film and at least one intermediate layer (thin metal film or the like) provided between the upper-layer resist film and the lower-layer organic film (triple-layer resist method).

The wavelength to be used for exposure is not particularly limited and the exposure can be conducted using radiation such as ArF excimer laser, KrF excimer laser, F2 excimer laser, extreme ultraviolet rays (EUV), vacuum ultraviolet rays (VUV), electron beam (EB), X-rays, and soft X-rays. The resist composition is effective when used for KrF excimer laser, ArF excimer laser, EB and EUV.

The exposure of the resist film may be either a general exposure (dry exposure) conducted in air or an inert gas such as nitrogen, or immersion exposure (liquid immersion lithography).

In immersion lithography, the region between the resist film and the lens at the lowermost point of the exposure apparatus is pre-filled with a solvent (immersion medium) that has a larger refractive index than the refractive index of air, and the exposure (immersion exposure) is conducted in this state.

As the immersion medium, a solvent is preferable, which exhibits a refractive index larger than the refractive index of air but smaller than the refractive index of the resist film to be exposed. The refractive index of the solvent is not particularly limited as long as it satisfies the above-mentioned requirements.

Examples of this solvent which exhibits a refractive index that is larger than the refractive index of air but smaller than the refractive index of the resist film include water, fluorine-based inert liquids, silicon-based solvents, and hydrocarbon-based solvents.

Specific examples of the fluorine-based inert liquids include liquids containing a fluorine-based compound such as $C_3HCl_2F_5$, $C_4F_9OCH_3$, $C_4F_9OC_2H_5$, or $C_5H_3F_7$ as the main component, which have a boiling point within a range preferably from 70° C. to 180° C. and more preferably from 80° C. to 160° C. A fluorine-based inert liquid having a boiling point within the above-mentioned range is preferable in that the removal of the immersion medium after the exposure can be conducted by a simple method.

As a fluorine-based inert liquid, a perfluoroalkyl compound in which all of the hydrogen atoms of the alkyl group are substituted with fluorine atoms is particularly preferable. Examples of perfluoroalkyl compounds include, specifically, perfluoroalkylether compounds and perfluoroalkylamine compounds.

Specifically, an example of the perfluoroalkylether compound is perfluoro(2-butyl-tetrahydrofuran) (boiling point 102° C.), and an example of the perfluoroalkylamine compound is perfluorotributylamine (boiling point 174° C.).

As the immersion medium, water is preferable in terms of cost, safety, environmental issues and versatility.

An example of the alkali developing solution used in an alkali developing process includes an aqueous solution containing 0.1% by weight to 10% by weight of tetramethylammonium hydroxide (TMAH).

The developing treatment can be performed by a conventional developing method. Examples thereof include a method in which the support is immersed in the developing solution for a predetermined time (a dip method), a method in which the developing solution is piled up on the surface of the support by surface tension and maintained for a predetermined time (a puddle method), a method in which the developing solution is sprayed onto the surface of the support (spray method), and a method in which the developing solution is ejected from a developing solution ejecting nozzle while scanning at a constant rate to apply the developing solution to the support rotating at a constant rate (dynamic dispense method).

The rinse treatment using a rinse liquid (washing treatment) can be conducted by a conventional rinse method. Examples of the rinse method include a method in which the rinse liquid is continuously applied to the support rotating at a constant rate (rotational coating method), a method in which the support is immersed in the rinse liquid for a predetermined time (dip method), and a method in which the rinse liquid is sprayed onto the surface of the support (spray method).

Positive-Type Resist Composition

In step A, as the positive-type resist composition used for forming the first resist pattern, a positive-type resist composition, which generate acid upon exposure and exhibits increased solubility in a developing solution under action of acid, can be employed.

It is preferable that the positive-type resist composition (hereinafter, referred to as a "resist composition" in some cases) contains a base component (A) (hereafter, referred to as "component (A)" in some cases) which exhibits changed solubility in a developing solution under action of acid.

When a resist film is formed using the resist composition and this resist film is subjected to a selective exposure, an acid is generated at exposed portions, and this acid acts on the component (A) to increase the solubility of the component (A) in an alkaline developing solution, whereas the solubility of the component (A) in an alkali developing solution is not changed at unexposed portions, thereby causing a difference in solubility in a developing solution between exposed portions and unexposed portions. Therefore, when this resist film is developed, the exposed portions are dissolved and removed to form a positive-type resist pattern.

The resist composition according to the present invention has a function of generating acid upon exposure, and in the resist composition, the component (A) may generate acid upon exposure, or an additive component other than the component (A) may generate acid upon exposure.

Specifically, the resist composition according to the present invention may be a resist composition (1) containing an acid generator component (B) which generates acid upon exposure (hereafter, referred to as "component (B)" in some cases;

a resist composition (2) in which the component (A) is a component which generates acid upon exposure; or a resist composition (3) in which the component (A) is a component which generates acid upon exposure, and further containing the component (B).

That is, when the resist composition of the present invention is the aforementioned resist composition (2) or (3), the component (A) is a "base component which generates acid upon exposure and exhibits changed solubility in a developing solution under action of acid". In the case where the component (A) is a base component which generates acid upon exposure and exhibits increased solubility in a developing solution under action of acid, a component (A1) described later is preferably a polymeric compound which generates acid upon exposure and exhibits increased solubility in a developing solution under action of acid. As the polymeric compound, a resin having a structural unit which generates acid upon exposure can be used. As the structural unit which generates acid upon exposure, a conventional structural unit can be used.

In the present invention, it is particularly preferable that the resist composition is the aforementioned resist composition (1).

<Component (A)>

In the present invention, the term "base component" refers to an organic compound capable of forming a film, and is preferably an organic compound having a molecular weight of 500 or more. When the organic compound has a molecular weight of 500 or more, the film-forming ability is improved, and a photo-sensitive resin pattern of nano level can be easily formed.

The organic compound used as the base component is broadly classified into non-polymers and polymers.

In general, as a non-polymer, any of those which have a molecular weight in the range of 500 to less than 4,000 is used. Hereafter, a "low molecular weight compound" refers to a non-polymer having a molecular weight in the range of 500 to less than 4,000.

As a polymer, any of those which have a molecular weight of 1,000 or more is generally used. Hereafter, a "resin" refers to a polymer having a molecular weight of 1,000 or more.

As the molecular weight of the polymer, the weight average molecular weight in terms of the polystyrene equivalent value determined by gel permeation chromatography (GPC) is used.

As the component (A), a resin, a low molecular weight compound, or a combination thereof may be used.

The component (A) may be a resin that exhibits increased solubility in a developing solution under action of acid.

In the present invention, the component (A) may be a component that generates acid upon exposure.

In the present invention, the component (A) preferably contains a polymeric compound (A1) having a structural unit (hereinafter, referred to as "structural unit (a1)" in some cases) containing an acid decomposable group that exhibits increased polarity by the action of acid and a structural unit (hereinafter, referred to as "structural unit (a2)" in some cases) containing a lactone-containing cyclic group or a carbonate-containing cyclic group.

(Structural Unit (a1))

The structural unit (a1) is a structural unit containing an acid decomposable group that exhibits increased polarity by the action of acid.

The term "acid decomposable group" refers to a group having acid decomposition ability in which at least a part of the bond within the structure thereof can be cleaved by the action of an acid.

Examples of acid decomposable groups which exhibit increased polarity by the action of an acid include groups which are decomposed by the action of an acid to form a polar group.

Examples of the polar group include a carboxy group, a hydroxy group, an amino group and a sulfo group (—$SO_3H$). Among these, a polar group containing —OH in the structure thereof (hereafter, referred to as "OH-containing polar group" in some cases) is preferable, a carboxy group or a hydroxy group is more preferable, and a carboxy group is particularly preferable.

More specifically, as an example of an acid decomposable group, a group in which the aforementioned polar group has been protected with an acid dissociable group (such as a group in which the hydrogen atom of the OH-containing polar group has been protected with an acid dissociable group) is given.

The "acid dissociable group" herein refers to both (i) a group having acid dissociability in which the bond between the acid dissociable group and the atom adjacent to the acid dissociable group can be cleaved by the action of acid; and (ii) a group in which a part of the bond is cleaved by the action of acid, and then a decarboxylation reaction occurs, thereby being capable of cleaving the bond between the acid dissociable group and the atom adjacent to the acid dissociable group.

It is necessary that the acid dissociable group that constitutes the acid decomposable group is a group which exhibits a lower polarity than the polar group formed by the dissociation of the acid dissociable group. Thus, when the acid dissociable group is dissociated by the action of acid, a polar group exhibiting a higher polarity than that of the acid dissociable group is formed, thereby increasing the polarity. As a result, the polarity of the entire component (A1) is increased. By the increase in the polarity, the solubility in an alkali developing solution changes, and the solubility in an organic developing solution is relatively decreased.

The acid dissociable group is not particularly limited, and any of the groups that have been conventionally proposed as acid dissociable groups for the base resins of chemically amplified resists can be used.

Examples of the acid dissociable group for protecting the carboxy group or hydroxy group among the polar groups described above include the acid dissociable group represented by general formula (a1-r-1) shown below (hereafter, for the sake of convenience, sometimes referred to as "acetal-type acid dissociable group").

[Chemical Formula 1]

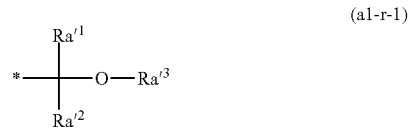

(a1-r-1)

In the formula, $Ra^{t1}$ and $Ra^{t2}$ represent a hydrogen atom or an alkyl group; and $Ra^{t3}$ represents a hydrocarbon group, and $Ra^{t3}$ may be bonded to $Ra^{t1}$ or $Ra^{t2}$ to form a ring. "*" represents a valence bond.

In formula (a1-r-1), as the alkyl group for $Ra^{t1}$ and $Ra^{t2}$, the same alkyl groups as those described above as the substituent which may be bonded to the carbon atom on the α-position of the aforementioned α-substituted acrylic ester can be used, although a methyl group or ethyl group is preferable, and a methyl group is most preferable.

The hydrocarbon group for $Ra^{t3}$ is preferably an alkyl group having 1 to 20 carbon atoms, more preferably an alkyl group having 1 to 10 carbon atoms, and still more preferably a linear or branched alkyl group. Specific examples thereof include a methyl group, an ethyl group, a propyl group, an isopropyl group, an n-butyl group, an isobutyl group, a tert-butyl group, a pentyl group, an isopentyl group, a neopentyl group, a 1,1-dimethylethyl group, a 1,1-diethylpropyl group, a 2,2-dimethylpropyl group and a 2,2-dimethylbutyl group.

In the case where $Ra^{t3}$ represents a cyclic hydrocarbon group, the cyclic hydrocarbon group may be aliphatic or aromatic, and may be polycyclic or monocyclic. As the monocyclic alicyclic hydrocarbon group, a group in which one hydrogen atom has been removed from a monocycloalkane is preferable. The monocycloalkane preferably has 3 to 8 carbon atoms, and specific examples thereof include cyclopentane, cyclohexane and cyclooctane. As the polycyclic alicyclic hydrocarbon group, a group in which one hydrogen atom has been removed from a polycycloalkane is preferable, and the polycycloalkane preferably has 7 to 12 carbon atoms. Examples of the polycycloalkane include, specifically, adamantane, norbornane, isobornane, tricyclodecane and tetracyclododecane.

In the case where the hydrocarbon group is an aromatic hydrocarbon group, examples of the aromatic ring contained in the aromatic hydrocarbon group include aromatic hydrocarbon rings, such as benzene, biphenyl, fluorene, naphthalene, anthracene and phenanthrene; and aromatic hetero rings in which a part of the carbon atoms constituting the aforementioned aromatic hydrocarbon rings has been substituted with a hetero atom. Examples of the hetero atom within the aromatic hetero rings include an oxygen atom, a sulfur atom and a nitrogen atom.

Specific examples of the aromatic hydrocarbon group include a group in which one hydrogen atom has been removed from the aforementioned aromatic hydrocarbon ring (aryl group); and a group in which 1 hydrogen atom of the aforementioned aryl group has been substituted with an alkylene group (for example, an arylalkyl group such as a benzyl group, a phenethyl group, a 1-naphthylmethyl group, a 2-naphthylmethyl group, a 1-naphthylethyl group or a 2-naphthylethyl group). The alkylene group (alkyl chain within the arylalkyl group) preferably has 1 to 4 carbon atom, more preferably 1 or 2, and particularly preferably 1.

In the case where $Ra'^3$ is bonded to $Ra'^1$ or $Ra'^2$ to form a ring, the cyclic group is preferably a 4 to 7-membered ring, and more preferably a 4 to 6-membered ring. Specific examples of the cyclic group include tetrahydropyranyl group and tetrahydrofuranyl group.

Examples of the acid dissociable group for protecting the carboxy group among the polar groups described above include the acid dissociable group represented by general formula (a1-r-2) shown below (hereafter, for the sake of convenience, among the acid dissociable groups represented by the following formula (a1-r-2), the acid dissociable group constituted of alkyl groups is referred to as "tertiary alkyl ester-type acid dissociable group" in some cases).

[Chemical Formula 2]

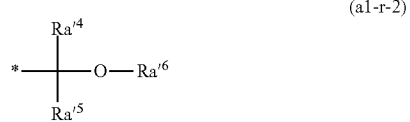

(a1-r-2)

In the formula, $Ra'^4$ to $Ra'^6$ each independently represents a hydrocarbon group, and $Ra'^5$ and $Ra'^6$ may be mutually bonded to form a ring. "*" represents a valence bond.

As the hydrocarbon group for $Ra'^4$ to $Ra'^6$, the same groups as those described above for $Ra'^3$ can be mentioned. $Ra'^4$ is preferably an alkyl group having from 1 to 5 carbon atoms. In the case where $Ra'^5$ and $Ra'^6$ are mutually bonded to form a ring, a group represented by general formula (a1-r2-1) shown below can be mentioned.

On the other hand, in the case where $Ra'^4$ to $Ra'^6$ are not mutually bonded and independently represent a hydrocarbon group, the group represented by general formula (a1-r2-2) shown below can be mentioned.

[Chemical Formula 3]

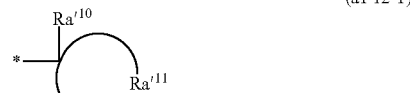

(a1-r2-1)

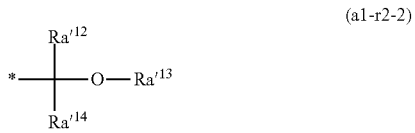

(a1-r2-2)

In the formulae, $Ra'^{10}$ represents an alkyl group having 1 to 10 carbon atoms; $Ra'^{11}$ is a group which forms an aliphatic cyclic group together with a carbon atom having $Ra'^{10}$ bonded thereto; and $Ra'^{12}$ to $Ra'^{14}$ each independently represents a hydrocarbon group. "*" represents a valence bond.

In the formula (a1-r2-1), as the alkyl group having 1 to 10 carbon atoms for $Ra'^{10}$, the same groups as described above for the linear or branched alkyl group for $Ra'^3$ in the formula (a1-r-1) are preferable. In the formula (a1-r2-1), as the aliphatic cyclic group which is formed by $Ra'^{11}$, the same groups as those described above for the cyclic alkyl group for $Ra'^3$ in the formula (a1-r-1) are preferable.

In the formula (a1-r2-2), it is preferable that $Ra'^{12}$ and $Ra'^{14}$ each independently represents an alkyl group having 1 to 10 carbon atoms, and it is more preferable that the alkyl group is the same group as those described above for the linear or branched alkyl group for $Ra'^3$ in the formula (a1-r-1), it is still more preferable that the alkyl group is a linear alkyl group having 1 to 5 carbon atoms, and it is particularly preferable that the alkyl group is a methyl group or an ethyl group.

In the formula (a1-r2-2), it is preferable that $Ra'^{13}$ is the same group as those described above for the linear, branched or cyclic alkyl group exemplified as a hydrocarbon group of $Ra'^3$ in the formula (a1-r-1). Among these, the same cyclic alkyl group as those describe above for $Ra'^3$ is more preferable.

Specific examples of the formula (a1-r2-1) are shown below. In the formulae shown below, and "*" represents a valence bond.

[Chemical Formula 4]

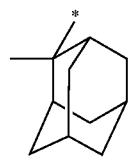

(r-pr-m1)

(r-pr-m2)

(r-pr-m3)
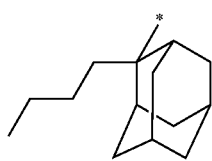
(r-pr-m4)
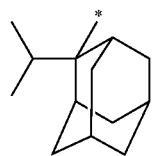
(r-pr-m5)
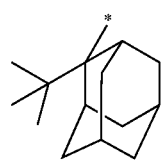
(r-pr-m6)
(r-pr-m7)
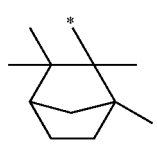
(r-pr-m8)
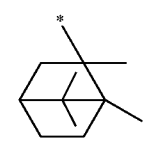
(r-pr-m9)
(r-pr-m10)
(r-pr-m11)
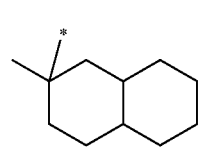
(r-pr-m12)
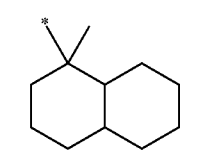
(r-pr-m13)
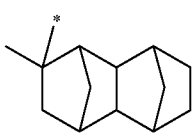
(r-pr-m14)
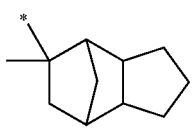
(r-pr-m15)
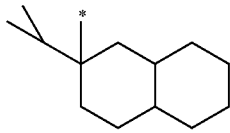
(r-pr-m16)
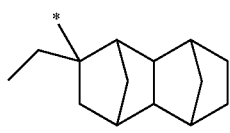
(r-pr-m17)
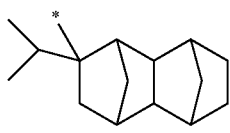
(r-pr-s1)
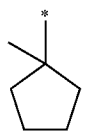
(r-pr-s2)
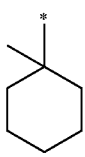
(r-pr-s3)
(r-pr-s4)
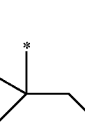
(r-pr-s5)
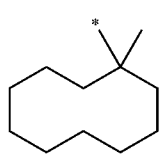

-continued
(r-pr-s6)
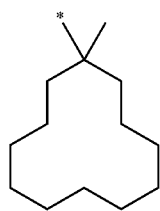
(r-pr-s7)
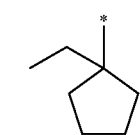
(r-pr-s8)
(r-pr-s9)
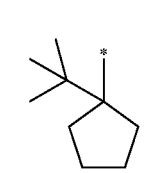
(r-pr-s10)
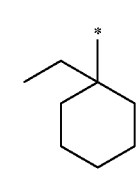
(r-pr-s11)
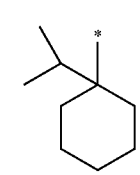
(r-pr-s12)
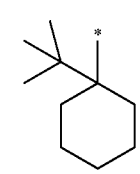
(r-pr-s13)
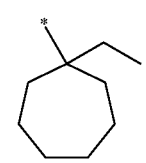
(r-pr-s14)
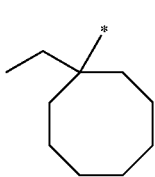
-continued
(r-pr-s15)
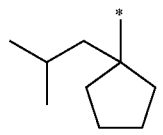
(r-pr-s16)
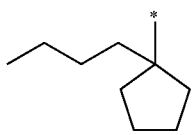
(r-pr-s17)
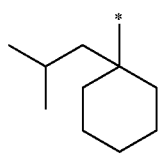
(r-pr-s18)
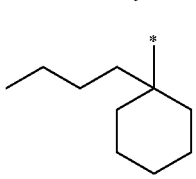
Specific examples of the formula (a1-r2-2) are shown below.
[Chemical Formula 5]
(r-pr-cm1)
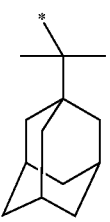
(r-pr-cm2)
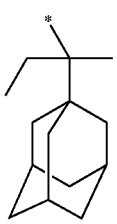
(r-pr-cm3)
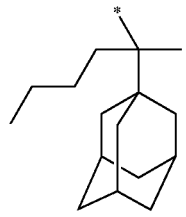
(r-pr-cm4)
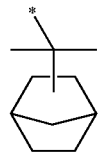

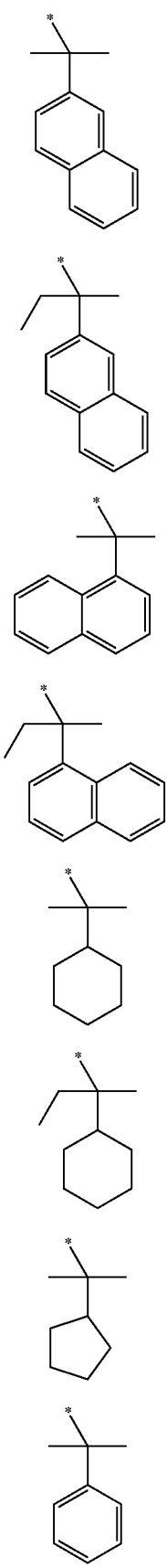

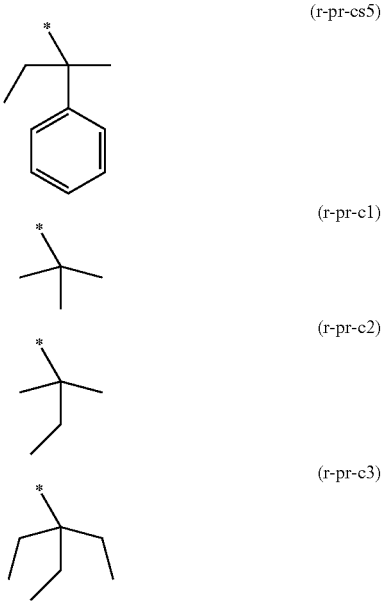

Examples of the acid dissociable group for protecting a hydroxy group among the polar groups described above include the acid dissociable group represented by general formula (a1-r-3) shown below (hereafter, for the sake of convenience, referred to as "tertiary alkyloxycarbonyl-type acid dissociable group" in some cases).

[Chemical Formula 6]

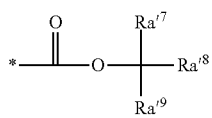

(a1-r-3)

In the formula, $Ra'^7$ to $Ra'^9$ each independently represents an alkyl group. "*" represents a valence bond.

In the formula (a1-r-3), $Ra'^7$ to $Ra'^9$ is preferably an alkyl group having 1 to 5 carbon atoms, and more preferably an alkyl group having 1 to 3 carbon atoms.

Further, the total number of carbon atoms in each alkyl group is preferably 3 to 7, more preferably 3 to 5, and most preferably 3 or 4.

Examples of the structural unit (a1) include a structural unit derived from an acrylic ester in which the hydrogen atom bonded to the carbon atom on the α-position may be substituted with a substituent and which contains an acid decomposable group which exhibits increased polarity by the action of acid; a structural unit in which at least a part of the hydrogen atom of the hydroxy group of a structural unit derived from hydroxystyrene or a hydroxystyrene derivative is protected with a substituent containing the acid decomposable group; and a structural unit in which at least a part of the hydrogen atom within —C(=O)—OH of a structural unit derived from vinylbenzoic acid or a vinylbenzoic acid derivative is protected with a substituent containing the acid decomposable group.

As the structural unit (a1), a structural unit derived from an acrylic ester in which the hydrogen atom bonded to the carbon atom on the α-position may be substituted with a substituent is preferable.

As the structural unit (a1), structural units represented by general formula (a1-1) or (a1-2) shown below are preferable.

[Chemical Formula 7]

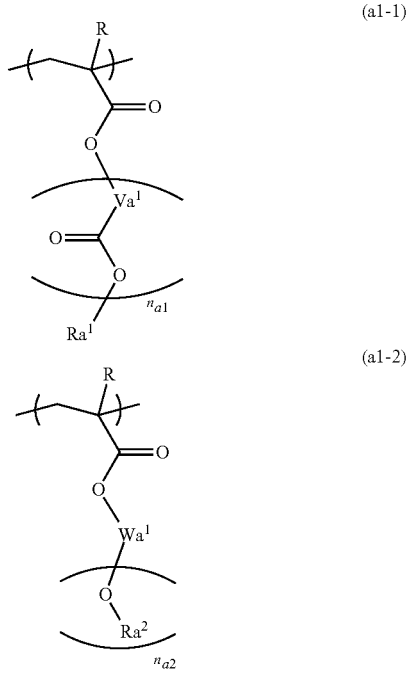

In the formulae, R represents a hydrogen atom, an alkyl group having 1 to 5 carbon atoms or a halogenated alkyl group having 1 to 5 carbon atoms. $Va^1$ represents a divalent hydrocarbon group which may have an ether bond, a urethane bond or an amide bond, and $n_{a1}$ represents an integer of 0 to 2.

$Ra^1$ represents an acid dissociable group represented by the aforementioned formula (a1-r-1) or (a1-r-2). $Wa^1$ represents a hydrocarbon group having a valency of $n_{a2}+1$, $n_{a2}$ represents an integer of 1 to 3, and $Ra^2$ represents an acid dissociable group represented by the aforementioned formula (a1-r-1) or (a1-r-3);

In general formula (a1-1), as the alkyl group having 1 to 5 carbon atoms, a linear or branched alkyl group having 1 to 5 carbon atoms is preferable, and specific examples thereof include a methyl group, an ethyl group, a propyl group, an isopropyl group, an n-butyl group, an isobutyl group, a tert-butyl group, a pentyl group, an isopentyl group and a neopentyl group. The halogenated alkyl group having 1 to 5 carbon atoms is a group in which part or all of the hydrogen atoms of the aforementioned alkyl group having 1 to 5 carbon atoms have been substituted with halogen atoms. Examples of the halogen atom include a fluorine atom, a chlorine atom, a bromine atom and an iodine atom, and a fluorine atom is particularly preferable.

As R, a hydrogen atom, an alkyl group having 1 to 5 carbon atoms or a fluorinated alkyl group having 1 to 5 carbon atoms is preferable, and a hydrogen atom or a methyl group is particularly preferable in terms of industrial availability.

The hydrocarbon group for $Va^1$ may be either an aliphatic hydrocarbon group or an aromatic hydrocarbon group. An "aliphatic hydrocarbon group" refers to a hydrocarbon group that has no aromaticity. The aliphatic hydrocarbon group as the divalent hydrocarbon group for $Va^1$ may be either saturated or unsaturated. In general, the aliphatic hydrocarbon group is preferably saturated.

As more specific examples of the aliphatic hydrocarbon group, a linear or branched aliphatic hydrocarbon group, and an aliphatic hydrocarbon group containing a ring in the structure thereof are given.

Further, as the group for $Va^1$, a group in which the aforementioned divalent hydrocarbon group has been bonded via an ether bond, urethane bond or amide bond can be mentioned.

The linear or branched aliphatic hydrocarbon group preferably has 1 to 10 carbon atoms, more preferably 1 to 6, still more preferably 1 to 4, and most preferably 1 to 3.

As the linear aliphatic hydrocarbon group, a linear alkylene group is preferable. Specific examples thereof include a methylene group $[-CH_2-]$, an ethylene group $[-(CH_2)_2-]$, a trimethylene group $[-(CH_2)_3-]$, a tetramethylene group $[-(CH_2)_4-]$ and a pentamethylene group $[-(CH_2)_5-]$.

As the branched aliphatic hydrocarbon group, branched alkylene groups are preferable, and specific examples include various alkylalkylene groups, including alkylmethylene groups such as $-CH(CH_3)-$, $-CH(CH_2CH_3)-$, $-C(CH_3)_2-$, $-C(CH_3)(CH_2CH_3)-$, $-C(CH_3)(CH_2CH_2CH_3)-$, and $-C(CH_2CH_3)_2-$; alkylethylene groups such as $-CH(CH_3)CH_2-$, $-CH(CH_3)CH(CH_3)-$, $-C(CH_3)_2CH_2-$, $-CH(CH_2CH_3)CH_2-$, and $-C(CH_2CH_3)_2-CH_2-$; alkyltrimethylene groups such as $-CH(CH_3)CH_2CH_2-$, and $-CH_2CH(CH_3)CH_2-$; and alkyltetramethylene groups such as $-CH(CH_3)CH_2CH_2CH_2-$, and $-CH_2CH(CH_3)CH_2CH_2-$. As the alkyl group within the alkylalkylene group, a linear alkyl group having 1 to 5 carbon atoms is preferable.

As examples of the aliphatic hydrocarbon group containing a ring in the structure thereof, an alicyclic hydrocarbon group (a group in which two hydrogen atoms have been removed from an aliphatic hydrocarbon ring), a group in which the alicyclic hydrocarbon group is bonded to the terminal of the linear or branched aliphatic hydrocarbon group, and a group in which the alicyclic hydrocarbon group is interposed within the linear or branched aliphatic hydrocarbon group, can be given. As the linear or branched aliphatic hydrocarbon group, the same groups as those described above can be used.

The alicyclic hydrocarbon group preferably has 3 to 20 carbon atoms, and more preferably 3 to 12 carbon atoms.

The alicyclic hydrocarbon group may be either a monocyclic group or a polycyclic group. As the monocyclic alicyclic hydrocarbon group, a group in which 2 hydrogen atoms have been removed from a monocycloalkane is preferable. The monocycloalkane preferably has 3 to 6 carbon atoms, and specific examples thereof include cyclopentane and cyclohexane. As the polycyclic group, a group in which two hydrogen atoms have been removed from a polycycloalkane is preferable, and the polycycloalkane preferably has 7 to 12 carbon atoms. Examples of the polycycloalkane include adamantane, norbornane, isobornane, tricyclodecane and tetracyclododecane.

The aromatic hydrocarbon group is a hydrocarbon group having an aromatic ring.

The aromatic hydrocarbon group as the divalent hydrocarbon group for Va1 preferably has 3 to 30 carbon atoms, more preferably 5 to 30, still more preferably 5 to 20, particularly preferably 6 to 15, and most preferably 6 to 10.

Here, the number of carbon atoms within a substituent(s) is not included in the number of carbon atoms of the aromatic hydrocarbon group.

Examples of the aromatic ring contained in the aromatic hydrocarbon group include aromatic hydrocarbon rings, such as benzene, biphenyl, fluorene, naphthalene, anthracene and phenanthrene; and aromatic hetero rings in which a part of the carbon atoms constituting the aforementioned aromatic hydrocarbon rings has been substituted with a hetero atom. Examples of the hetero atom within the aromatic hetero rings include an oxygen atom, a sulfur atom and a nitrogen atom.

Specific examples of the aromatic hydrocarbon group include a group in which two hydrogen atoms have been removed from the aforementioned aromatic hydrocarbon ring (arylene group); and a group in which one of hydrogen atoms of a group, in which one hydrogen atom has been removed from the aforementioned aromatic hydrocarbon ring (aryl group), has been substituted with an alkylene group (a group in which one hydrogen atom has been further removed from an aryl group in an arylalkyl group such as a benzyl group, a phenethyl group, a 1-naphthylmethyl group, a 2-naphthylmethyl group, a 1-naphthylethyl group, or a 2-naphthylethyl group). The alkylene group (alkyl chain within the arylalkyl group) preferably has 1 to 4 carbon atoms, more preferably 1 or 2 carbon atoms, and most preferably 1 carbon atom.

In the aforementioned formula (a1-2), the hydrocarbon group for $Wa^1$ having a valency of $n_{a2}+1$ may be either an aliphatic hydrocarbon group or an aromatic hydrocarbon group. The aliphatic hydrocarbon group refers to a hydrocarbon group that has no aromaticity, and may be either saturated or unsaturated, but is preferably saturated in general. Examples of the aliphatic hydrocarbon group include a linear or branched aliphatic hydrocarbon group, an aliphatic hydrocarbon group containing a ring in the structure thereof, and a combination of the linear or branched aliphatic hydrocarbon group and the aliphatic hydrocarbon group containing a ring in the structure thereof. As the specific examples thereof, the same groups as those described above for $Va^1$ in the aforementioned formula (a1-1) can be mentioned.

The valency of $n_{a2}+1$ is preferably divalent, trivalent or tetravalent, and divalent or trivalent is more preferable.

As the structural unit (a1-2), a structural unit represented by general formula (a1-2-01) shown below is particularly preferable.

[Chemical Formula 8]

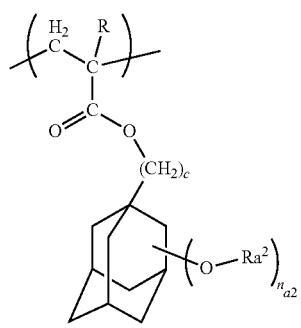

(a1-2-01)

In the formula (a1-2-01), $Ra^2$ represents an acid dissociable group represented by the aforementioned formula (a1-r-1) or (a1-r-3); $n_{a2}$ is an integer of 1 to 3, preferably 1 or 2, and more preferably 1; c is an integer of 0 to 3, preferably 0 or 1, and more preferably 1; R is the same as defined above.

Specific examples of the structural units (a1-1) and (a1-2) are shown below. In the formulae shown below, $R^\alpha$ represents a hydrogen atom, a methyl group or a trifluoromethyl group.

[Chemical Formula 9]

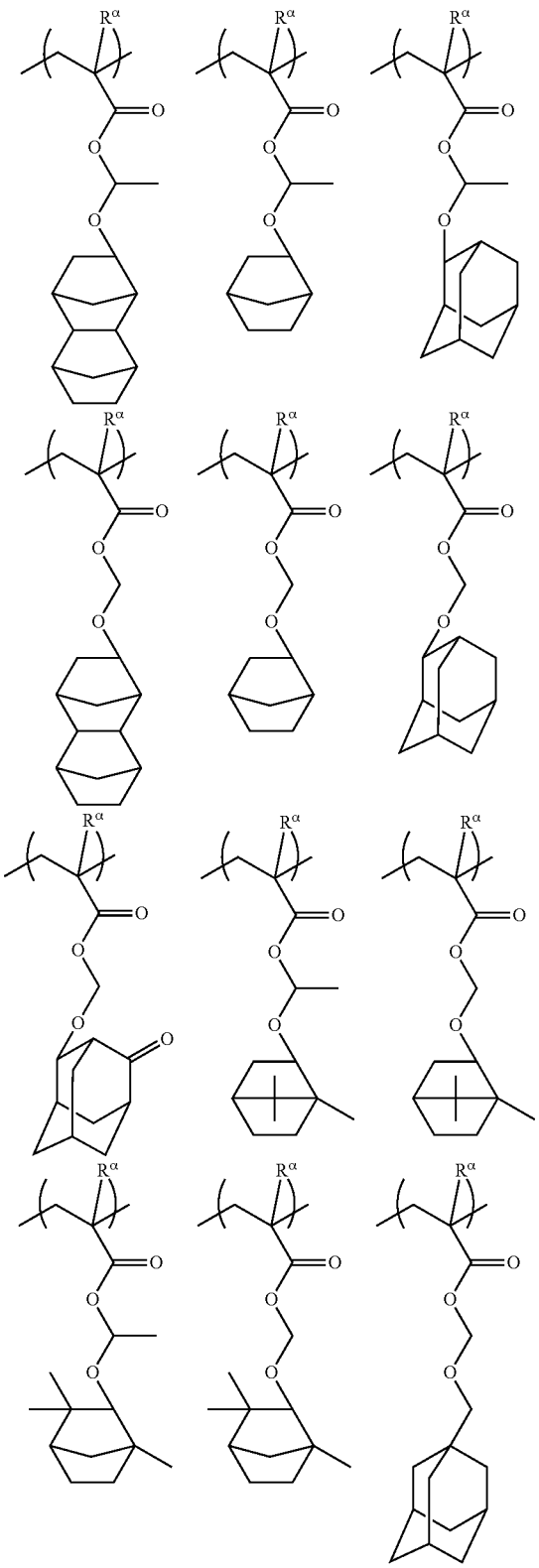

-continued
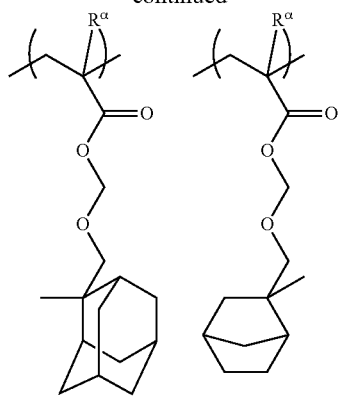
[Chemical Formula 10]
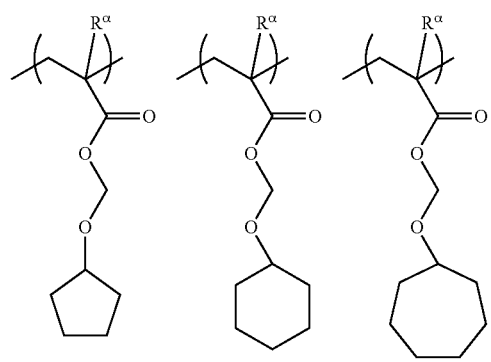
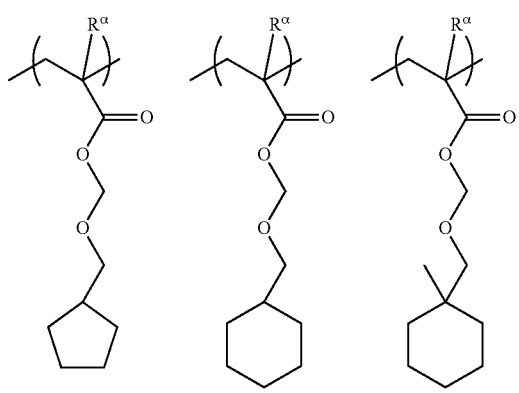
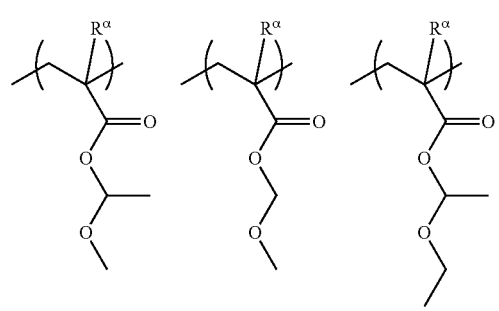
-continued
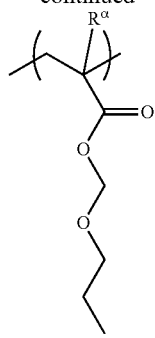
[Chemical Formula 11]
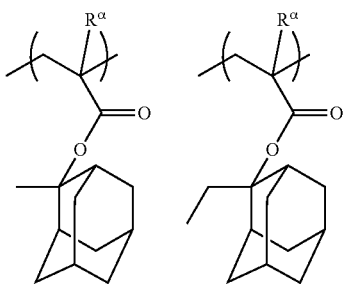
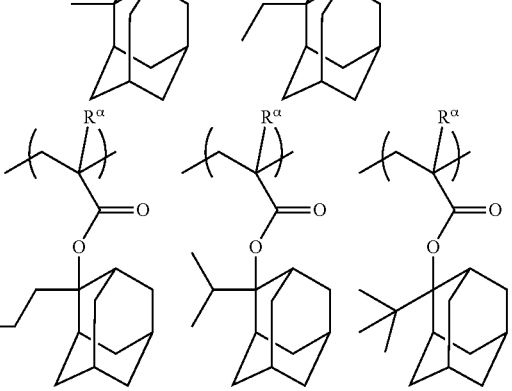
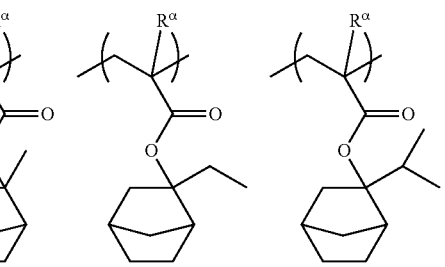
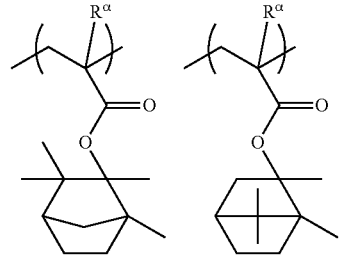
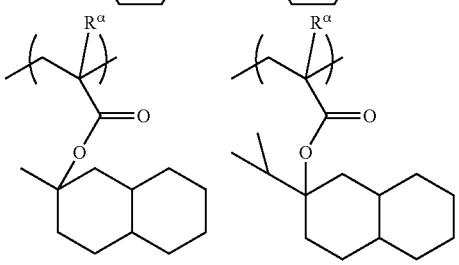

-continued
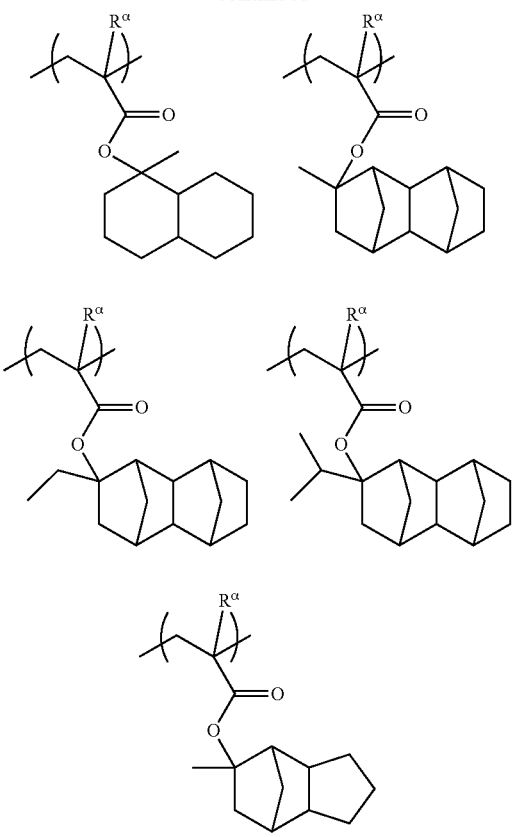
[Chemical Formula 12]
-continued
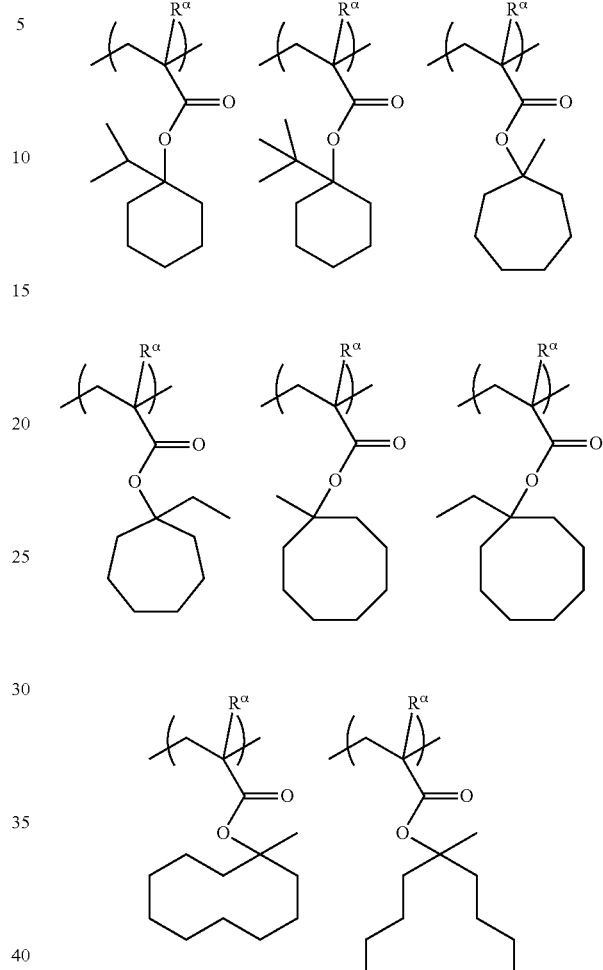
[Chemical Formula 13]

-continued

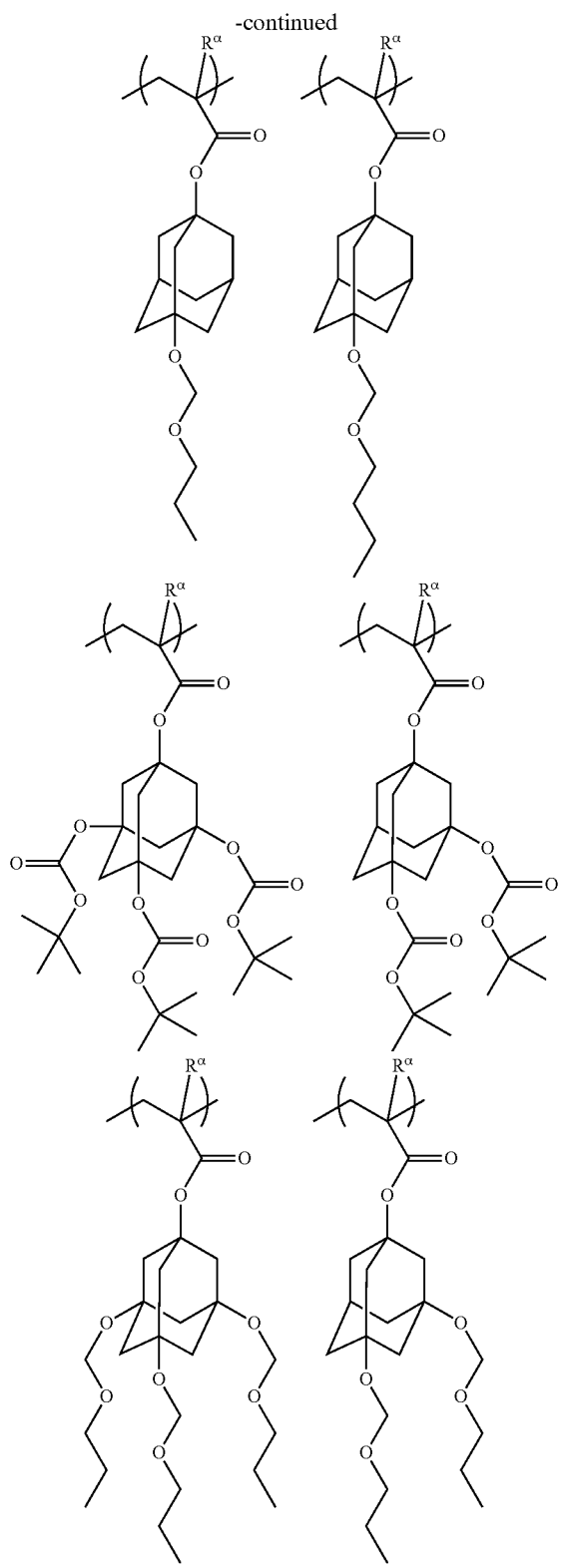

In the component (A), the ratio of the structural unit (a1) based on all structural units constituting the component (A) is preferably 20 to 80 mol %, more preferably 20 to 75 mol %, and still more preferably 25 to 70 mol %. By setting the ratio not to fall below the lower limit, various lithography properties such as sensitivity, resolution and LWR are improved. On the other hand, when setting the ratio not to exceed the upper limit of the above-mentioned range, a good balance can be achieved with the other structural units.

(Structural Unit (a2))

The structural unit (a2) is a structural unit containing a lactone-containing cyclic group or a carbonate-containing cyclic group.

When the component (A1) is used for forming a resist film, a lactone-containing cyclic group or a carbonate-containing cyclic group of the structural unit (a2) is effective in improving the adhesion between the resist film and the substrate.

In the present invention, it is preferable that the component (A1) has the structural unit (a2).

When the aforementioned structural unit (a1) contains a lactone-containing cyclic group, an —$SO_2$— containing cyclic group or a carbonate-containing cyclic group, the structural unit also falls under the definition of the structural unit (a2); however, such a structural unit is regarded as a structural unit (a1), and does not fall under the definition of the structural unit (a2).

The structural unit (a2) is preferably a structural unit represented by general formula (a2-1) shown below.

[Chemical Formula 14]

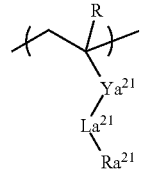

(a2-1)

In the formula, R represents a hydrogen atom, an alkyl group having 1 to 5 carbon atoms, a halogenated alkyl group having 1 to 5 carbon atoms; $Ya^{21}$ represents a single bond or a divalent linking group; $La^{21}$ represents —O—, —COO—, —CON(R')—, —OCO—, —CONHCO— or —CONHCS—; and R' represents a hydrogen atom or a methyl group, provided that, when $La^{21}$ represents —O—, $Ya^{21}$ does not represents —CO—; and $Ra^{21}$ represents a lactone-containing cyclic group, an —$SO_2$— containing cyclic group or a carbonate-containing cyclic group.

The divalent linking group for $Ya^{21}$ is not particularly limited, and preferable examples thereof include a divalent hydrocarbon group which may have a substituent and a divalent linking group containing a hetero atom.

Divalent Hydrocarbon Group which May have a Substituent

The hydrocarbon group as a divalent linking group may be either an aliphatic hydrocarbon group or an aromatic hydrocarbon group.

An "aliphatic hydrocarbon group" refers to a hydrocarbon group that has no aromaticity. The aliphatic hydrocarbon group may be saturated or unsaturated. In general, the aliphatic hydrocarbon group is preferably saturated.

Examples of the aliphatic hydrocarbon group include a linear or branched aliphatic hydrocarbon group, and an aliphatic hydrocarbon group containing a ring in the structure thereof. Specifically, groups exemplified above for $Va^1$ in the aforementioned formula (a1-1) are mentioned.

The linear or branched aliphatic hydrocarbon group may or may not have a substituent. Examples of the substituent include a fluorine atom, a fluorinated alkyl group having 1 to 5 carbon atoms, which is substituted with a fluorine atom, and a carbonyl group.

As examples of the hydrocarbon group containing a ring in the structure thereof, a cyclic aliphatic hydrocarbon group which may have a substituent containing a hetero atom in the ring structure thereof (a group in which two hydrogen atoms have been removed from an aliphatic hydrocarbon ring), a group in which the cyclic aliphatic hydrocarbon group is bonded to the terminal of the linear or branched aliphatic hydrocarbon group, and a group in which the cyclic aliphatic hydrocarbon group is interposed within the linear or branched aliphatic hydrocarbon group, can be given. As the linear or branched aliphatic hydrocarbon group, the same groups as those described above can be used.

The cyclic aliphatic hydrocarbon group preferably has 3 to 20 carbon atoms, and more preferably 3 to 12 carbon atoms.

Specific examples of the cyclic aliphatic hydrocarbon group include the same group as exemplified above for Va1 in the aforementioned formula (a1-1).

The cyclic aliphatic hydrocarbon group may or may not have a substituent. Examples of the substituent include an alkyl group, an alkoxy group, a halogen atom, a halogenated alkyl group, a hydroxy group and a carbonyl group.

The alkyl group as the substituent is preferably an alkyl group having 1 to 5 carbon atoms, and most preferably a methyl group, an ethyl group, a propyl group, an n-butyl group or a tert-butyl group.

The alkoxy group as the substituent is preferably an alkoxy group having 1 to 5 carbon atoms, more preferably a methoxy group, ethoxy group, n-propoxy group, iso-propoxy group, n-butoxy group or tert-butoxy group, and most preferably a methoxy group or an ethoxy group.

Examples of the halogen atom as the substituent include a fluorine atom, a chlorine atom, a bromine atom and an iodine atom, and a fluorine atom is preferable.

Examples of the halogenated alkyl group as the substituent include groups in which a part or all of the hydrogen atoms within the aforementioned alkyl groups has been substituted with the aforementioned halogen atoms.

In the cyclic aliphatic hydrocarbon group, a part of the carbon atoms constituting the ring structure thereof may be substituted with a substituent containing a hetero atom. As the substituent containing a hetero atom, —O—, —C(=O)—O—, —S—, —S(=O)$_2$— or —S(=O)$_2$—O— is preferable.

Specific examples of the aromatic hydrocarbon group as a divalent hydrocarbon group include the same group as exemplified above for Va1 in the aforementioned formula (a1-1).

With respect to the aromatic hydrocarbon group, the hydrogen atom within the aromatic hydrocarbon group may be substituted with a substituent. For example, the hydrogen atom bonded to the aromatic ring within the aromatic hydrocarbon group may be substituted with a substituent. Examples of substituents include an alkyl group, an alkoxy group, a halogen atom, a halogenated alkyl group, and a hydroxy group.

The alkyl group as the substituent is preferably an alkyl group having 1 to 5 carbon atoms, and a methyl group, an ethyl group, a propyl group, an n-butyl group or a tert-butyl group is most preferable.

As the alkoxy group, the halogen atom and the halogenated alkyl group as the substituent, the same groups as the aforementioned substituent groups for substituting a hydrogen atom within the cyclic aliphatic hydrocarbon group can be used.

Divalent Linking Group Containing a Hetero Atom

With respect to a divalent linking group containing a hetero atom, the hetero atom is an atom other than carbon atom and hydrogen atom, and examples thereof include an oxygen atom, a nitrogen atom, a sulfur atom, and a halogen atom.

In the case where Ya$^{21}$ represents a divalent linking group containing a hetero atom, preferable examples of the linking group include —O—, —C(=O)—O—, —C(=O)—, —O—C(=O)—O—, —C(=O)—NH—, —NH—, —NH—C(=NH)— (wherein H may be substituted with a substituent such as an alkyl group or an acyl group), —S—, —S(=O)$_2$—, —S(=O)$_2$—O—, a group represented by general formula —Y$^{21}$—O—Y$^{22}$—, —Y$^{21}$—O—, —Y$^{21}$—C(=O)—O—, —C(=O)—O—Y$^{21}$, [Y$^{21}$—C(=O)—O]$_{m'}$—Y$^{22}$—, or —Y$^{21}$—O—C(=O)—Y$^{22}$— [in the formulae, Y$^{21}$ and Y$^{22}$ each independently represents a divalent hydrocarbon group which may have a substituent, and O represents an oxygen atom; and m' represents an integer of 0 to 3.

The divalent linking group containing a hetero atom represents —C(=O)—NH—, —NH—, or —NH—C(=NH)—, H may be substituted with a substituent such as an alkyl group, an acyl group or the like. The substituent (an alkyl group, an acyl group or the like) preferably has 1 to 10 carbon atoms, more preferably 1 to 8 carbon atoms, and particularly preferably 1 to 5 carbon atoms.

In formulae —Y$^{21}$—O—Y$^{22}$—, —Y$^{21}$—O—, —Y$^{21}$—C(=O)—O—, —C(=O)—O—Y$^{21}$, —[Y$^{21}$—C(=O)—O]$_{m'}$—Y$^{22}$— and —Y$^{21}$—O—C(=O)—Y$^{22}$—, Y$^{21}$ and Y$^{22}$ each independently represents a divalent hydrocarbon group which may have a substituent. Examples of the divalent hydrocarbon group include the same groups as those described above as the "divalent hydrocarbon group which may have a substituent" in the explanation of the aforementioned divalent linking group.

As Y$^{21}$, a linear aliphatic hydrocarbon group is preferable, more preferably a linear alkylene group, still more preferably a linear alkylene group having 1 to 5 carbon atoms, and a methylene group or an ethylene group is particularly preferable.

As Y$^{22}$, a linear or branched aliphatic hydrocarbon group is preferable, and a methylene group, an ethylene group or an alkylmethylene group is more preferable. The alkyl group within the alkylmethylene group is preferably a linear alkyl group having 1 to 5 carbon atoms, more preferably a linear alkyl group having 1 to 3 carbon atoms, and most preferably a methyl group.

In the group represented by the formula —[Y$^{21}$—C(=O)—O]$_{m'}$—Y$^{22}$—, m' represents an integer of 0 to 3, preferably an integer of 0 to 2, more preferably 0 or 1, and most preferably 1. Namely, it is particularly preferable that the group represented by the formula —[Y$^{21}$—C(=O)—O]$_{m'}$—Y$^{22}$— is a group represented by the formula —Y$^{21}$—C(=O)—O—Y$^{22}$—. Among these, a group represented by the formula —(CH$_2$)$_{a'}$—C(=O)—O—(CH$_2$)$_{b'}$— is preferable. In the formula, a' is an integer of 1 to 10, preferably an integer of 1 to 8, more preferably an integer of 1 to 5, still more preferably 1 or 2, and most preferably 1. b' is an integer of 1 to 10, preferably an integer of 1 to 8, more preferably an integer of 1 to 5, still more preferably 1 or 2, and most preferably 1.

In the present invention, $Ya^{21}$ preferably represents an ester bond [—C(=O)—O—], an ether bond (—O—), a linear or branched alkylene group, a combination of these, or a single bond.

The term "lactone-containing cyclic group" refers to a cyclic group including a ring containing —O—C(=O)— (lactone ring) in the ring skeleton thereof. This lactone ring is counted as the first ring. A lactone-containing cyclic group in which the only ring structure is the lactone ring is referred to as a monocyclic group, and groups containing other ring structures are described as polycyclic groups regardless of the structure of the other rings. The lactone-containing cyclic group may be either a monocyclic group or a polycyclic group.

As the lactone-containing cyclic group as a cyclic hydrocarbon group for R1, there is no particular limitation, and an arbitrary group may be used. Specific examples include groups represented by general formulas (a2-r-1) to (a2-r-7) shown below. Hereinbelow, "*" represents a valence bond.

[Chemical Formula 15]

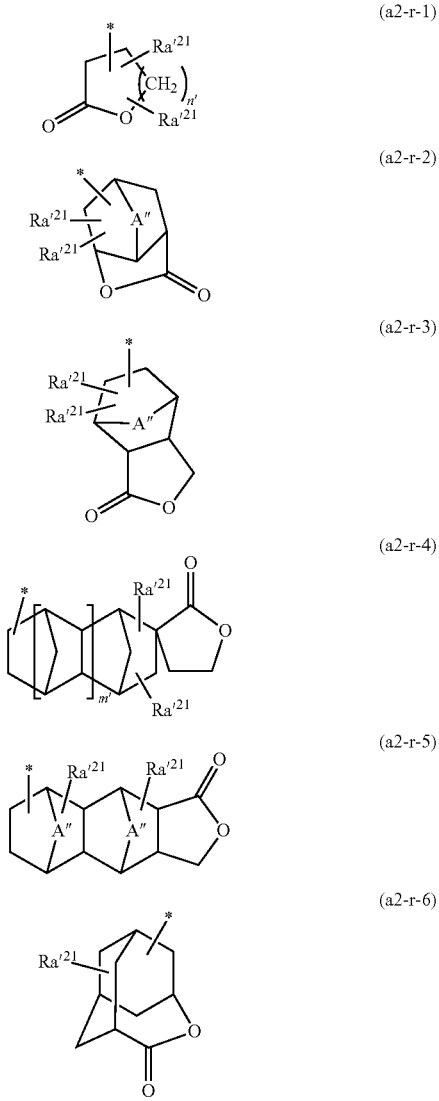

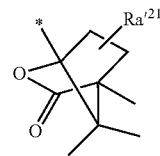

In the formulae, each $Ra'^{21}$ independently represents a hydrogen atom, an alkyl group, an alkoxy group, a halogen atom, a halogenated alkyl group, a hydroxy group, —COOR", —OC(=O)R", a hydroxyalkyl group or a cyano group; R" represents a hydrogen atom or an alkyl group; A" represents an oxygen atom, a sulfur atom or an alkylene group having 1 to 5 carbon atoms which may contain an oxygen atom or a sulfur atom; n' represents an integer of 0 to 2; and m' represents 0 or 1

In general formulae (a2-r-1) to (a2-r-7) above, A" represents an oxygen atom (—O—), a sulfur atom (—S—) or an alkylene group having 1 to 5 carbon atoms which may contain an oxygen atom or a sulfur atom. As the alkylene group having 1 to 5 carbon atoms for A", a linear or branched alkylene group is preferable, and examples thereof include a methylene group, an ethylene group, an n-propylene group and an isopropylene group. Examples of alkylene groups that contain an oxygen atom or a sulfur atom include, specifically, the aforementioned alkylene groups in which —O— or —S— is bonded to the terminal of the alkylene group or present between the carbon atoms of the alkylene group. Specific examples of such alkylene groups include —O—CH$_2$—, —CH$_2$—O—CH$_2$—, —S—CH$_2$— and —CH$_2$—S—CH$_2$—. As A", an alkylene group having 1 to 5 carbon atoms or —O— is preferable, more preferably an alkylene group having 1 to 5 carbon atoms, and most preferably a methylene group. Each $Ra'^{21}$ independently represents an alkyl group, an alkoxy group, a halogen atom, a halogenated alkyl group, —COOR", —OC(=O)R", a hydroxyalkyl group or a cyano group.

The alkyl group for $Ra'^{21}$ is preferably an alkyl group having 1 to 5 carbon atoms.

The alkoxy group for $Ra'^{21}$ is preferably an alkoxy group having 1 to 6 carbon atoms.

The alkoxy group is preferably a linear or branched alkoxy group. Specific examples of the alkoxy groups include the aforementioned alkyl groups for $Ra'^{21}$ having an oxygen atom (—O—) bonded thereto.

As examples of the halogen atom for $Ra'^{21}$, a fluorine atom, chlorine atom, bromine atom and iodine atom can be given. Among these, a fluorine atom is preferable.

Examples of the halogenated alkyl group for $Ra'^{21}$ include groups in which part or all of the hydrogen atoms within the aforementioned alkyl group for $Ra'^{21}$ has been substituted with the aforementioned halogen atoms. As the halogenated alkyl group, a fluorinated alkyl group is preferable, and a perfluoroalkyl group is particularly preferable.

Specific examples of the groups represented by the aforementioned general formulae (a2-r-1) to (a2-r-7) are shown below.

[Chemical Formula 16]

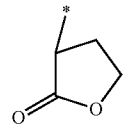

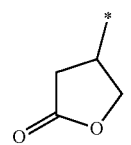 (r-Ic-1-2)
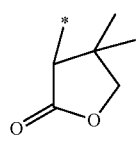 (r-Ic-1-3)
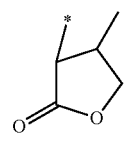 (r-Ic-1-4)
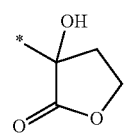 (r-Ic-1-5)
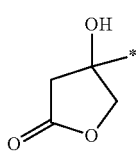 (r-Ic-1-6)
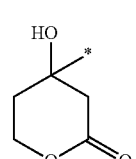 (r-Ic-1-7)
 (r-Ic-2-1)
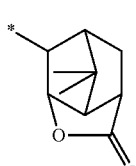 (r-Ic-2-2)
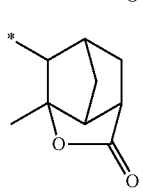 (r-Ic-2-3)
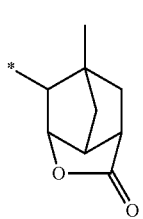 (r-Ic-2-4)
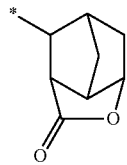 (r-Ic-2-5)
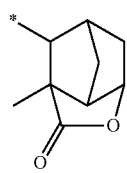 (r-Ic-2-6)
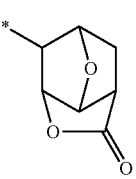 (r-Ic-2-7)
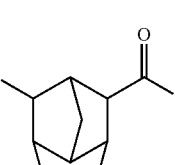 (r-Ic-2-8)
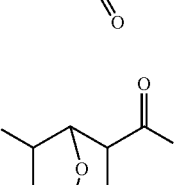 (r-Ic-2-9)
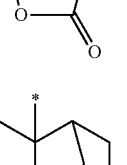 (r-Ic-2-10)
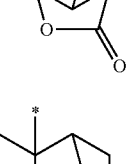 (r-Ic-2-11)
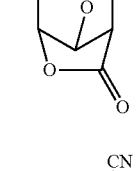 (r-Ic-2-12)

(r-Ic-2-13)
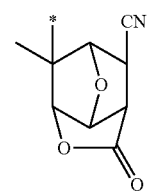
(r-Ic-3-1)
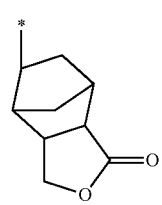
(r-Ic-3-2)
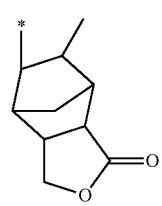
(r-Ic-3-3)
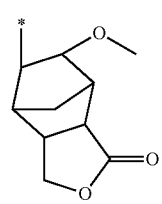
(r-Ic-3-4)
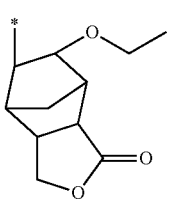
(r-Ic-3-5)
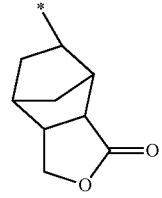
(r-Ic-4-1)
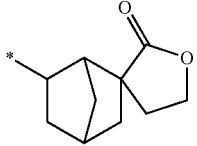
(r-Ic-4-2)
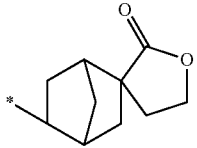
(r-Ic-4-3)
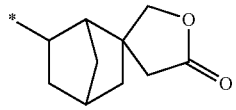
(r-Ic-4-4)
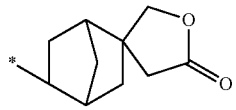
(r-Ic-4-5)
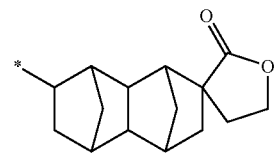
(r-Ic-4-6)
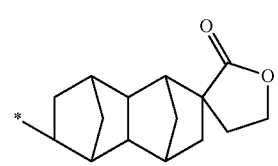
(r-Ic-4-7)
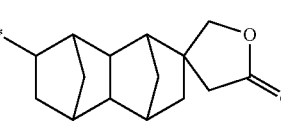
(r-Ic-4-8)
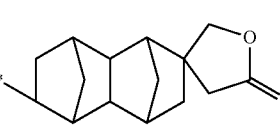
(r-Ic-4-9)
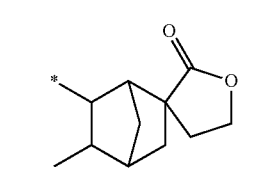
(r-Ic-5-1)
(r-Ic-5-2)
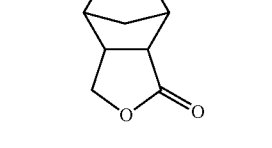
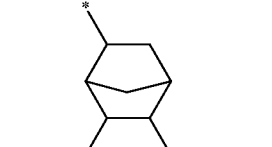
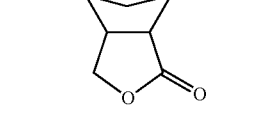

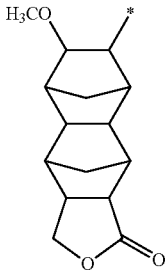
(r-Ic-5-3)

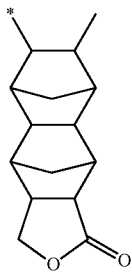
(r-Ic-5-4)

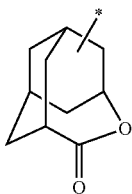
(r-Ic-6-1)

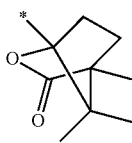
(r-Ic-7-1)

The "—SO$_2$— containing cyclic group" refers to a cyclic group having a ring containing —SO$_2$— in the ring skeleton thereof, i.e., a cyclic group in which the sulfur atom (S) within —SO$_2$— forms a part of the ring skeleton of the cyclic group. The ring containing —SO$_2$— in the ring skeleton thereof is counted as the first ring. A cyclic group in which the only ring structure is the ring that contains —SO$_2$— in the ring skeleton thereof is referred to as a monocyclic group, and a group containing other ring structures is referred to as a polycyclic group regardless of the structure of the other rings. The —SO$_2$— containing cyclic group may be either a monocyclic group or a polycyclic group.

As the —SO$_2$— containing cyclic group for the cyclic hydrocarbon group represented by R$^1$, a cyclic group containing —O—SO$_2$— in the ring skeleton thereof, i.e., a cyclic group containing a sultone ring in which —O—S— within the —O—SO$_2$— group forms a part of the ring skeleton thereof is particularly preferable. Specific examples of the —SO$_2$— containing cyclic group include groups represented by general formulae (a5-r-1) to (a5-r-4) shown below.

[Chemical Formula 17]

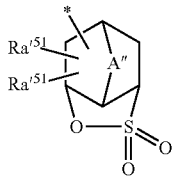
(a5-r-1)

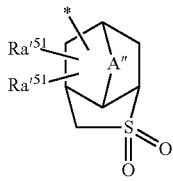
(a5-r-2)

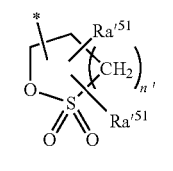
(a5-r-3)

(a5-r-4)

In the formulae, each Ra'$^{51}$ independently represents a hydrogen atom, an alkyl group, an alkoxy group, a halogen atom, a halogenated alkyl group, a hydroxy group, —COOR", —OC(=O)R", a hydroxyalkyl group or a cyano group; R" represents a hydrogen atom or an alkyl group; A" represents an oxygen atom, a sulfur atom or an alkylene group having 1 to 5 carbon atoms which may contain an oxygen atom or a sulfur atom; and n' represents an integer of 0 to 2.

In general formulae (a5-r-1) to (a5-r-4), A" is the same as defined for A" in the above-mentioned general formulae (a2-r-1) to (a2-r-7). The alkyl group, alkoxy group, halogen atom, halogenated alkyl group, —COOR", —OC(=O)R" and hydroxyalkyl group for Ra'$^{51}$ are the same as defined for Ra'21 in the above-mentioned general formulae (a2-r-1) to (a2-r-7).

Specific examples of the groups represented by the aforementioned general formulas (a5-r-1) to (a5-r-4) are shown below. In the formulae shown below, "Ac" represents an acetyl group.

[Chemical Formula 18]

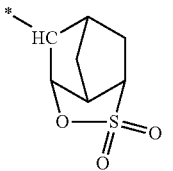
(r-s1-1-1)

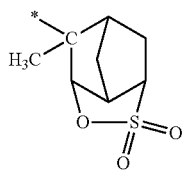
(r-s-1-2)
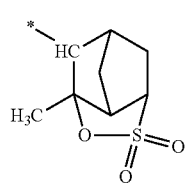
(r-s1-1-3)
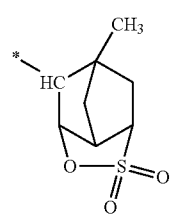
(r-s1-1-4)
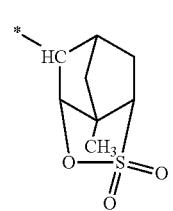
(r-s1-1-5)
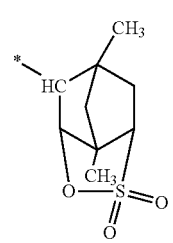
(r-s1-1-6)
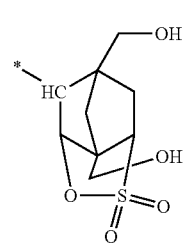
(r-s1-1-7)
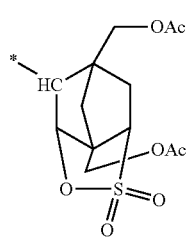
(r-s1-1-8)
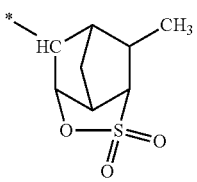
(r-s1-1-9)
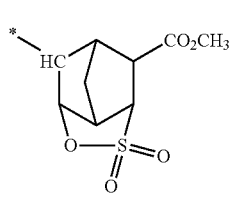
(r-s1-1-10)
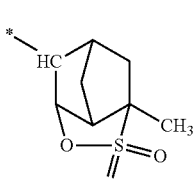
(r-s1-1-11)
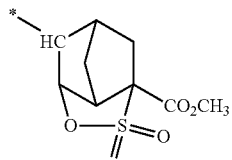
(r-s1-1-12)
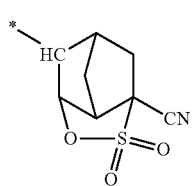
(r-s1-1-13)
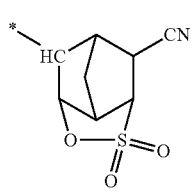
(r-s1-1-14)
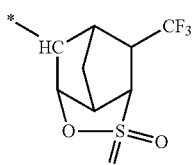
(r-s1-1-15)
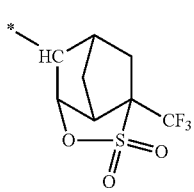
(r-s1-1-16)

-continued
(r-s1-1-17)
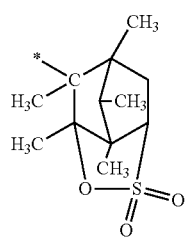
(r-s1-1-18)
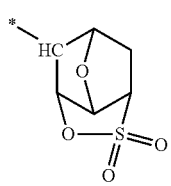
(r-s1-1-19)
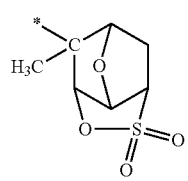
(r-s1-1-20)
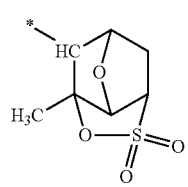
(r-s1-1-21)
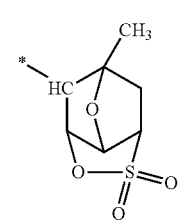
[Chemical Formula 19]
(r-s1-1-22)
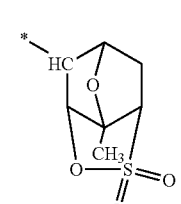
(r-s1-1-23)
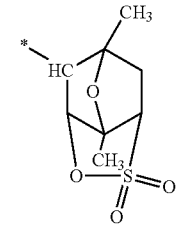
-continued
(r-s1-1-24)
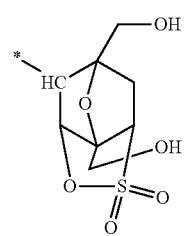
(r-s1-1-25)
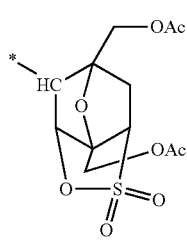
(r-s1-1-26)
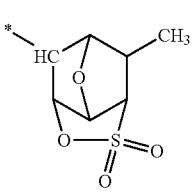
(r-s1-1-27)
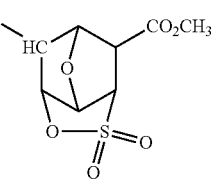
(r-s1-1-28)
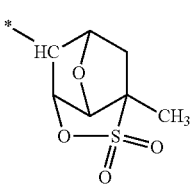
(r-s1-1-29)
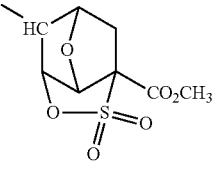
(r-s1-1-30)
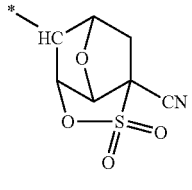
(r-s1-1-31)
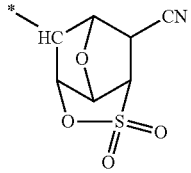

-continued (r-s1-1-32)
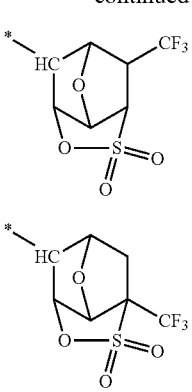

[Chemical Formula 20]

(r-s1-2-1)
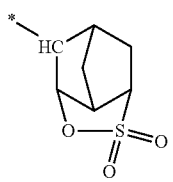

(r-s1-2-2)
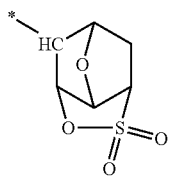

(r-s1-3-1)
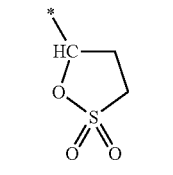

(r-s1-4-2)
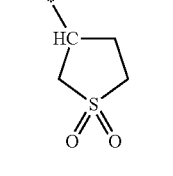

As the —$SO_2$— containing cyclic group, among those described above, a group represented by the aforementioned general formula (a5-r-1) is preferable, at least one kind selected from the group consisting of groups represented by the aforementioned chemical formulas (r-s1-1-1), (r-s1-1-18), (r-s1-3-1) and (r-s1-4-1) is more preferable, and a group represented by chemical formula (r-s1-1-1) is most preferable.

The term "carbonate-containing cyclic group" refers to a cyclic group including a ring containing —O—C(═O)—O— (carbonate ring) in the ring skeleton thereof. A carbonate ring is counted as the first ring, and a carbonate-containing cyclic group in which the only ring structure is the carbonate ring is referred to as a monocyclic group, and groups containing other ring structures are described as polycyclic groups regardless of the structure of the other rings. The carbonate-containing cyclic group may be either a monocyclic group or a polycyclic group.

The carbonate-containing cyclic group as the cyclic hydrocarbon group for $R^1$ is not particularly limited, and an arbitrary group may be used. Specific examples thereof include groups represented by general formulas (ax3-r-1) to (ax3-r-3) shown below.

[Chemical Formula 21]

(ax3-r-1)
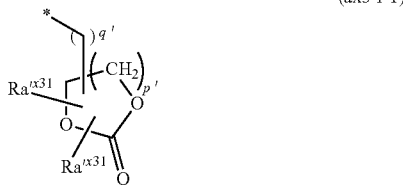

(ax3-r-2)
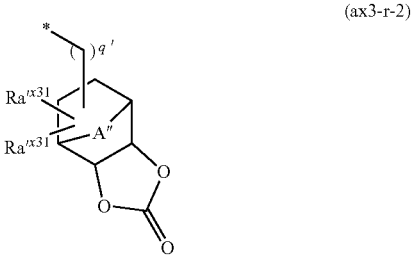

(ax3-r-3)
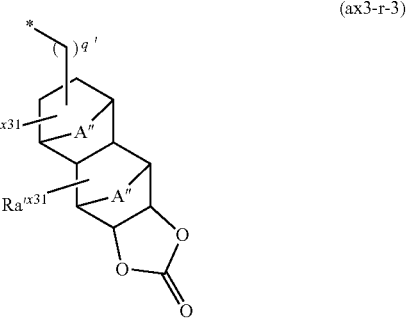

In the formulae, each $Ra'^{x31}$ independently represents a hydrogen atom, an alkyl group, an alkoxy group, a halogen atom, a halogenated alkyl group, a hydroxy group, —COOR", —OC(═O)R", a hydroxyalkyl group or a cyano group; R" represents a hydrogen atom or an alkyl group; A" represents an oxygen atom, a sulfur atom or an alkylene group having 1 to 5 carbon atoms which may contain an oxygen atom or a sulfur atom; and q' represents 0 or 1.

In general formulae (ax3-r-1) to (ax3-r-3), A" is the same as those defined for A" in general formula (a2-r-1).

Examples of the alkyl group, alkoxy group, halogen atom, halogenated alkyl group, —COOR", —OC(═O)R" and hydroxyalkyl group for $Ra^{31}$ include the same groups as those described above in the explanation of $Ra'^{21}$ in the general formulae (a2-r-1) to (a2-r-7).

Specific examples of the groups represented by the aforementioned general formulae (ax3-r-1) to (ax3-r-3) are shown below.

[Chemical Formula 22]

(r-cr-1-1)
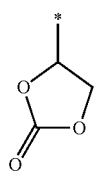

-continued
(r-cr-1-2)
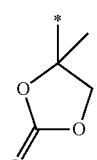
(r-cr-1-3)
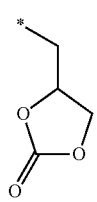
(r-cr-1-4)
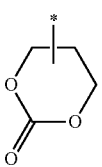
(r-cr-1-5)
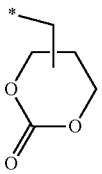
(r-cr-1-6)
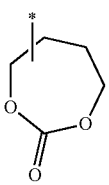
(r-cr-1-6)
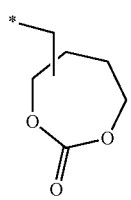
(r-cr-2-1)
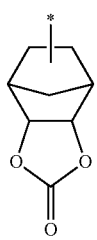
(r-cr-2-2)
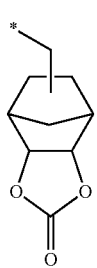
-continued
(r-cr-2-3)
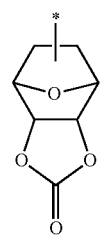
(r-cr-2-4)
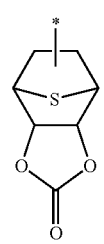
(r-cr-3-1)
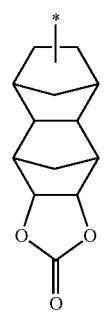
(r-cr-3-2)
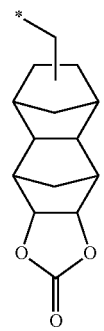
(r-cr-3-3)
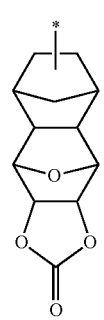

(r-cr-3-4)

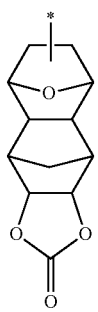

(r-cr-3-5)

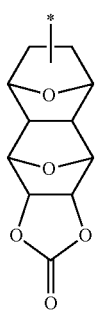

Among the above examples, as the lactone-containing cyclic group, a group represented by the general formula (a2-r-1) or (a2-r-2) is preferable, and a group represented by the chemical formula (r-1c-1-1) is more preferable.

As the structural unit (a2) contained in the component (A1), 1 kind of structural unit may be used, or 2 or more kinds thereof may be used.

When the component (A1) contains the structural unit (a2), the ratio of the structural unit (a2) based on the total of all structural units constituting the component (A1) is preferably 1 to 80 mol %, more preferably 5 to 70 mol %, still more preferably 10 to 65 mol %, and particularly preferably 10 to 60 mol %. When the ratio of the structural unit (a2) is at least as large as the lower limit of the above-mentioned range, the effect of containing the structural unit (a2) can be satisfactorily achieved. On the other hand, when the ratio of the structural unit (a2) is equal to or lower than the upper limit of the above-mentioned range, a good balance can be achieved with the other structural units, and various lithography properties such as DOF and CDU and pattern shape can be improved.

The component (A1) may have the following structural unit (a3) or structural unit (a4) other than the aforementioned structural units (a1) and (a2).

(Structural Unit (a3))

The structural unit (a3) is a structural unit containing a polar group-containing aliphatic hydrocarbon group (provided that the structural units that fall under the definition of structural units (a1) and (a2) are excluded).

When the component (A1) includes the structural unit (a3), it is presumed that the hydrophilicity of the component (A) is enhanced, thereby contributing to improvement in resolution.

Examples of the polar group include a hydroxy group, cyano group, carboxy group, or hydroxyalkyl group in which a part of the hydrogen atoms of the alkyl group have been substituted with fluorine atoms, and a hydroxy group is particularly preferable.

Examples of the aliphatic hydrocarbon group include linear or branched hydrocarbon groups (preferably alkylene groups) having 1 to 10 carbon atoms, and cyclic aliphatic hydrocarbon groups (cyclic groups). These cyclic groups may be monocyclic groups or polycyclic groups and can be selected appropriately from the multitude of groups that have been proposed for the resins of resist compositions designed for use with ArF excimer lasers. The cyclic group is preferably a polycyclic group, more preferably a polycyclic group having 7 to 30 carbon atoms.

Of the various possibilities, structural units derived from an acrylic ester that include an aliphatic polycyclic group that contains a hydroxy group, cyano group, carboxy group or a hydroxyalkyl group in which a part of the hydrogen atoms of the alkyl group have been substituted with fluorine atoms are more preferable. Examples of the polycyclic group include groups in which two or more hydrogen atoms have been removed from a bicycloalkane, tricycloalkane, tetracycloalkane or the like. Specific examples thereof include groups in which two or more hydrogen atoms have been removed from a polycycloalkane such as adamantane, norbornane, isobornane, tricyclodecane or tetracyclododecane. Of these polycyclic groups, a group in which two or more hydrogen atoms have been removed from adamantane, a group in which two or more hydrogen atoms have been removed from norbornane, and a group in which two or more hydrogen atoms have been removed from tetracyclododecane are industrially preferable.

As the structural unit (a3), there is no particular limitation as long as it is a structural unit containing a polar group-containing aliphatic hydrocarbon group, and an arbitrary structural unit may be used.

The structural unit (a3) is preferably a structural unit derived from an acrylic ester in which the hydrogen atom bonded to the carbon atom on the α-position may be substituted with a substituent and contains a polar group-containing aliphatic hydrocarbon group.

When the hydrocarbon group within the polar group-containing aliphatic hydrocarbon group is a linear or branched hydrocarbon group having 1 to 10 carbon atoms, the structural unit (a3) is preferably a structural unit derived from a hydroxyethyl ester of acrylic acid. On the other hand, when the hydrocarbon group is a polycyclic group, structural units represented by formulas (a3-1), (a3-2) and (a3-3) shown below respectively, are preferable.

[Chemical Formula 23]

(a3-1)

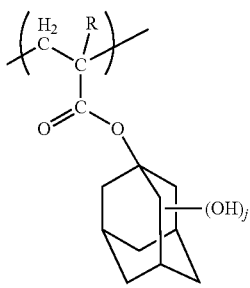

-continued

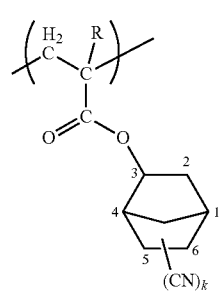
(a3-2)

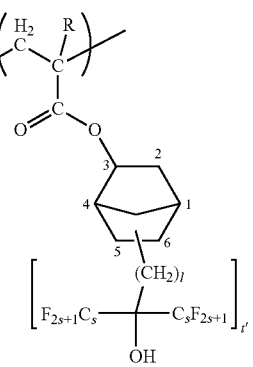
(a3-3)

In the formulas, R is the same as those defined above; j is an integer of 1 to 3; k is an integer of 1 to 3; t' is an integer of 1 to 3; l is an integer of 1 to 5; and s is an integer of 1 to 3.

In formula (a3-1), j is preferably 1 or 2, and more preferably 1. When j is 2, it is preferable that the hydroxy groups be bonded to the 3rd and 5th positions of the adamantyl group. When j is 1, it is preferable that the hydroxy group be bonded to the 3rd position of the adamantyl group.

j is preferably 1, and it is particularly preferable that the hydroxy group be bonded to the 3rd position of the adamantyl group.

In formula (a3-2), k is preferably 1. The cyano group is preferably bonded to the 5th or 6th position of the norbornyl group.

In formula (a3-3), t' is preferably 1. l is preferably 1. s is preferably 1. Further, it is preferable that a 2-norbornyl group or 3-norbornyl group be bonded to the terminal of the carboxy group of the acrylic acid. The fluorinated alkyl alcohol is preferably bonded to the 5th or 6th position of the norbornyl group.

As the structural unit (a3) contained in the component (A1), 1 kind of structural unit may be used, or 2 or more kinds thereof may be used.

The ratio of the structural unit (a3) within the component (A1) based on the total of all structural units constituting the resin component (A1) is preferably 5 to 50 mol %, more preferably 5 to 40 mol %, and still more preferably 5 to 25 mol %.

When the ratio of the structural unit (a3) is at least as large as the lower limit of the above-mentioned range, the effect of containing the structural unit (a3) can be satisfactorily achieved. On the other hand, when the ratio of the structural unit (a3) is equal to or lower than the upper limit of the above-mentioned range, a good balance can be easily achieved with the other structural units.

(Structural Unit (a4))

The structural unit (a4) is a structural unit containing an acid non-dissociable cyclic group. When the component (A1) includes the structural unit (a4), dry etching resistance of the resist pattern to be formed is improved. Further, the hydrophobicity of the component (A1) is further improved. Increase in the hydrophobicity contributes to improvement in terms of resolution, shape of the resist pattern and the like, particularly in an organic solvent developing process.

An "acid non-dissociable cyclic group" in the structural unit (a4) refers to a cyclic group which is not dissociated by the action of acid generated from the component (B) described later upon exposure, and remains in the structural unit.

As the structural unit (a4), a structural unit which is derived from an acrylate ester containing an acid non-dissociable aliphatic cyclic group is preferable. Examples of this cyclic group include the same groups as those described above in relation to the aforementioned structural unit (a1), and any of the multitude of conventional groups used within the resin component of resist compositions for ArF excimer lasers or KrF excimer lasers (and preferably for ArF excimer lasers) can be used.

In consideration of industrial availability and the like, at least one polycyclic group selected from amongst a tricyclodecyl group, adamantyl group, tetracyclododecyl group, isobornyl group, and norbornyl group is particularly preferable. These polycyclic groups may be substituted with a linear or branched alkyl group having 1 to 5 carbon atoms.

Specific examples of the structural unit (a4) include those having structures represented by general formulas (a4-1) to (a4-7) shown below.

[Chemical Formula 24]

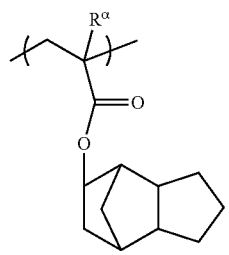
(a4-1)

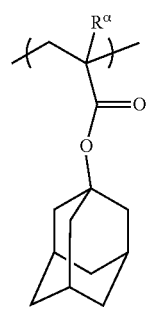
(a4-2)

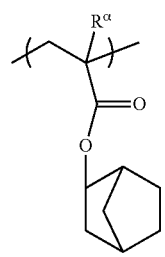
(a4-3)

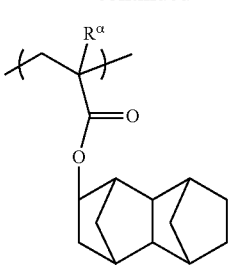

(a4-4)

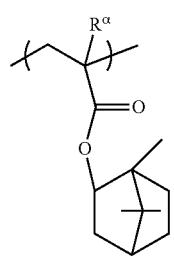

(a4-5)

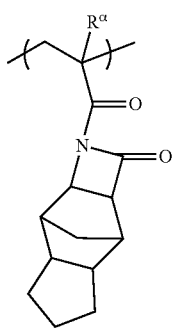

(a4-6)

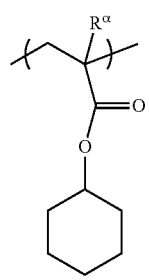

(a4-7)

In the formulae, $R^\alpha$ represents a hydrogen atom, a methyl group or a trifluoromethyl group.

As the structural unit (a4) contained in the component (A1), 1 kind of structural unit may be used, or 2 or more kinds thereof may be used.

When the structural unit (a4) is included in the component (A1), the ratio of the structural unit (a4) based on the total of all the structural units that constitute the component (A1) is preferably within the range from 1 to 30 mol %, and more preferably from 10 to 20 mol %.

The component (A1) is preferably a copolymer containing the structural units (a1) and (a2).

The component (A1) can be obtained by polymerizing the monomers deriving each of the structural units according to a known radical polymerization using a radical polymerization initiator such as azobisisobutyronitrile (AIBN) or dimethyl azobisisobutylate.

Furthermore, at the time of the polymerization, by using the component (A1) in combination with a chain transfer agent such as HS—$CH_2$—$CH_2$—$CH_2$—$C(CF_3)_2$—OH, —$C(CF_3)_2$—OH group may be introduced at the terminals of the component (A1). Such a copolymer to which a hydroxyalkyl group in which some of the hydrogen atoms of the alkyl group are substituted with fluorine atoms is introduced is effective in reducing developing defects and LER (line edge roughness: unevenness of the side walls of a line pattern).

In the present invention, the weight average molecular weight (Mw) (the polystyrene equivalent value determined by gel permeation chromatography) of the component (A1) is not particularly limited, but is preferably 1,000 to 50,000, more preferably 1,500 to 30,000, and most preferably 2,000 to 20,000. When the weight average molecular weight is equal to or lower than the upper limit of the above-mentioned range, the component exhibits a satisfactory solubility in a resist solvent to be used as resist. On the other hand, when the weight average molecular weight is at least as large as the lower limit of the above-mentioned range, dry etching resistance and the cross-sectional shape of the resist pattern becomes satisfactory.

As the component (A1), one kind may be used alone, or two or more kinds may be used in combination.

In the base component (A), the ratio of the component (A1) based on the total weight of the base component (A) is preferably 25% by weight or more, more preferably 50% by weight or more, still more preferably 75% by weight or more, and may be even 100% by weight. When the ratio of the component (A1) is 25% by weight or more, lithography properties are further improved.

In the present invention, as the component (A), one kind may be used, or two or more kinds may be used in combination.

In the present invention, the content of the component (A) may be appropriately adjusted depending on the thickness of the resist film to be formed, and the like.

<Acid Generator Component; Component (B)>

The resist composition according to the present invention may contain an acid generator component (B) (hereinafter, referred to as "component (B)) which generates an acid by exposure. As the component (B), there is no particular limitation, and those conventionally proposed as acid generators used in chemically amplified resist compositions can be used.

Examples of these acid generators are numerous, and include onium salt acid generators such as iodonium salts and sulfonium salts; oxime sulfonate acid generators; diazomethane acid generators such as bisalkyl or bisaryl sulfonyl diazomethanes and poly(bis-sulfonyl)diazomethanes; nitrobenzylsulfonate acid generators; iminosulfonate acid generators; and disulfone acid generators. Among these, it is preferable to use an onium salt acid generator.

As the onium salt acid generator, for example, a compound represented by general formula (b-1) below (hereafter, sometimes referred to as "component (b-1)"), a compound represented by general formula (b-2) below (hereafter, sometimes referred to as "component (b-2)") or a compound represented by general formula (b-3) below (hereafter, sometimes referred to as "component (b-3)") may be used.

[Chemical Formula 25]

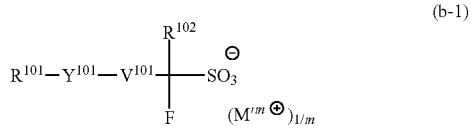

(b-1)

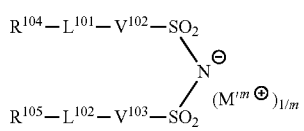
(b-2)

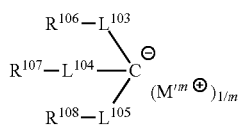
(b-3)

In the formulae, $R^{101}$ and $R^{104}$ to $R^{108}$ each independently represents a cyclic group which may have a substituent, a chain-like alkyl group which may have a substituent or a chain-like alkenyl group which may have a substituent; $R^{104}$ and $R^{105}$ may be mutually bonded to form a ring, $R^{106}$ and $R^{107}$ may be mutually bonded to form a ring, $R^{102}$ represents a fluorine atom or a fluorinated alkyl group having 1 to 5 carbon atoms; $Y^{101}$ represents a single bond or a divalent linking group containing an oxygen atom; $V^{101}$ to $V^{103}$ each independently represents a single bond, an alkylene group or a fluorinated alkylene group; $L^{101}$ and $L^{102}$ each independently represents a single bond or an oxygen atom; $L^{103}$ to $L^{105}$ each independently represents a single bond, —CO— or —SO$_2$—; and $M'^{m+}$ represents an organic cation having a valency of m.

{Anion Moiety}

Anion Moiety of Component (b-1)

In the formula (b-1), $R^{101}$ represents a cyclic group which may have a substituent, a chain-like alkyl group which may have a substituent or a chain-like alkenyl group which may have a substituent.

Cyclic Group for $R^{101}$ which May have a Substituent

The cyclic group is preferably a cyclic hydrocarbon group, and the cyclic hydrocarbon group may be either an aromatic hydrocarbon group or an aliphatic hydrocarbon group.

As the aromatic hydrocarbon group for $R^{101}$, aryl groups in which one hydrogen atom has been removed from an aromatic hydrocarbon ring described above in relation to the divalent aromatic hydrocarbon group for Va$^1$ in the formula (a1-1) or an aromatic compound containing two or more aromatic ring can be mentioned, and a phenyl group or a naphthyl group is preferable.

As the cyclic aliphatic hydrocarbon group for $R^{101}$, groups in which one hydrogen atom has been removed from a monocycloalkane or a polycycloalkane exemplified above in the explanation of the divalent aliphatic hydrocarbon group for Va$^1$ in the formula (a1-1) are exemplified. An adamantyl group or a norbornyl group is preferable.

Further, the cyclic hydrocarbon group for $R^{101}$ may contain a hetero atom like as a heterocycle, and specific examples thereof include lactone-containing cyclic groups respectively represented by the aforementioned general formulas (a2-r-1) to (a2-r-7), —SO$_2$— containing cyclic groups respectively represented by the aforementioned formulas (a5-r-1) to (a5-r-4), and other heterocyclic groups represented by (r-hr-1) to (r-hr-16).

[Chemical Formula 26]

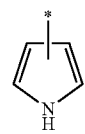 (r-hr-1)

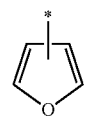 (r-hr-2)

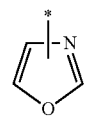 (r-hr-3)

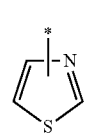 (r-hr-4)

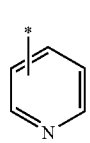 (r-hr-5)

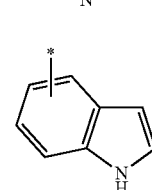 (r-hr-6)

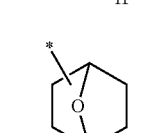 (r-hr-7)

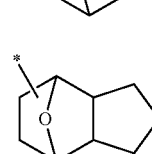 (r-hr-8)

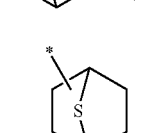 (r-hr-9)

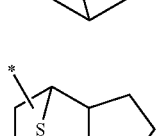 (r-hr-10)

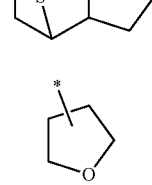 (r-hr-11)

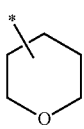 (r-hr-12)

 (r-hr-13)

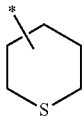 (r-hr-14)

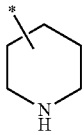 (r-hr-15)

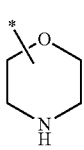 (r-hr-16)

As the substituent for the cyclic hydrocarbon group for $R^{101}$, an alkyl group, an alkoxy group, a halogen atom, a halogenated alkyl group, a hydroxy group, a carbonyl group, a nitro group or the like can be used.

The alkyl group as the substituent is preferably an alkyl group having 1 to 5 carbon atoms, and a methyl group, an ethyl group, a propyl group, an n-butyl group or a tert-butyl group is most preferable.

The alkoxy group as the substituent is preferably an alkoxy group having 1 to 5 carbon atoms, more preferably a methoxy group, an ethoxy group, an n-propoxy group, an iso-propoxy group, an n-butoxy group or a tert-butoxy group, and most preferably a methoxy group or an ethoxy group.

Examples of the halogen atom as the substituent include a fluorine atom, a chlorine atom, a bromine atom and an iodine atom, and a fluorine atom is preferable.

Example of the halogenated alkyl group as the substituent includes a group in which a part or all of the hydrogen atoms within an alkyl group having 1 to 5 carbon atoms (e.g., a methyl group, an ethyl group, a propyl group, an n-butyl group or a tert-butyl group) have been substituted with the aforementioned halogen atoms.

Chain-Like Alkyl Group for $R^{101}$ which May have a Substituent

The chain-like alkyl group for $R^{101}$ may be linear or branched.

The linear alkyl group preferably has 1 to 20 carbon atoms, more preferably 1 to 15 carbon atoms, and most preferably 1 to 10 carbon atoms. Specific examples include a methyl group, an ethyl group, a propyl group, a butyl group, a pentyl group, a hexyl group, a heptyl group, an octyl group, a nonyl group, a decyl group, an undecyl group, a dodecyl group, a tridecyl group, an isotridecyl group, a tetradecyl group, a pentadecyl group, a hexadecyl group, an isohexadecyl group, a heptadecyl group, an octadecyl group, a nonadecyl group, an icosyl group, a henicosyl group and a docosyl group.

The branched alkyl group preferably has 3 to 20 carbon atoms, more preferably 3 to 15 carbon atoms, and most preferably 3 to 10 carbon atoms. Specific examples include a 1-methylethyl group, a 1-methylpropyl group, a 2-methylpropyl group, a 1-methylbutyl group, a 2-methylbutyl group, a 3-methylbutyl group, a 1-ethylbutyl group, a 2-ethylbutyl group, a 1-methylpentyl group, a 2-methylpentyl group, a 3-methylpentyl group and a 4-methylpentyl group.

Chain-Like Alkenyl Group for $R^{101}$ which May have a Substituent

The chain-like alkenyl group for $R^{101}$ may be linear or branched, and preferably has 2 to 10 carbon atoms, more preferably 2 to 5 carbon atoms, still more preferably 2 to 4 carbon atoms, and most preferably 3 carbon atoms. Examples of linear alkenyl groups include a vinyl group, a propenyl group (an allyl group) and a butynyl group. Examples of branched alkenyl groups include a 1-methylpropenyl group and a 2-methylpropenyl group.

Among the above-mentioned examples, as the chain-like alkenyl group, a propenyl group is particularly preferable.

As the substituent for the chain-like alkyl group or alkenyl group for $R^{101}$, an alkoxy group, a halogen atom, a halogenated alkyl group, a hydroxy group, a carbonyl group, a nitro group, an amino group, a cyclic group for $R^{101}$ or the like can be used.

Among these examples, as $R^{101}$, a cyclic group which may have a substituent is preferable, and a cyclic hydrocarbon group which may have a substituent is more preferable. Specifically, a phenyl group, a naphthyl group, a group in which one or more hydrogen atoms have been removed from a polycycloalkane, a lactone-containing cyclic group represented by any one of the aforementioned formula (a2-r-1) to (a2-r-7), and an —$SO_2$— containing cyclic group represented by any one of the aforementioned formula (a5-r-1) to (a5-r-4).

In formula (b-1), $Y^{101}$ represents a single bond or a divalent linking group containing an oxygen atom.

In the case where $Y^{101}$ is a divalent linking group containing an oxygen atom, $Y^{101}$ may contain an atom other than an oxygen atom. Examples of atoms other than an oxygen atom include a carbon atom, a hydrogen atom, a sulfur atom and a nitrogen atom.

Examples of divalent linking groups containing an oxygen atom include non-hydrocarbon, oxygen atom-containing linking groups such as an oxygen atom (an ether bond; —O—), an ester bond (—C(=O)—O—), an oxycarbonyl group (—O—C(=O)—), an amido bond (—C(=O)—NH—), a carbonyl group (—C(=O)—) and a carbonate bond (—O—C(=O)—O—); and combinations of the aforementioned non-hydrocarbon, oxygen atom-containing linking groups with an alkylene group. Furthermore, the combinations may have a sulfonyl group (—$SO_2$—) bonded thereto. As the combination, the linking groups respectively represented by formulas (y-a1-1) to (y-a1-7) shown below can be mentioned.

[Chemical Formula 27]

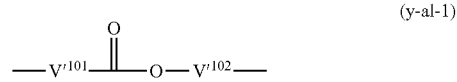 (y-a1-1)

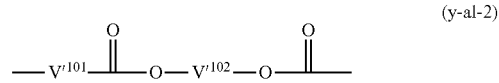 (y-a1-2)

-continued

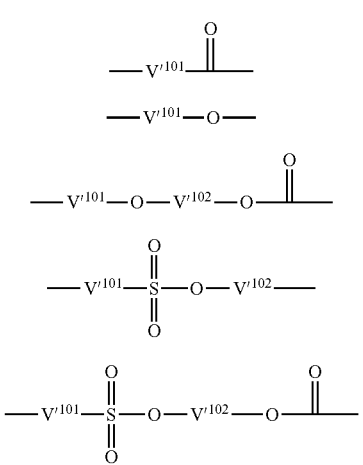

(y-al-3)
(y-al-4)
(y-al-5)
(y-al-6)
(y-al-7)

In the formulae, $V'^{101}$ represents a single bond or an alkylene group having 1 to 5 carbon atoms; $V'^{102}$ represents a divalent saturated hydrocarbon group having 1 to 30 carbon atoms.

The divalent saturated hydrocarbon group for $V'^{102}$ is preferably an alkylene group having 1 to 30 carbon atoms.

The alkylene group for $V'^{101}$ and $V'^{102}$ may be a linear alkylene group or a branched alkylene group, and a linear alkylene group is preferable.

Specific examples of the alkylene group for $V'^{101}$ and $V'^{102}$ include a methylene group [—$CH_2$—]; an alkylmethylene group, such as —$CH(CH_3)$—, —$CH(CH_2CH_3)$—, —$C(CH_3)_2$—, —$C(CH_3)(CH_2CH_3)$—, —$C(CH_3)(CH_2CH_2CH_3)$— and —$C(CH_2CH_3)_2$—; an ethylene group [—$CH_2CH_2$—]; an alkylethylene group, such as —$CH(CH_3)CH_2$—, —$CH(CH_3)CH(CH_3)$—, —$C(CH_3)_2CH_2$— and —$CH(CH_2CH_3)CH_2$—; a trimethylene group (n-propylene group) [—$CH_2CH_2CH_2$—]; an alkyltrimethylene group, such as —$CH(CH_3)CH_2CH_2$— and —$CH_2CH(CH_3)CH_2$—; a tetramethylene group [—$CH_2CH_2CH_2CH_2$—]; an alkyltetramethylene group, such as —$CH(CH_3)CH_2CH_2CH_2$—, —$CH_2CH(CH_3)CH_2CH_2$—; and a pentamethylene group [—$CH_2CH_2CH_2CH_2CH_2$—].

Further, a part of methylene group within the alkylene group for $V'^{101}$ and $V'^{102}$ may be substituted with a divalent aliphatic cyclic group having 5 to 10 carbon atoms. The aliphatic cyclic group is preferably a divalent group in which one hydrogen atom has been further removed from the cyclic aliphatic hydrocarbon group for $Ra'^3$ in the aforementioned formula (a1-r-1), and a cyclohexylene group, 1,5-adamantylene group or 2,6-adamantylene group is more preferable.

$Y^{101}$ is preferably a divalent linking group containing an ether bond or an ester bond, and linking groups respectively represented by the aforementioned formulas (y-a1-1) to (y-a1-5) are preferable.

In formula (b-1), $V^{101}$ represents a single bond, an alkylene group or a fluorinated alkylene group. The alkylene group and the fluorinated alkylene group for $V^{101}$ preferably have 1 to 4 carbon atoms. Examples of the fluorinated alkylene group for $V^{101}$ include a group in which part or all of the hydrogen atoms within the alkylene group for $V^{101}$ have been substituted with fluorine atoms. Among these examples, as $V^{101}$, a single bond or a fluorinated alkylene group having 1 to 4 carbon atoms is preferable.

In formula (b-1), $R^{102}$ represents a fluorine atom or a fluorinated alkyl group having 1 to 5 carbon atoms. $R^{102}$ is preferably a fluorine atom or a perfluoroalkyl group having 1 to 5 carbon atoms, and more preferably a fluorine atom.

As specific examples of anion moieties of the component (b-1), in the case where $Y^{101}$ represents a single bond, a fluorinated alkylsulfonate anion such as a trifluoromethanesulfonate anion or a perfluorobutanesulfonate anion can be mentioned; and in the case where $Y^{101}$ represents a divalent linking group containing an oxygen atom, anions represented by any one of formulae (an-1) to (an-3) shown below can be mentioned.

[Chemical Formula 28]

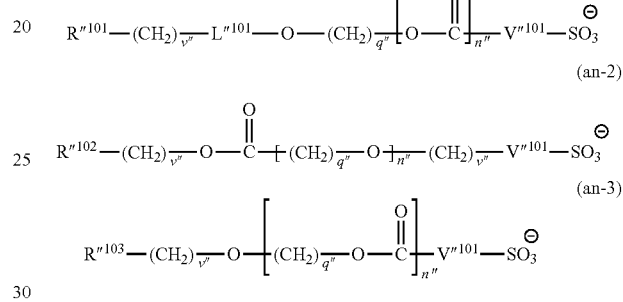

(an-1)
(an-2)
(an-3)

In the formulae, $R'''^{101}$ represents an aliphatic cyclic group which may have a substituent, a group represented by any one of the aforementioned formulae (r-hr-1) to (r-hr-6) or a chain-like alkyl group which may have a substituent; $R'''^{102}$ represents an aliphatic cyclic group which may have a substituent, a lactone-containing cyclic group represented by any one of the aforementioned formulae (a2-r-1) to (a2-r-7) or an —$SO_2$— containing cyclic group represented by any one of the aforementioned formulae (a5-r-1) to (a5-r-4); $R'''^{103}$ represents an aromatic cyclic group which may have a substituent, an aliphatic cyclic group which may have a substituent or a chain-like alkenyl group which may have a substituent; $V'''^{101}$ represents a fluorinated alkylene group; $L'''^{101}$ represents —$C(=O)$— or —$SO_2$—; $v''$ each independently represents an integer of 0 to 3; $q''$ each independently represents an integer of 1 to 20; and $n''$ represents 0 or 1.

As the aliphatic cyclic group for $R'''^{101}$, $R'''^{102}$ and $R'''^{103}$ which may have a substituent, the same groups as the cyclic aliphatic hydrocarbon group for $R^{101}$ described above are preferable. As the substituent, the same groups as the substituents which may substitute the cyclic aliphatic hydrocarbon group for $R^{101}$ described above can be mentioned.

As the aromatic cyclic group for $R'''^{103}$ which may have a substituent, the same groups as the aromatic hydrocarbon group for the cyclic hydrocarbon group represented by $R^{101}$ described above are preferable. As the substituent, the same groups as the substituent which may substitute the aromatic hydrocarbon group represented by $R^{101}$ can be mentioned.

As the chain-like alkyl group for $R'''^{101}$ which may have a substituent, the same groups as those described above for $R^{101}$ are preferable. As the chain-like alkenyl group for $R'''^{103}$ which may have a substituent, the same groups as those described above for $R^{101}$ are preferable. $V'''^{101}$ is preferably a fluorinated alkylene group having 1 to 3 carbon atoms, and particularly preferably —$CF_2$—, —$CF_2CF_2$—, —$CHFCF_2$—, —$CF(CF_3)CF_2$— or —$CH(CF)CF_2$—.

Anion Moiety of Component (b-2)

In formula (b-2), $R^{104}$ and $R^{105}$ each independently represents a cyclic group which may have a substituent, a chain-like alkyl group which may have a substituent or a chain-like alkenyl group which may have a substituent, and example thereof includes the same groups as defined for $R^{101}$ in formula (b-1). $R^{104}$ and $R^{105}$ may be mutually bonded to form a ring.

As $R^{104}$ and $R^{105}$, a chain-like alkyl group which may have a substituent is preferable, and a linear or branched alkyl group or a linear or branched fluorinated alkyl group is more preferable.

The chain-like alkyl group preferably has 1 to 10 carbon atoms, more preferably 1 to 7 carbon atoms, and still more preferably 1 to 3 carbon atoms. The smaller the number of carbon atoms of the chain-like alkyl group for $R^{104}$ and $R^{105}$ in the range described above, the more it is preferable because the solubility in a resist solvent is improved. Further, in the chain-like alkyl group for $R^{104}$ and $R^{105}$, it is preferable that the number of hydrogen atoms substituted with fluorine atoms is as large as possible because the acid strength increases and the transparency to high energy radiation of 200 nm or less or electron beam is improved. The ratio of fluorine atoms in the chain-like alkyl group, that is, the fluorination ratio is preferably from 70 to 100%, more preferably from 90 to 100%, and it is most preferable that the chain-like alkyl group be a perfluoroalkyl group in which all hydrogen atoms are substituted with fluorine atoms.

In formula (b-2), $V^{102}$ and $V^{103}$ each independently represents a single bond, an alkylene group or a fluorinated alkylene group, and is the same as those defined for $V^{101}$ in formula (b-1).

In formula (b-2), $L^{101}$ and $L^{102}$ each independently represents a single bond or an oxygen atom.

Anion Moiety of Component (b-3)

In formula (b-3), $R^{106}$ to $R^{108}$ each independently represents a cyclic group which may have a substituent, a chain-like alkyl group which may have a substituent or a chain-like alkenyl group which may have a substituent, and is the same as those defined for $R^{101}$ in formula (b-1).

$L^{103}$ to $L^{105}$ each independently represents a single bond, —CO— or —SO$_2$—.

{Cation Moiety}

In formulae (b-1), (b-2) and (b-3), $M^{m+}$ represents an organic cation having a valency of m, preferably a sulfonium cation or an iodonium cation, and particularly preferably a cation represented by any one of formulae (ca-1) to (ca-4) shown below.

[Chemical Formula 29]

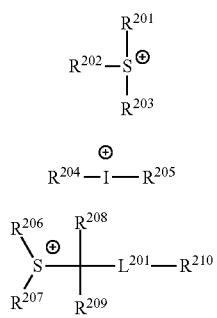

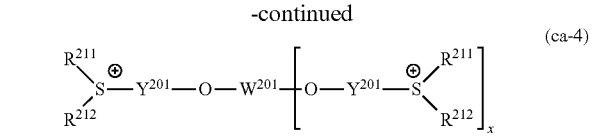

In the formulae, $R^{201}$ to $R^{207}$, $R^{211}$ and $R^{212}$ independently represents an aryl group which may have a substituent, an alkyl group which may have a substituent, or an alkenyl group which may have a substituent, $R^{201}$ to $R^{203}$, $R^{206}$ and $R^{207}$, or $R^{211}$ and $R^{212}$ may be mutually bonded to form a ring with the sulfur atom in the formula; $R^{208}$ and $R^{209}$ each independently represents a hydrogen atom or an alkyl group having 1 to 5 carbon atoms; $R^{210}$ represents an aryl group which may have a substituent, an alkyl group which may have a substituent, an alkenyl group which may have a substituent or an —SO$_2$— containing cyclic group which may have a substituent; $L^{201}$ represents —C(=O)— or —C(=O)—O—; $Y^{201}$ each independently represents an arylene group, an alkylene group or an alkenylene group; x represents 1 or 2; and $W^{201}$ represents a linking group having a valency of (x+1).

As the aryl group for $R^{201}$ to $R^{207}$, $R^{211}$ and $R^{212}$, an unsubstituted aryl group having 6 to 20 carbon atoms can be mentioned, and a phenyl group or a naphthyl group is preferable.

The alkyl group for $R^{201}$ to $R^{207}$, $R^{211}$ and $R^{212}$ is preferably a chain-like or cyclic alkyl group having 1 to 30 carbon atoms.

The alkenyl group for $R^{201}$ to $R^{207}$, $R^{211}$ and $R^{212}$ preferably has 2 to 10 carbon atoms.

Examples of the substituent which $R^{201}$ to $R^{207}$ and $R^{210}$ to $R^{212}$ may have include an alkyl group, a halogen atom, a halogenated alkyl group, a carbonyl group, a cyano group, an amino group, an aryl group, an arylthio group and groups respectively represented by formulae (ca-r-1) to (ca-r-7) shown below.

The aryl group within the arylthio group as the substituent is the same as those defined for $R^{101}$, and specific examples include a phenylthio group and a biphenylthio group.

[Chemical Formula 30]

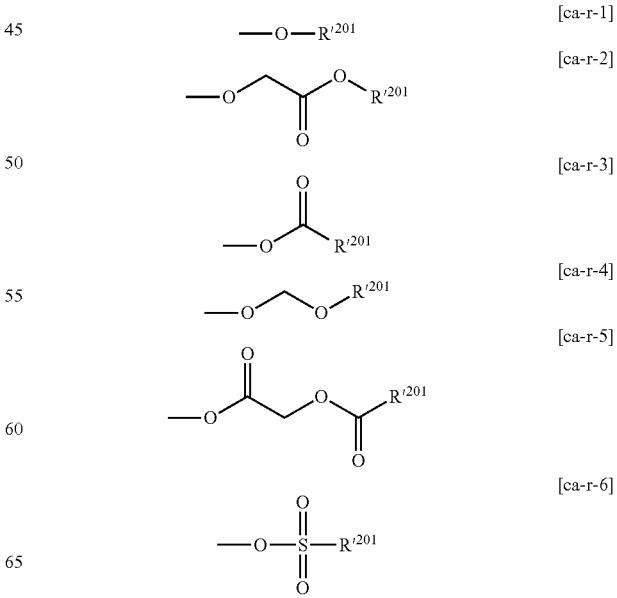

-continued

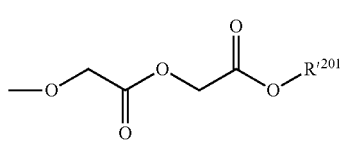

(ca-r-7)

In the formulae, $R'^{201}$ each independently represents a hydrogen atom, a cyclic group which may have a substituent, a chain-like alkyl group which may have a substituent or a chain-like alkenyl group which may have a substituent.

As the cyclic group which may have a substituent, the chain-like alkyl group which may have a substituent and the chain-like alkenyl group which may have a substituent for $R'^{201}$, the same groups as those described above for $R'^{101}$ in the formula (b-1) can be mentioned. As the cyclic group which may have a substituent and chain-like alkyl group which may have a substituent, the same groups as those described above for the acid dissociable group represented by the aforementioned formula (a1-r-2) can be also mentioned.

When $R^{201}$ to $R^{203}$, $R^{206}$, $R^{207}$, $R^{211}$ and $R^{212}$ are mutually bonded to form a ring with the sulfur atom in the formula, these groups may be mutually bonded via a hetero atom such as a sulfur atom, an oxygen atom or a nitrogen atom, or a functional group such as a carbonyl group, —SO—, —SO$_2$—, —SO$_3$—, —COO—, —CONH— or —N(R$_N$)— (wherein R$_N$ represents an alkyl group having 1 to 5 carbon atoms). As a ring to be formed, a ring containing the sulfur atom of the formula in the skeleton thereof is preferably a 3 to 10-membered ring, and particularly preferably a 5 to 7-membered ring. Specific examples of the ring formed include a thiophene ring, a thiazole ring, a benzothiophene ring, a thianthrene ring, a benzothiophene ring, a dibenzothiophene ring, a 9H-thioxanthene ring, a thioxanthone ring, a thianthrene ring, a phenoxathiin ring, a tetrahydrothiophenium ring, and a tetrahydrothiopyranium ring.

$R^{208}$ and $R^{209}$ each independently represents a hydrogen atom or an alkyl group having 1 to 5 carbon atoms, preferably a hydrogen atom or an alkyl group having 1 to 3 carbon atoms, and when $R^{208}$ and $R^{209}$ each represents an alkyl group, $R^{208}$ and $R^{209}$ may be mutually bonded to form a ring.

$R^{210}$ represents an aryl group which may have a substituent, an alkyl group which may have a substituent, an alkenyl group which may have a substituent, or an —SO$_2$— containing cyclic group which may have a substituent.

Examples of the aryl group for $R^{210}$ include an unsubstituted aryl group having 6 to 20 carbon atoms, and a phenyl group or a naphthyl group is preferable.

As the alkyl group for $R^{210}$, a chain-like or cyclic alkyl group having 1 to 30 carbon atoms is preferable.

The alkenyl group for $R^{210}$ preferably has 2 to 10 carbon atoms.

As the —SO$_2$— containing cyclic group for $R^{210}$ which may have a substituent, the same "—SO$_2$— containing cyclic groups" as those described above for Ra$^{21}$ in the aforementioned general formula (a2-1) can be mentioned, and the group represented by the aforementioned general formula (a5-r-1) is preferable.

Each $Y^{201}$ independently represents an arylene group, an alkylene group or an alkenylene group.

Examples of the arylene group for $Y^{201}$ include groups in which one hydrogen atom has been removed from an aryl group given as an example of the aromatic hydrocarbon group for $R^{101}$ in the aforementioned formula (b-1).

The alkylene group and the alkenylene group for $Y^{201}$ is the same as those defined for the aliphatic hydrocarbon group as the divalent hydrocarbon group represented by Va$^1$ in the aforementioned general formula (a1-1).

In the formula (ca-4), x represents 1 or 2.

$W^{201}$ represents a linking group having a valency of (x+1), i.e., a divalent or trivalent linking group.

As the divalent linking group for $W^{201}$, a divalent hydrocarbon group which may have a substituent is preferable, and as examples thereof, the same hydrocarbon groups as those described above for Ya$^{21}$ in the general formula (a2-1) can be mentioned. The divalent linking group for $W^{201}$ may be linear, branched or cyclic, and cyclic is preferable. Among these, an arylene group having two carbonyl groups, each bonded to the terminal thereof is preferable. Examples of the arylene group include a phenylene group and a naphthylene group, and a phenylene group is particularly preferable.

As the trivalent linking group for $W^{201}$, a group in which one hydrogen atom has been removed from the aforementioned divalent linking group for $W^{201}$ and a group in which the divalent linking group has been bonded to another divalent linking group can be mentioned. The trivalent linking group for $W^{201}$ is preferably a group in which 2 carbonyl groups are bonded to an arylene group.

Specific examples of preferable cations represented by formula (ca-1) include cations respectively represented by formulae (ca-1-1) to (ca-1-63) shown below.

[Chemical Formula 31]

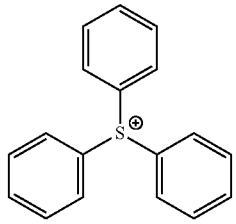

(ca-1-1)

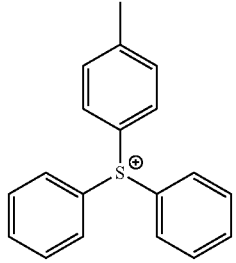

(ca-1-2)

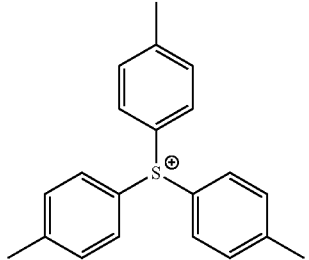

(ca-1-3)

-continued
(ca-1-4)
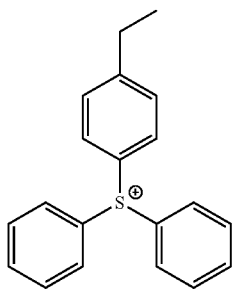
(ca-1-5)
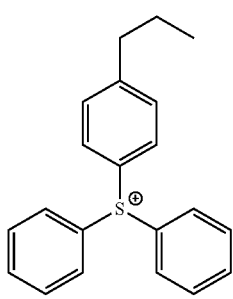
(ca-1-6)
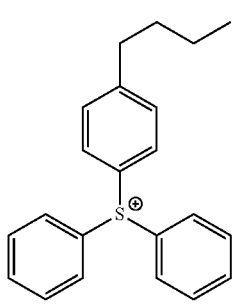
(ca-1-7)
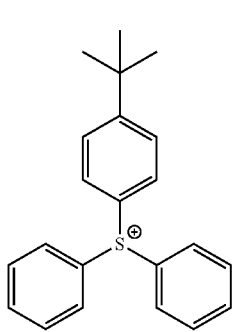
(ca-1-8)
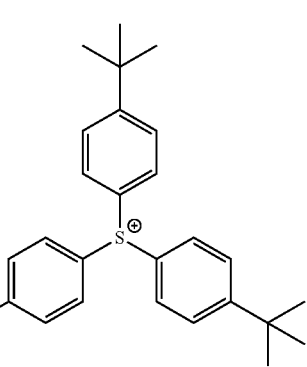
-continued
(ca-1-9)
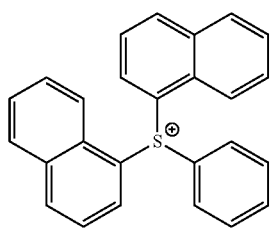
(ca-1-10)
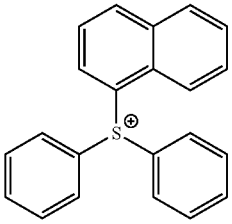
(ca-1-11)
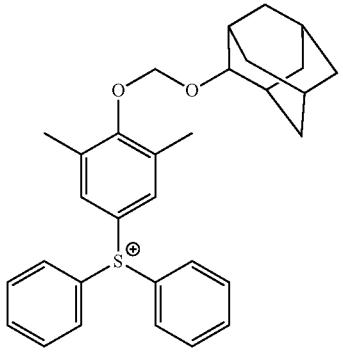
(ca-1-12)
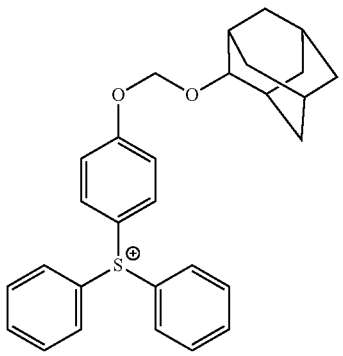
(ca-1-13)
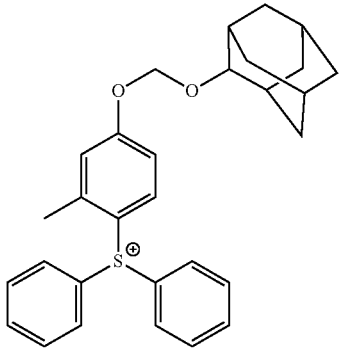

(ca-1-14)
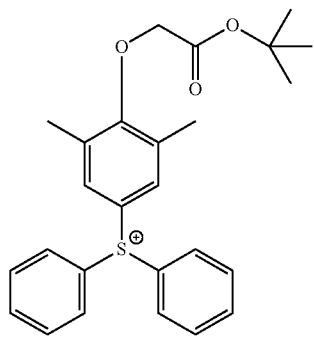
(ca-1-18)
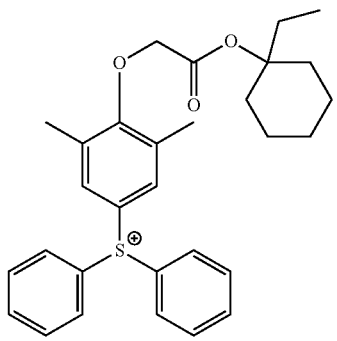
(ca-1-15)
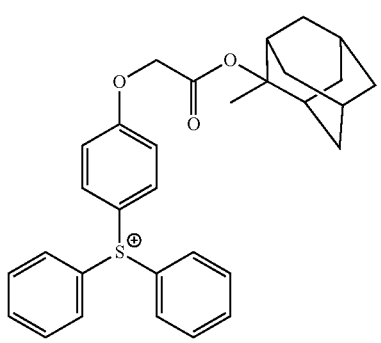
(ca-1-19)
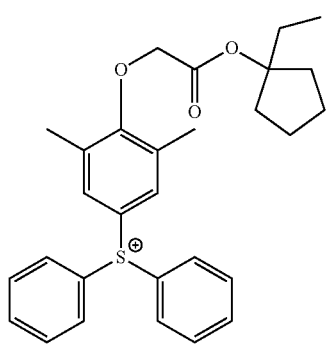
(ca-1-16)
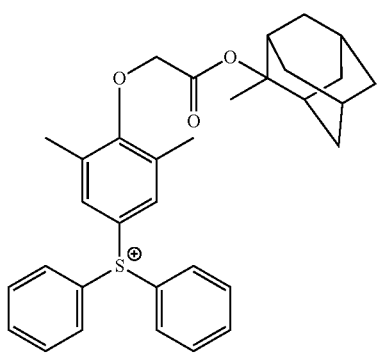
(ca-1-20)
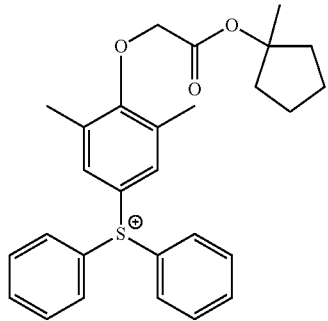
[Chemical Formula 32]
(ca-1-17)
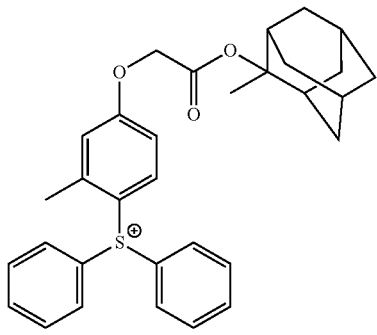
(ca-1-21)
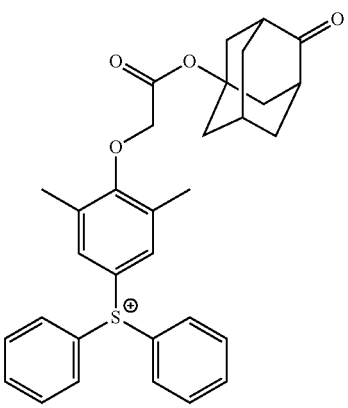

(ca-1-22)
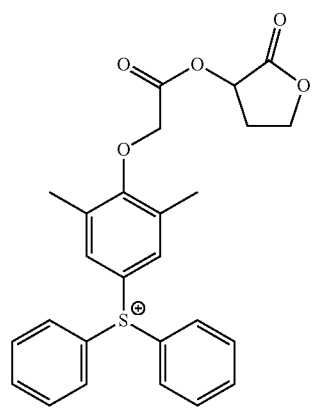
(ca-1-23)
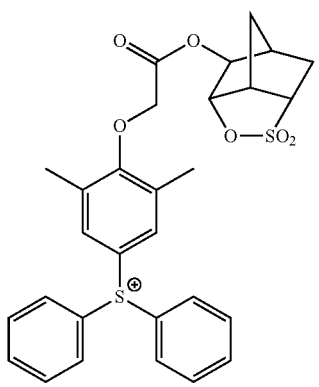
(ca-1-24)
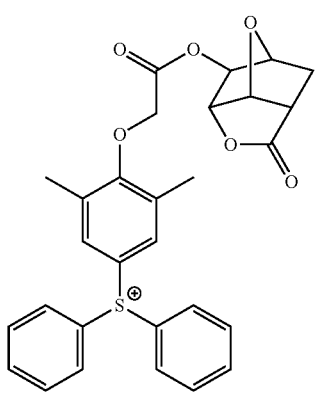
(ca-1-25)
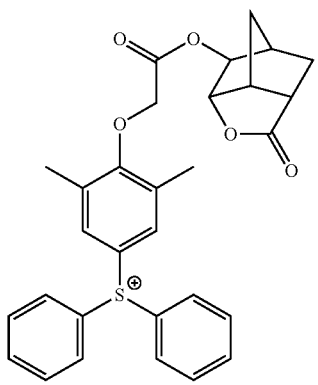
(ca-1-26)
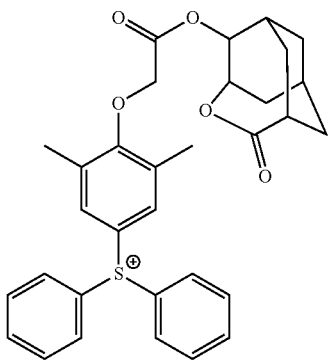
(ca-1-27)
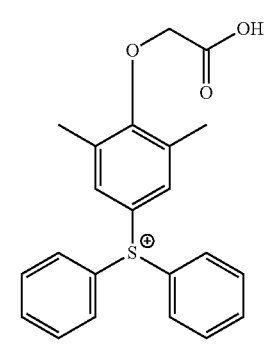
(ca-1-28)
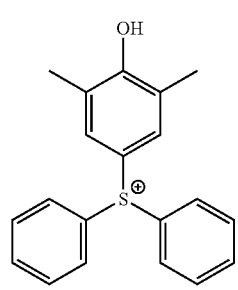
(ca-1-29)
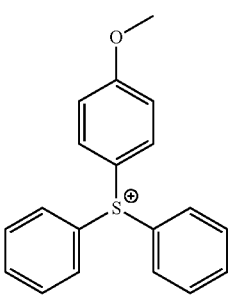
(ca-1-30)
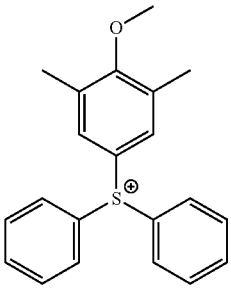

(ca-1-31)
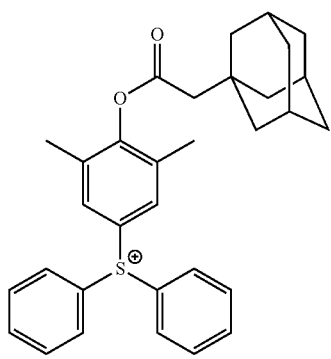
(ca-1-32)
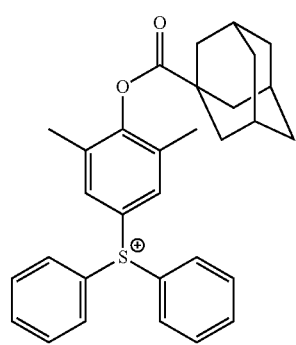
(ca-1-33)
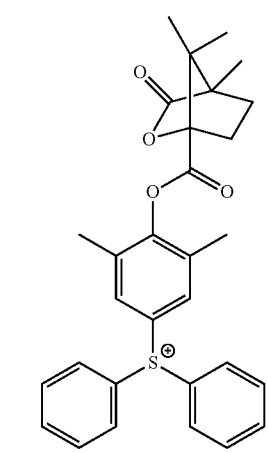
[Chemical Formula 33]
(ca-1-34)
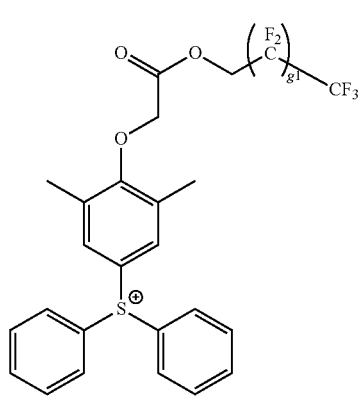
(ca-1-35)
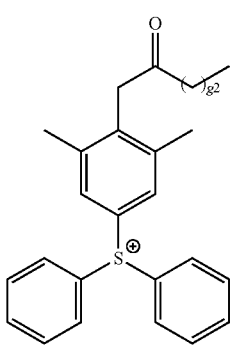
(ca-1-36)
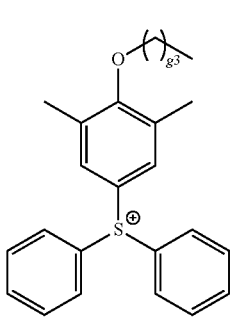
(ca-1-37)
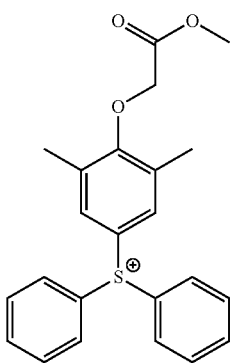
(ca-1-38)
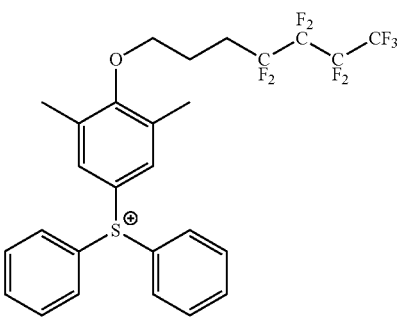

In the formulae, g1, g2 and g3 represent repeating numbers, wherein g1 is an integer of 1 to 5, g2 is an integer of 0 to 20, and g3 is an integer of 0 to 20.

[Chemical Formula 34]

-continued
(ca-1-51)
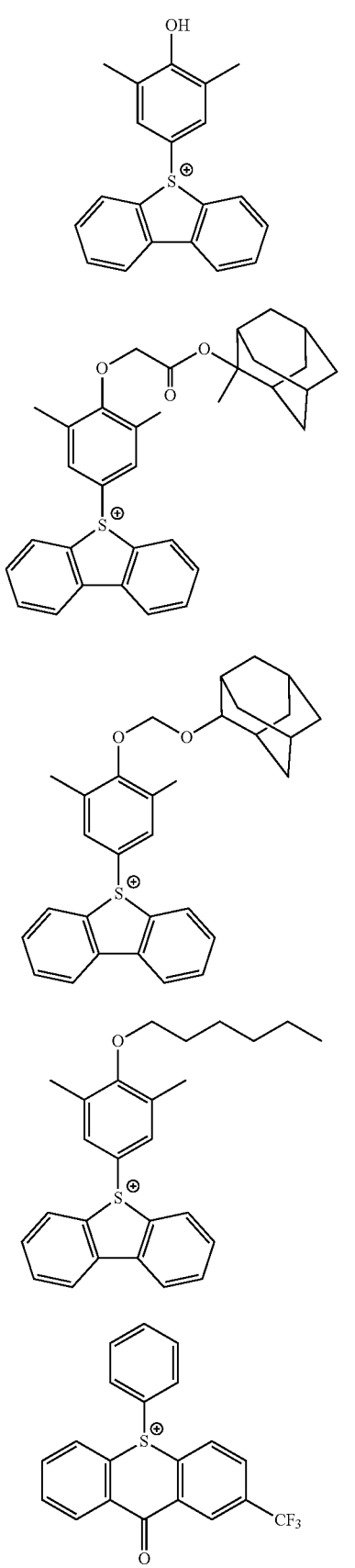
(ca-1-52)
(ca-1-53)
(ca-1-54)
(ca-1-55)
-continued
(ca-1-56)
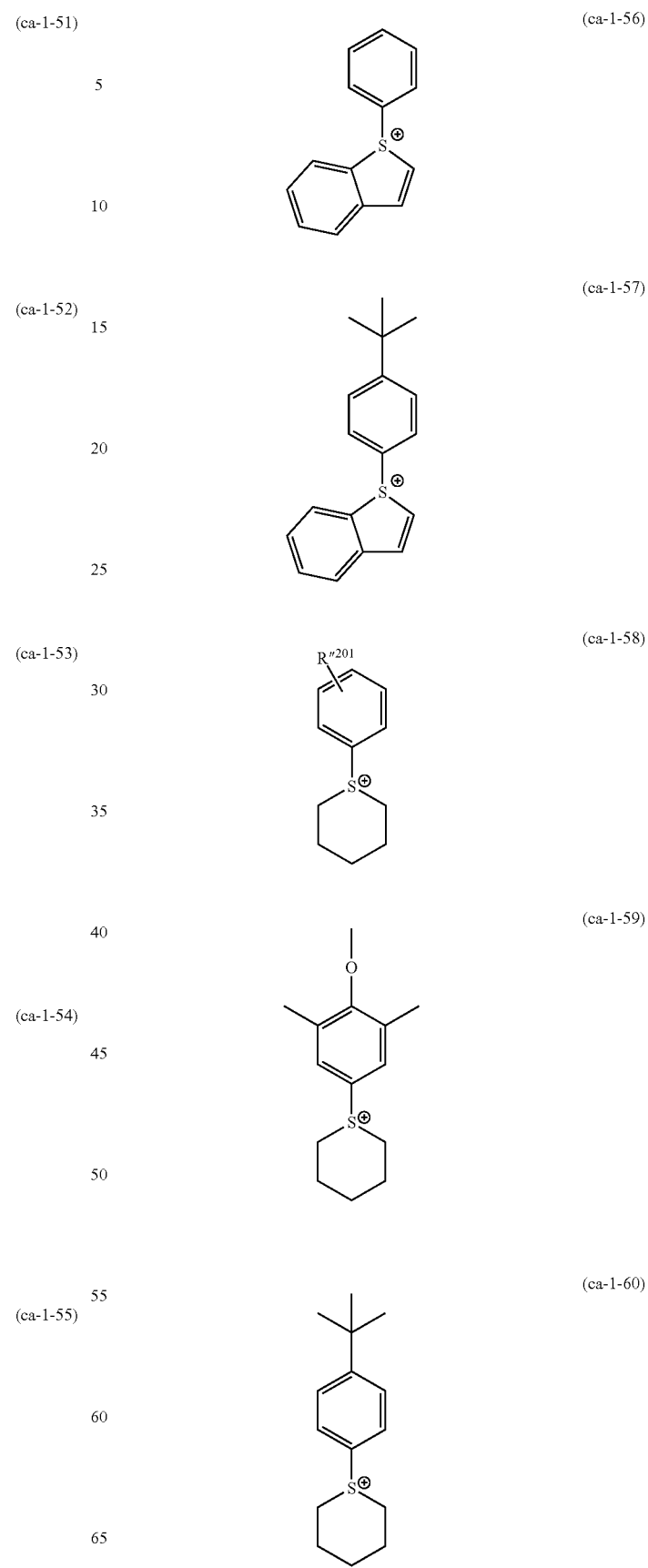
(ca-1-57)
(ca-1-58)
(ca-1-59)
(ca-1-60)

-continued (ca-1-61)

(ca-1-62)

(ca-1-63)

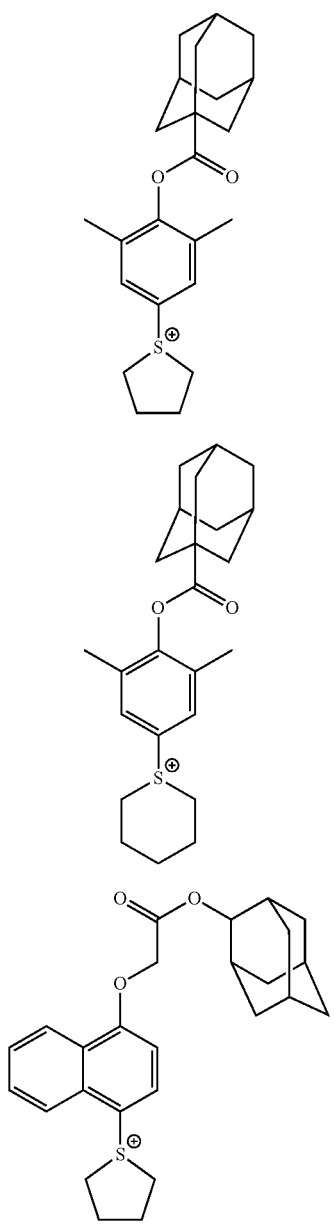

In the formulae, $R''^{201}$ represents a hydrogen atom or a substituent, and as the substituent, the same groups as those described above as the substituents which $R^{201}$ to $R^{207}$ and $R^{210}$ to $R^{212}$ may have can be mentioned.

Specific examples of preferable cations represented by formula (ca-3) include cations respectively represented by formulae (ca-3-1) to (ca-3-6) shown below.

[Chemical Formula 35]

(ca-3-1)

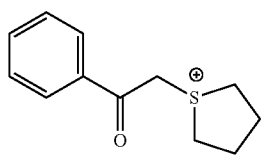

-continued (ca-3-2)

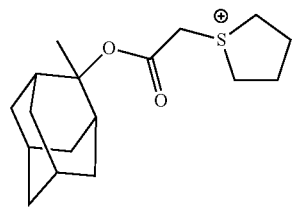

(ca-3-3)

(ca-3-4)

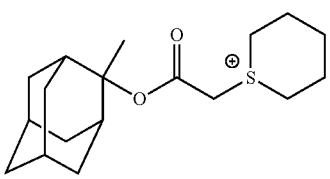

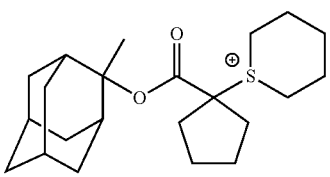

(ca-3-5)

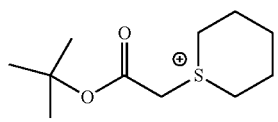

(ca-3-6)

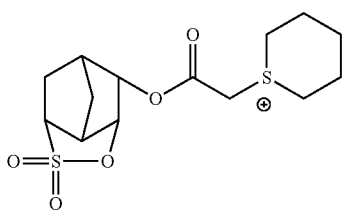

Specific examples of preferable cations represented by formula (ca-4) include cations respectively represented by formulae (ca-4-1) and (ca-4-2) shown below.

[Chemical Formula 36]

(ca-4-1)

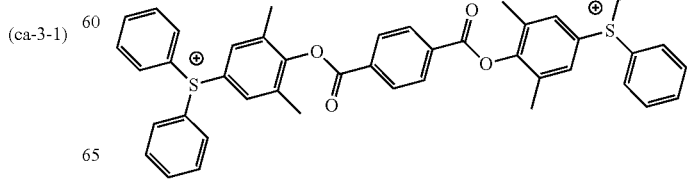

(ca-4-2)

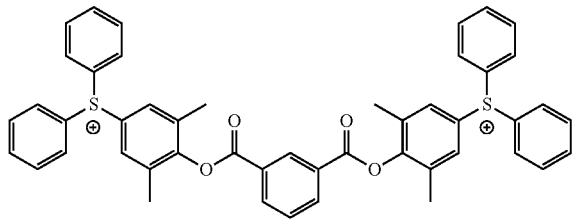

As the component (B), one kind of the above-described acid generators may be used alone, or two or more kinds thereof may be used in combination.

When the resist composition of the present invention contains the component (B), the content of the component (B) relative to 100 parts by weight of the component (A) is preferably within a range from 0.5 to 60 parts by weight, more preferably from 1 to 50 parts by weight, and still more preferably from 1 to 40 parts by weight. When the content of the component (B) is within the above-mentioned range, formation of a pattern can be satisfactorily performed. Further, by virtue of the above-mentioned range, when each of the components of the resist composition is dissolved in an organic solvent, a uniform solution can be obtained and the storage stability becomes satisfactory.

<Acid Diffusion Control Agent Component: Component (D)>

The resist composition according to the present invention may contain an acid diffusion control agent (hereinafter, referred to as "component (D)" in some cases) in addition to component (A) or in addition to component (A) and component (B).

The component (D) functions as a quencher (acid diffusion control agent) which traps the acid generated from the component (B) and the like upon exposure.

In the present invention, the component (D) may be a photodecomposable base (D1) (hereafter, referred to as "component (D1)") which is decomposed upon exposure and then loses the ability of controlling of acid diffusion, or a nitrogen-containing organic compound (D2) (hereafter, referred to as "component (D2)") which does not fall under the definition of component (D1).

[Component (D1)]

When a resist pattern is formed using a resist composition containing the component (D1), the contrast between exposed portions and unexposed portions is improved.

The component (D1) is not particularly limited, as long as it is decomposed upon exposure and then loses the ability of controlling of acid diffusion. As the component (D1), at least one compound selected from the group consisting of a compound represented by general formula (d1-1) shown below (hereafter, referred to as "component (d1-1)"), a compound represented by general formula (d1-2) shown below (hereafter, referred to as "component (d1-2)") and a compound represented by general formula (d1-3) shown below (hereafter, referred to as "component (d1-3)") is preferably used.

At exposed portions, the components (d1-1) to (d1-3) are decomposed and then lose the ability of controlling of acid diffusion (i.e., basicity), and therefore the components (d1-1) to (d1-3) cannot function as a quencher, whereas at unexposed portions, the components (d1-1) to (d1-3) functions as a quencher.

[Chemical Formula 37]

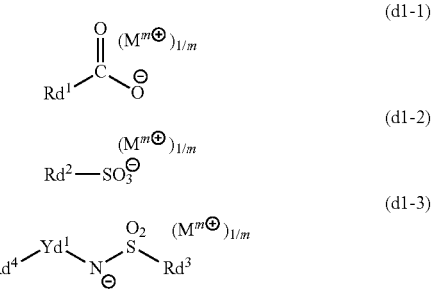

In the formulae, $Rd^1$ to $Rd^4$ represent a cyclic group which may have a substituent, a chain-like alkyl group which may have a substituent or a chain-like alkenyl group which may have a substituent, provided that, the carbon atom adjacent to the sulfur atom within the $Rd^2$ in the formula (d1-2) does not have more than two fluorine atoms bonded thereto; $Yd^1$ represents a single bond or a divalent linking group; and $M^{m+}$ each independently represents an organic cation having a valency of m.

{Component (d1-1)}

Anion Moiety

In formula (d1-1), $Rd^1$ represents a cyclic group which may have a substituent, a chain-like alkyl group which may have a substituent or a chain-like alkenyl group which may have a substituent, and is the same groups as those defined above for $R^{101}$.

Among these, as the group for $Rd^1$, an aromatic hydrocarbon group which may have a substituent, an aliphatic cyclic group which may have a substituent and a chain-like hydrocarbon group which may have a substituent are preferable, and an aromatic hydrocarbon group which may have a substituent and an aliphatic cyclic group which may have a substituent are more preferable. Examples of the substituent which these groups may have preferably include a hydroxy group, an oxygen atom, a fluorine atom, or a fluorinated alkyl group.

The aromatic hydrocarbon group is more preferably a phenyl group or a naphthyl group.

Examples of the aliphatic cyclic group preferably include groups in which one or more hydrogen atoms have been removed from a polycycloalkane such as adamantane, norbornane, isobornane, tricyclodecane or tetracyclododecane.

As the chain-like hydrocarbon group, a chain-like alkyl group is preferable. The chain-like alkyl group preferably has 1 to 10 carbon atoms, and specific examples thereof include a linear alkyl group such as a methyl group, an ethyl group, a propyl group, a butyl group, a pentyl group, a hexyl group, a heptyl group, an octyl group, a nonyl or a decyl group, and a branched alkyl group such as a 1-methylethyl group, a 1-methylpropyl group, a 2-methylpropyl group, a 1-methylbutyl group, a 2-methylbutyl group, a 3-methylbutyl group, a 1-ethylbutyl group, a 2-ethylbutyl group, a 1-methylpentyl group, a 2-methylpentyl group, a 3-methylpentyl group or a 4-methylpentyl group.

In the case where the chain-like alkyl group is a fluorinated alkyl group having a fluorine atom or a fluorinated alkyl group as a substituent, the fluorinated alkyl group preferably has 1 to 11 carbon atoms, more preferably 1 to 8 carbon atoms, and still more preferably 1 to 4 carbon atoms. The fluorinated alkyl group may contain an atom other than a fluorine atom. Examples of the atom other than a fluorine atom include an oxygen atom, a carbon atom, a hydrogen atom, a sulfur atom and a nitrogen atom.

As $Rd^1$, a fluorinated alkyl group in which part or all of the hydrogen atoms constituting a linear alkyl group have been substituted with fluorine atom(s) is preferable, and a fluorinated alkyl group in which all of the hydrogen atoms constituting a linear alkyl group have been substituted with fluorine atoms (i.e., a linear perfluoroalkyl group) is more preferable.

Specific examples of preferable anion moieties for the component (d1-1) are shown below.

[Chemical Formula 38]

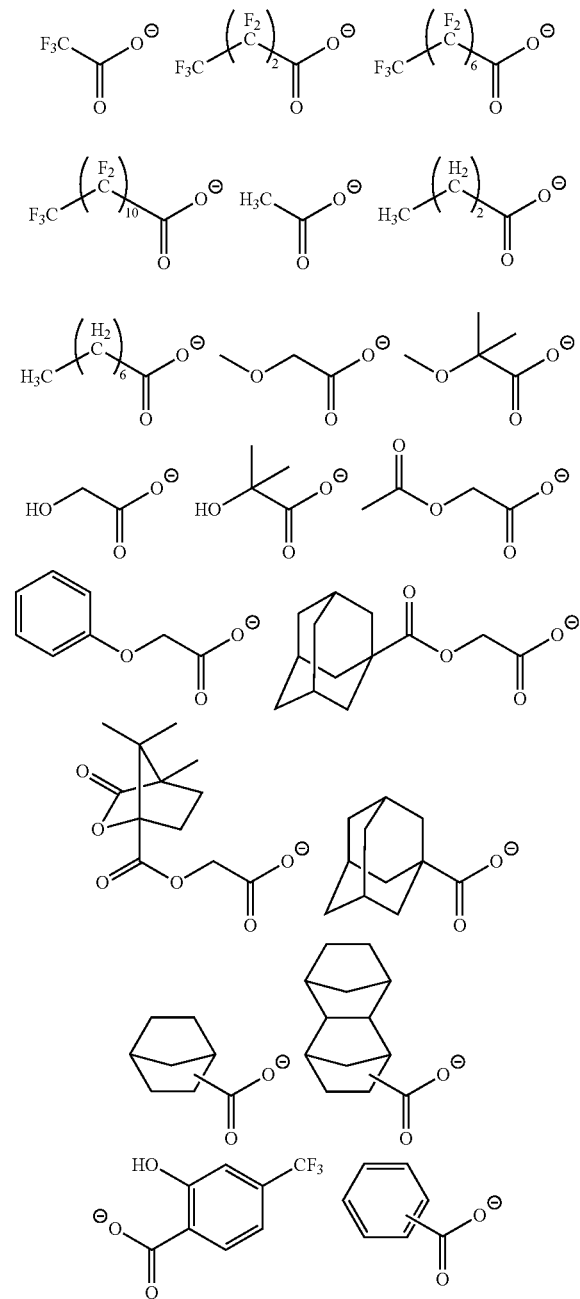

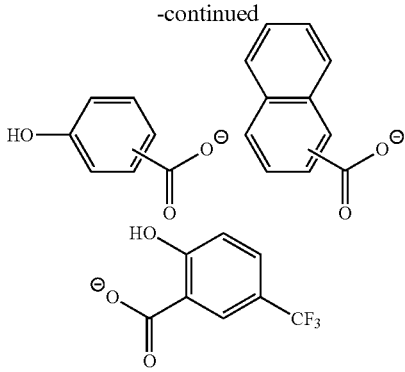

Cation Moiety

In formula (d1-1), $M^{m+}$ represents an organic cation having a valency of m.

The organic cation for $M^{m+}$ is not particularly limited, and examples thereof include the same cation moieties as those respectively represented by formulae (ca-1) to (ca-4) shown below, and cation moieties respectively represented by formulae (ca-1-1) to (ca-1-63) shown below are preferable.

As the component (d1-1), one kind of compound may be used, or two or more kinds of compounds may be used in combination.

{Component (d1-2)}

Anion Moiety

In formula (d1-2), $Rd^2$ represents a cyclic group which may have a substituent, a chain-like alkyl group which may have a substituent or a chain-like alkenyl group which may have a substituent, and is the same groups as those defined above for $R^{101}$.

However, the carbon atom adjacent to the sulfur atom within $Rd^2$ group has no fluorine atom bonded thereto (i.e., the carbon atom adjacent to the sulfur atom within $Rd^2$ group does not substituted with a fluorine atom). As a result, the anion of the component (d1-2) becomes an appropriately weak acid anion, thereby improving the quenching ability of the component (D).

As $Rd^2$, an aliphatic cyclic group which may have a substituent is preferable, and a group in which one or more hydrogen atoms have been removed from adamantane, norbornane, isobornane, tricyclodecane, tetracyclododecane or the like (which may have a substituent) or a group in which one or more hydrogen atoms have been removed from camphor or the like is more preferable.

The hydrocarbon group for $Rd^2$ may have a substituent. As the substituent, the same groups as those described above for the substituents which the hydrocarbon group (e.g., aromatic hydrocarbon group, aliphatic hydrocarbon group) for $Rd^1$ in the formula (d1-1) may have can be mentioned.

Specific examples of preferable anion moieties for the component (d1-2) are shown below.

[Chemical Formula 39]

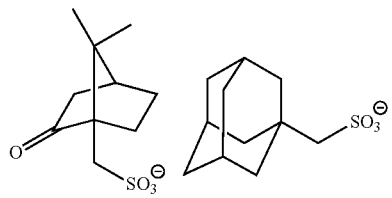

-continued

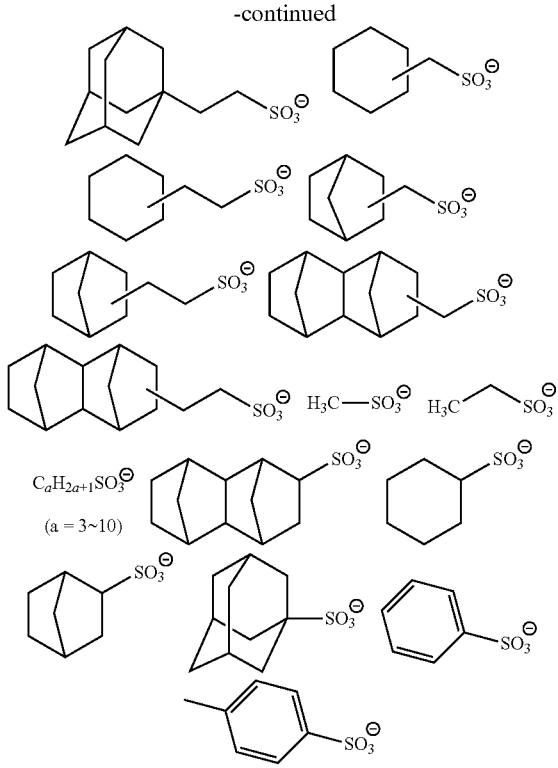

Cation Moiety

In formula (d1-2), $M^{m+}$ is an organic cation having a valency of m, and is the same as those defined for $M^{m+}$ in the aforementioned formula (d1-1).

As the component (d1-2), one kind of compound may be used, or two or more kinds of compounds may be used in combination.

{Component (d1-3)}
Anion Moiety

In formula (d1-3), $Rd^3$ represents a cyclic group which may have a substituent, a chain-like alkyl group which may have a substituent or a chain-like alkenyl group which may have a substituent, and is the same groups as those defined above for $R^{101}$, and a cyclic group containing a fluorine atom, a chain-like alkyl group or a chain-like alkenyl group is preferable. Among these, a fluorinated alkyl group is preferable, and the same fluorinated alkyl groups as those described above for Rd1 are more preferable.

In formula (d1-3), $Rd^4$ represents a cyclic group which may have a substituent, a chain-like alkyl group which may have a substituent or a chain-like alkenyl group which may have a substituent, and is the same groups as those defined above for $R^{101}$.

Among these, an alkyl group which may have substituent, an alkoxy group which may have substituent, an alkenyl group which may have substituent or a cyclic group which may have substituent is preferable.

The alkyl group for $Rd^4$ is preferably a linear or branched alkyl group having 1 to 5 carbon atoms, and specific examples include a methyl group, an ethyl group, a propyl group, an isopropyl group, an n-butyl group, an isobutyl group, a tert-butyl group, a pentyl group, an isopentyl group, and a neopentyl group. Part of the hydrogen atoms within the alkyl group for $Rd^4$ may be substituted with a hydroxy group, a cyano group or the like.

The alkoxy group for $Rd^4$ is preferably an alkoxy group having 1 to 5 carbon atoms, and specific examples thereof include a methoxy group, an ethoxy group, an n-propoxy group, an iso-propoxy group, an n-butoxy group and a tert-butoxy group. Among these, a methoxy group and an ethoxy group are preferable.

As the alkenyl group for $Rd^4$, the same groups as those described above for $R^{101}$ can be exemplified, and a vinyl group, a propenyl group (an allyl group), a 1-methylpropenyl group, and a 2-methylpropenyl group are preferable. These groups may have an alkyl group having 1 to 5 carbon atoms or a halogenated alkyl group having 1 to 5 carbon atoms as a substituent.

As the cyclic group for $Rd^4$, the same groups as those described above for $R^{101}$ can be exemplified. Among these, an alicyclic group in which one or more hydrogen atoms have been removed from a cycloalkane such as cyclopentane, cyclohexane, adamantane, norbornane, isobornane, tricyclodecane, or tetracyclododecane or an aromatic group (e.g., a phenyl group or a naphthyl group) is preferable. When $Rd^4$ is an alicyclic group, the resist composition can be satisfactorily dissolved in an organic solvent, thereby improving the lithography properties. Alternatively, when $Rd^4$ is an aromatic group, the resist composition is excellent in light absorption efficiency in a lithography process using EUV or the like as the exposure light source, thereby resulting in the improvement of the sensitivity and the lithography properties.

In formula (d1-3), $Yd^1$ represents a single bond or a divalent linking group.

The divalent linking group for $Yd^1$ is not particularly limited, and examples thereof include a divalent hydrocarbon group (aliphatic hydrocarbon group, or aromatic hydrocarbon group) which may have a substituent and a divalent linking group containing a hetero atom. As such groups, the same divalent linking groups as those described above for $Ya^{21}$ in the formula (a2-1) are given.

As $Yd^1$, a carbonyl group, an ester bond, an amide bond, an alkylene group, or a combination of these is preferable. As the alkylene group, a linear or branched alkylene group is more preferable, and a methylene group or an ethylene group is still more preferable.

Specific examples of preferable anion moieties for the component (d1-3) are shown below.

[Chemical Formula 40]

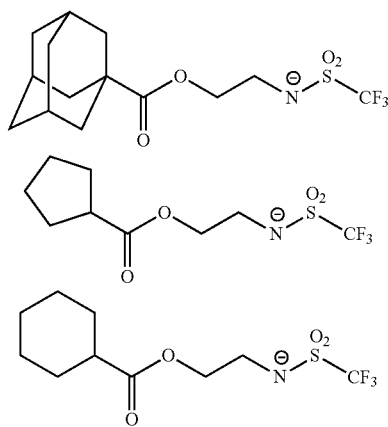

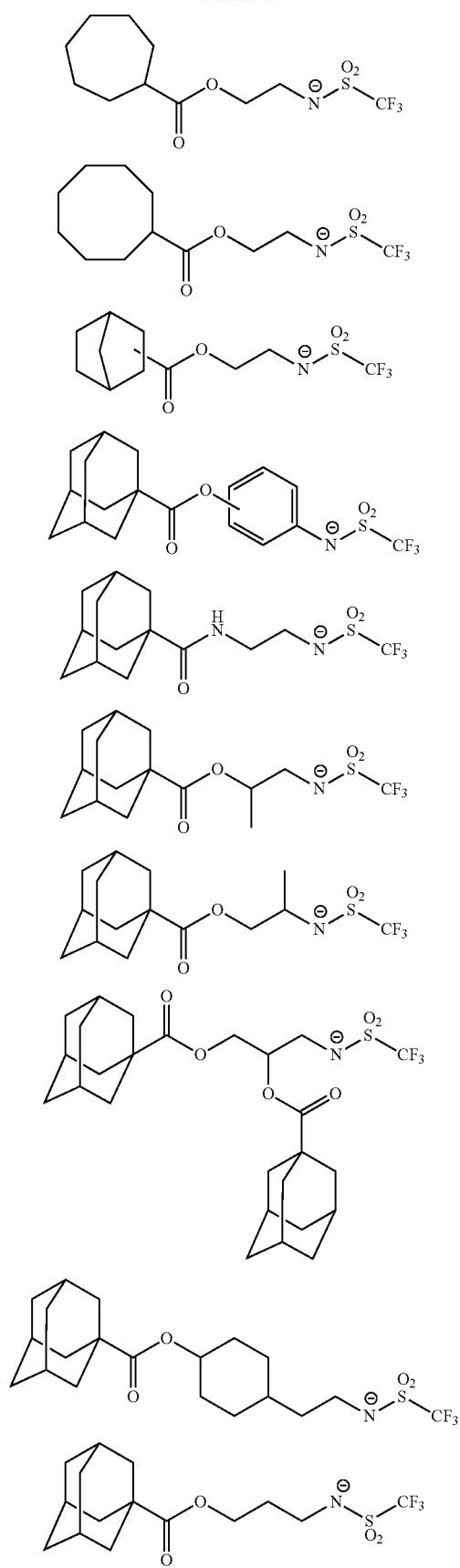
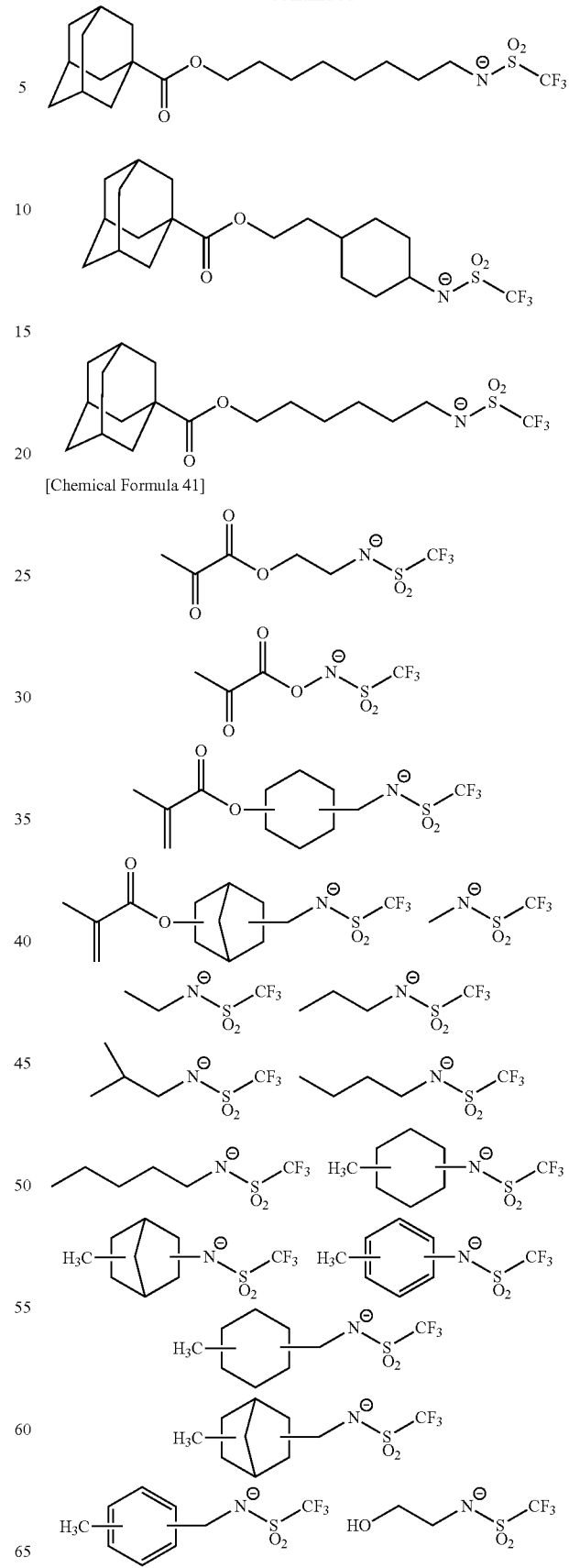

Cation Moiety

In formula (d1-3), $M^{m+}$ is an organic cation having a valency of m, and is the same as those defined for $M^{m+}$ in the aforementioned formula (d1-1).

As the component (d1-3), one kind of compound may be used, or two or more kinds of compounds may be used in combination.

As the component (D1), one kind of the aforementioned components (d1-1) to (d1-3) can be used, or at least two kinds of the aforementioned components (d1-1) to (d1-3) can be used in combination.

The content of the component (D1) relative to 100 parts by weight of the component (A) is preferably within a range from 0.5 to 10 parts by weight, more preferably from 0.5 to 8 parts by weight, and still more preferably from 1 to 8 parts by weight.

When the content of the component (D1) is at least as large as the lower limit of the above-mentioned range, excellent lithography properties and excellent resist pattern shape can be obtained. On the other hand, when the content of the component (D1) is equal to or lower than the upper limit of the above-mentioned range, sensitivity can be maintained at a satisfactory level, and throughput becomes excellent.

The preparation methods of the components (d1-1) and (d1-2) are not particularly limited, and the components (d1-1) and (d1-2) can be prepared by conventional methods.

The content of the component (D1) with respect to 100 parts by weight of the component (A) is preferably 0.5 to 10.0 parts by weight, more preferably 0.5 to 8.0 parts by weight, and still more preferably 1.0 to 8.0 parts by weight. When the content of the component (D1) is at least as large as the lower limit of the above-mentioned range, excellent lithography properties and excellent resist pattern shape can be obtained. On the other hand, when the content of the component (D1) is equal to or lower than the upper limit of the above-mentioned range, sensitivity can be maintained at a satisfactory level, and throughput becomes excellent.

(Component (D2))

The component (D) may contain a nitrogen-containing organic compound component (D2) (hereafter, referred to as component (D2)) which does not fall under the definition of component (D1).

The component (D2) is not particularly limited, as long as it functions as an acid diffusion control agent, and does not fall under the definition of the component (D1). As the component (D2), any of the conventionally known compounds may be selected for use. Among these, an aliphatic amine, particularly a secondary aliphatic amine or tertiary aliphatic amine is preferable.

An aliphatic amine is an amine having one or more aliphatic groups, and the aliphatic groups preferably have 1 to 12 carbon atoms.

Examples of these aliphatic amines include amines in which at least one hydrogen atom of ammonia ($NH_3$) has been substituted with an alkyl group or hydroxyalkyl group having 12 or less carbon atoms (i.e., alkylamines or alkyl-alcoholamines), and cyclic amines.

Specific examples of alkylamines and alkylalcoholamines include monoalkylamines such as n-hexylamine, n-heptylamine, n-octylamine, n-nonylamine, and n-decylamine; dialkylamines such as diethylamine, di-n-propylamine, di-n-heptylamine, di-n-octylamine, and dicyclohexylamine; trialkylamines such as trimethylamine, triethylamine, tri-n-propylamine, tri-n-butylamine, tri-n-pentylamine, tri-n-hexylamine, tri-n-heptylamine, tri-n-octylamine, tri-n-nonylamine, tri-n-decylamine, and tri-n-dodecylamine; and alkyl alcohol amines such as diethanolamine, triethanolamine, diisopropanolamine, triisopropanolamine, di-n-octanolamine, and tri-n-octanolamine. Among these, trialkylamines having 5 to 10 carbon atoms are more preferable, and tri-n-pentylamine and tri-n-octylamine are particularly preferable.

Examples of the cyclic amine include heterocyclic compounds containing a nitrogen atom as a hetero atom. The heterocyclic compound may be a monocyclic compound (aliphatic monocyclic amine), or a polycyclic compound (aliphatic polycyclic amine).

Specific examples of the aliphatic monocyclic amine include piperidine, and piperazine.

The aliphatic polycyclic amine preferably has 6 to 10 carbon atoms, and specific examples thereof include 1,5-diazabicyclo[4.3.0]-5-nonene, 1,8-diazabicyclo[5.4.0]-7-undecene, hexamethylenetetramine, and 1,4-diazabicyclo[2.2.2]octane.

Examples of other aliphatic amines include tris(2-methoxymethoxyethyl)amine, tris{2-(2-methoxyethoxy)ethyl}amine, tris{2-(2-methoxyethoxymethoxy)ethyl}amine, tris{2-(1-methoxyethoxy)ethyl}amine, tris{2-(1-ethoxyethoxy)ethyl}amine, tris{2-(1-ethoxypropoxy)ethyl}amine, tris[2-{2-(2-hydroxyethoxy)ethoxy}ethyl]amine and triethanolamine triacetate, and triethanolamine triacetate is preferable.

Further, as the component (D2), an aromatic amine may be used.

Examples of aromatic amines include aniline, pyridine, 4-dimethylaminopyridine, pyrrole, indole, pyrazole, imidazole and derivatives thereof, as well as diphenylamine, triphenylamine, tribenzylamine, 2,6-diisopropylaniline and N-tert-butoxycarbonylpyrrolidine.

As the component (D2), one kind of compound may be used alone, or two or more kinds thereof may be used in combination.

The component (D2) is generally used in an amount within a range from 0.01 to 5.0 parts by weight, with respect to 100 parts by weight of the component (A). When the amount of the component (D) is within the above-mentioned range, the shape of the resist pattern and the post exposure stability are improved.

As the component (D), one kind of compound may be used, or two or more kinds of compounds may be used in combination.

When the resist composition of the present invention contains the component (D), the amount of the component (D) with respect to 100 parts by weight of the component (A) is preferably 0.1 to 15 parts by weight, more preferably 0.3 to 12 parts by weight, and still more preferably 0.5 to 12 parts by weight. When the amount of the component (D) is at least as large as the lower limit of the above-mentioned range, various lithography properties (such as LWR) of the resulting resist composition are improved. Further, a resist pattern having a more excellent shape can be obtained. On the other hand, when the amount of the component (D) is equal to or lower than the upper limit of the above-mentioned range, sensitivity can be maintained at a satisfactory level and throughput becomes excellent.

<Optional Components>

[Component (E)]

In the present invention, for the purpose of preventing any deterioration in sensitivity, and improving the resist pattern shape and the post exposure stability, at least one compound (E) (hereafter referred to as the component (E)) selected from the group consisting of an organic carboxylic acid, a phosphorus oxo acid and derivative thereof can be added to the resist composition as an optional component to a resist composition.

Examples of suitable organic carboxylic acids include acetic acid, malonic acid, citric acid, malic acid, succinic acid, benzoic acid, and salicylic acid.

Examples of phosphorus oxo acids include phosphoric acid, phosphonic acid and phosphinic acid. Among these, phosphonic acid is particularly preferable.

Examples of phosphorus oxo acid derivatives include esters in which a hydrogen atom within the above-mentioned oxo acids is substituted with a hydrocarbon group. Examples of the hydrocarbon group include an alkyl group having 1 to 5 carbon atoms and an aryl group having 6 to 15 carbon atoms.

Examples of phosphoric acid derivatives include phosphoric acid esters such as di-n-butyl phosphate and diphenyl phosphate.

Examples of phosphonic acid derivatives include phosphonic acid esters such as dimethyl phosphonate, di-n-butyl phosphonate, phenylphosphonic acid, diphenyl phosphonate and dibenzyl phosphonate.

Examples of phosphinic acid derivatives include phosphinic acid esters and phenylphosphinic acid.

As the component (E), one kind may be used alone, or two or more kinds may be used in combination.

The component (E) is typically used in an amount within a range from 0.01 to 5.0 parts by weight, relative to 100 parts by weight of the component (A).

[Component (F)]

The resist composition of the present invention may contain a fluorine additive (hereafter, referred to as "component (F)") for imparting water repellency to the resist film.

As the component (F), for example, a fluorine-containing polymeric compound described in Japanese Unexamined Patent Application, First Publication No. 2010-002870, Japanese Unexamined Patent Application, First Publication No. 2010-032994, Japanese Unexamined Patent Application, First Publication No. 2010-277043, Japanese Unexamined Patent Application, First Publication No. 2011-13569, and Japanese Unexamined Patent Application, First Publication No. 2011-128226 can be used.

More specific examples of the component (F) include polymers having a structural unit (f1) represented by general formula (f1-1) shown below. As the polymer, a polymer (homopolymer) consisting of a structural unit (f1) represented by formula (f1-1) shown below, a copolymer of a structural unit (f1) represented by formula (f1-1) shown below and the aforementioned structural unit (a1); and a copolymer of a structural unit (f1) represented by formula (f1-1) shown below, a structural unit derived from acrylic acid or methacrylic acid and the aforementioned structural unit (a1) are preferable. As the structural unit (a1) to be copolymerized with a structural unit (f1) represented by formula (f1-1) shown below, a structural unit derived from 1-ethyl-1-cyclooctyl(meth)acrylate or a structural unit represented by the aforementioned formula (a1-2-01) is preferable.

[Chemical Formula 42]

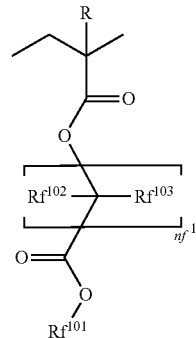

In the formula, R is the same as those defined above; $Rf^{102}$ and $Rf^{103}$ each independently represents a hydrogen atom, a halogen atom, an alkyl group having 1 to 5 carbon atoms, or a halogenated alkyl group having 1 to 5 carbon atoms, provided that $Rf^{102}$ and $Rf^{103}$ may be the same or different; $nf^1$ represents an integer of 1 to 5; and $Rf^{101}$ represents an organic group containing a fluorine atom.

In formula (f1-1), R is the same as those defined above. As R, a hydrogen atom or a methyl group is preferable.

In formula (f1-1), examples of the halogen atom for $Rf^{102}$ and $Rf^{103}$ include a fluorine atom, a chlorine atom, a bromine atom and an iodine atom, and a fluorine atom is particularly preferable. Examples of the alkyl group having 1 to 5 carbon atoms for $Rf^{102}$ and $Rf^{103}$ include the same alkyl group having 1 to 5 carbon atoms as those described above for R, and a methyl group or an ethyl group is preferable. Specific examples of the halogenated alkyl group having 1 to 5 carbon atoms for $Rf^{102}$ or $Rf^{103}$ include groups in which part or all of the hydrogen atoms of the aforementioned alkyl groups having 1 to 5 carbon atoms have been substituted with halogen atoms. Examples of the halogen atom include a fluorine atom, a chlorine atom, a bromine atom and an iodine atom, and a fluorine atom is particularly preferable. Among these, as $Rf^{102}$ and $Rf^{103}$, a hydrogen atom, a fluorine atom or an alkyl group having 1 to 5 carbon atoms is preferable, and a hydrogen atom, a fluorine atom, a methyl group or an ethyl group is more preferable.

In formula (f1-1), $nf^1$ represents an integer of 1 to 5, preferably an integer of 1 to 3, and more preferably 1 or 2.

In formula (f1-1), $Rf^{101}$ represents an organic group containing a fluorine atom, and is preferably a hydrocarbon group containing a fluorine atom.

The hydrocarbon group containing a fluorine atom may be linear, branched or cyclic, and preferably has 1 to 20 carbon atoms, more preferably 1 to 15 carbon atoms, and particularly preferably 1 to 10 carbon atoms.

With regard to the hydrocarbon group having a fluorine atom, preferably 25% or more, more preferably 50% or more, and particularly preferably 60% or more of the hydrogen atoms within the hydrocarbon group are substituted with fluorine atoms, as the hydrophobicity of the resist film during immersion exposure is enhanced.

Among these, as $Rf^{101}$, a fluorinated hydrocarbon group having 1 to 5 carbon atoms is particularly preferable, and a methyl group, $-CH_2-CF_3$, $-CH_2-CF_2-CF_3$, $-CH(CF_3)_2$, $-CH_2-CH_2-CF_3$, and $-CH_2-CH_2-CF_2-CF_2-CF_2-CF_3$ are most preferable.

The weight average molecular weight (Mw) (the polystyrene equivalent value determined by gel permeation chromatography) of the component (F) is preferably 1,000 to 50,000, more preferably 5,000 to 40,000, and most preferably 10,000 to 30,000. When the weight average molecular weight is equal to or lower than the upper limit of the above-mentioned range, the resist composition exhibits a satisfactory solubility in a resist solvent at the time of being used as a resist. On the other hand, when the weight average molecular weight is at least as large as the lower limit of the above-mentioned range, dry etching resistance and the cross-sectional shape of the resist pattern becomes satisfactory.

Further, the dispersity (Mw/Mn) of the component (F) is preferably 1.0 to 5.0, more preferably 1.0 to 3.0, and most preferably 1.2 to 2.5.

As the component (F), one kind may be used alone, or two or more kinds may be used in combination.

The component (F) is typically used in a ratio within a range from 0.5 parts by weight to 10 parts by weight, relative to 100 parts by weight of the component (A).

If desired, other miscible additives can also be added to the resist composition of the present invention. Examples of such miscible additives include additional resins for improving the performance of the resist film, dissolution inhibitors, plasticizers, stabilizers, colorants, halation inhibitors, and dyes.

[Component (S)]

The resist composition according to the present invention can be prepared by dissolving the materials for the resist composition in an organic solvent (hereafter, referred to as "component (S)" in some cases).

The component (S) may be any organic solvent which can dissolve the respective components to give a uniform solution, and one or more kinds of any organic solvent can be appropriately selected from those which have been conventionally known as solvents for a chemically amplified resist.

Examples thereof include lactones such as γ-butyrolactone; ketones such as acetone, methyl ethyl ketone (MEK), cyclohexanone, methyl-n-pentyl ketone (2-heptanone) and methyl isopentyl ketone; polyhydric alcohols, such as ethylene glycol, diethylene glycol, propylene glycol and dipropylene glycol; compounds having an ester bond, such as ethylene glycol monoacetate, diethylene glycol monoacetate, propylene glycol monoacetate, and dipropylene glycol monoacetate; polyhydric alcohol derivatives including compounds having an ether bond, such as a monoalkylether (e.g., monomethylether, monoethylether, monopropylether or monobutylether) or monophenylether of any of these polyhydric alcohols or compounds having an ester bond (among these, propylene glycol monomethyl ether acetate (PGMEA) and propylene glycol monomethyl ether (PGME) are preferable); cyclic ethers such as dioxane, esters such as methyl lactate, ethyl lactate (EL), methyl acetate, ethyl acetate, butyl acetate, methyl pyruvate, ethyl pyruvate, methyl methoxypropionate, and ethyl ethoxypropionate; aromatic organic solvents such as anisole, ethylbenzylether, cresylmethylether, diphenylether, dibenzylether, phenetole, butylphenylether, ethylbenzene, diethylbenzene, pentylbenzene, isopropylbenzene, toluene, xylene, cymene and mesitylene; and dimethylsulfoxide (DMSO).

These organic solvents can be used individually, or as a mixture of two or more kinds thereof.

Among these, PGMEA, PGME, γ-butyrolactone and EL are preferable.

Further, a mixed solvent obtained by mixing PGMEA with a polar solvent is preferable. The mixing ratio (weight ratio) of the mixed solvent can be appropriately determined, taking into consideration the compatibility of the PGMEA with the polar solvent, but is preferably in the range of 1:9 to 9:1, more preferably from 2:8 to 8:2.

More specifically, when EL or cyclohexanone is mixed as the polar solvent, the weight ratio of PGMEA:EL or cyclohexanone is preferably from 1:9 to 9:1, and more preferably from 2:8 to 8:2. Alternatively, when PGME is mixed as the polar solvent, the weight ratio of PGMEA:PGME is preferably from 1:9 to 9:1, more preferably from 2:8 to 8:2, and still more preferably 3:7 to 7:3.

Further, as the component (S), a mixed solvent of at least one of PGMEA and EL with γ-butyrolactone is also preferable. The mixing ratio (former:latter) of such a mixed solvent is preferably from 70:30 to 95:5.

The amount of the component (S) used is not particularly limited, and is appropriately adjusted so as to achieve a concentration which enables coating of a coating solution to a substrate or the like according to the thickness of the coating film. In general, the organic solvent is used in an amount such that the solid content concentration of the resist composition becomes within the range from 1% by weight to 20% by weight, and preferably from 2% by weight to 15% by weight.

In the method of forming a split pattern according to the present invention, the first resist pattern is formed in the step A, and then the solubility of the first resist pattern surface in a developing solution is changed in steps B to D. Then, in the step D, an organic solvent development is conducted, so as to remove an organic solvent-soluble region of the first resist pattern, thereby forming a split pattern in which the first resist pattern is split into line, space and line.

In step D, the organic solvent-soluble region of the first resist pattern is removed by an organic solvent development. More specifically, when the portion shown as 2b in FIG. 1(d), by the portion shown as 2b having satisfactory solubility in the organic solvent, the portion shown 2b is easily to be removed in the developing process of the step D and thereby enabling to form a line pattern whose size is around several tens of nanometers (particularly, 20 to 30 nm).

Therefore, the resist composition forming the first resist pattern preferably has high dissolution rate in an organic solvent.

When the dissolution rate is a dissolution rate in an organic solvent, such as butyl acetate (an amount of thickness loss per immersing time), the maximum value of the dissolution rate ($R_{max}$, unit: nm/s) is preferably 5 nm/s or more, and more preferably 10 nm/s or more. Further, the minimum value of the dissolution rate ($R_{min}$, unit: nm/s) is preferably 1 nm/s or less, and more preferably 0.5 nm/s or less.

Step B

In step B, a solution containing an acid or a thermoacid generator is applied to form a first layer covering the first resist pattern. In step B, as shown in FIG. 1(b), the first layer 3 is formed to cover the first resist pattern 2 formed in step A.

[Solution Containing Acid or Thermoacid Generator]

In the present invention, a solution containing an acid or a thermoacid generator is described. Preferably, the solution includes an acid or a thermoacid generator, a polymeric compound, and a solvent.

[Acid (Acid Component (T0))]

In the present invention, the "acid" refers to a substance which has acidity and acts as a proton donor (hereinafter, referred to as an "acid component (T0)" in some cases). As the component (T0), nonionic acids not forming salts are exemplified.

Examples of the component (T0) include acid components, such as a fluorinated alkyl group-containing carboxylic acid, a higher aliphatic acid, a higher alkyl sulfonic acid, a higher alkyl aryl sulfonic acid, and a camphor sulfonic acid.

As the fluorinated alkyl group-containing carboxylic acid, $C_{10}F_{21}COOH$ is exemplified.

As the higher aliphatic acid, higher aliphatic acids having an alkyl group having 8 to 20 carbon atoms are exemplified. Specific examples thereof include dodecanoic acid, tetradecanoic acid, and stearic acid.

The alkyl group having 8 to 20 carbon atoms may be a linear or branched alkyl group, an alkyl group having a phenylene group or an oxygen atom in the chain thereof, or an alkyl group in which some of hydrogen atoms are substituted with hydroxy groups or carboxy groups.

As the higher alkyl sulfonic acid, sulfonic acids having an alkyl group having an average carbon number of preferably 9 to 21, and more preferably 12 to 18 are exemplified. Specific examples thereof include decane sulfonic acid, dodecane sulfonic acid, tetra-decane sulfonic acid, penta-decane sulfonic acid, and stearic sulfonic acid.

As the higher alkyl aryl sulfonic acid, alkyl benzene sulfonic acid and alkyl naphthalene sulfonic acid each having an alkyl group having an average carbon number of preferably 6 to 18, and more preferably 9 to 15 are exemplified. Specific examples thereof include dodecyl benzene sulfonic acid and decyl naphthalene sulfonic acid.

As other acid components, alkyl diphenyl ether disulfonic acids having an alkyl group having an average carbon number of preferably 6 to 18, and more preferably 9 to 15 are exemplified. A specific example thereof includes dodecyl diphenyl ether disulfonic acid.

[Thermoacid Generator (Acid Component (T1))]

The thermoacid generator (hereinafter, referred to as "acid component (T1)" in some cases) is a component which generates an acid by heating. As the thermoacid generator component generating an acid by heating, so far, various kinds of acid generator have been known. Examples thereof include: onium salt acid generators such as iodonium salts and sulfonium salts; oxime sulfonate acid generators; diazomethane acid generators such as bisalkyl or bisaryl sulfonyl diazomethanes and poly(bis-sulfonyl)diazomethanes; nitrobenzylsulfonate acid generators; iminosulfonate acid generators; and disulfone acid generators. These acid generator components are also known as photo-acid generators, but also function as thermoacid generators. Therefore, as the acid generator components which can be used in the present invention, any of the known acid generators used in conventional chemically amplified resist compositions can be used.

Among these, as the acid component (T1), a compound represented by any of general formulae (T1-1) to (T1-3) is preferable.

[Chemical Formula 43]

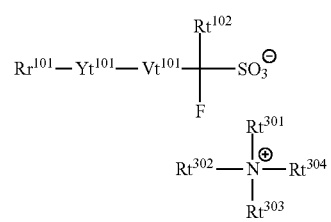

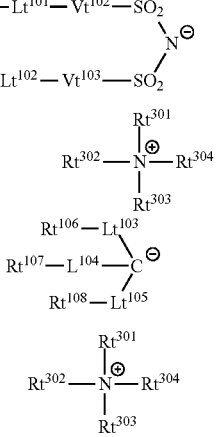

In the formulae, $Rt^{101}$ and $Rt^{104}$ to $Rt^{108}$ each independently represents a cyclic group which may have a substituent, a chain-like alkyl group which may have a substituent or a chain-like alkenyl group which may have a substituent, $Rt^{104}$ and $Rt^{105}$ may be mutually bonded to form a ring; $Rt^{106}$ and $Rt^{107}$ may be mutually bonded to form a ring; $Rt^{102}$ represents a fluorine atom or a fluorinated alkyl group having 1 to 5 carbon atoms; $Yt^{101}$ represents a single bond or a divalent linking group containing an oxygen atom; $Vt^{101}$ to $Vt^{103}$ each independently represents a single bond, an alkylene group or a fluorinated alkylene group; $Lt^{101}$ and $Lt^{102}$ each independently represents a single bond or an oxygen atom; $Lt^{103}$ to $Lt^{105}$ each independently represents a single bond, —CO— or —SO$_2$—; $Rt^{301}$ to $Rt^{304}$ each independently represents a hydrogen atom or a linear, branched or cyclic fluorinated alkyl group having 1 to 12 carbon atoms; and $Rt^{301}$ to $Rt^{303}$ may be bonded to each other to form a ring together with a nitrogen atom in the formula.

{Anion Moiety}

Anion Moiety of Component (T1-1)

In the formula (T1-1), $Rt^{101}$ is a cyclic group which may have a substituent, a chain-like alkyl group which may have a substituent or a chain-like alkenyl group which may have a substituent.

The description of $Rt^{101}$ in the formula (T1-1) is similar to the description of R101 in the formula (b-1).

In the formula (T1-1), $Yt^{101}$ is a single bond or a divalent linking group containing an oxygen atom.

The description of $Yt^{101}$ in the formula (T1-1) is similar to the description of $Y^{101}$ in the formula (b-1).

In the formula (T1-1), $Vt^{101}$ is a single bond, an alkylene group or a fluorinated alkylene group. Preferably, the alkylene group or fluorinated alkylene group in $Vt^{101}$ has 1 to 4 carbon atoms. As the fluorinated alkylene group in $Vt^{101}$, an alkylene group in $Vt^{101}$ in which some or all of the hydrogen atoms thereof are substituted with fluorine atoms is exemplified. Among these, $Vt^{101}$ is preferably a single bond or a fluorinated alkylene group having 1 to 4 carbon atoms.

In the formula (T1-1), $Rt^{102}$ is a fluorine atom or a fluorinated alkyl group having 1 to 5 carbon atoms. $Rt^{102}$ is preferably a fluorine atom or a perfluoroalkyl group having 1 to 5 carbon atoms, and more preferably a fluorine atom.

Specific examples of anion moiety of component (T1-1) include fluorinated alkyl sulfonate anions such as trifluoromethane sulfonate anion and perfluorobutane sulfonate anion, when $Yt^{101}$ is a single bond; and include anions represented by any of the formulae (an-1) to (an-3), when $Yt^{101}$ is a divalent linking group containing an oxygen atom.

Anion Moiety of Component (T1-2)

In the formula (T1-2), $Rt^{104}$ and $Rt^{105}$ each independently represents a cyclic group which may have a substituent, a chain-like alkyl group which may have a substituent, or a chain-like alkenyl group which may have a substituent, and is the same as those defined for $Rt^{101}$ in the formula (T1-1). $Rt^{104}$ and $Rt^{105}$ may be mutually bonded to form a ring.

Each of $Rt^{104}$ and $Rt^{105}$ is preferably a chain-like alkyl group which may have a substituent, and more preferably a linear or branched alkyl group or a linear or branched fluorinated alkyl group.

The chain-like alkyl group preferably has 1 to 10 carbon atoms, more preferably 1 to 7 carbon atoms, and still more preferably 1 to 3 carbon atoms. The smaller the number of carbon atoms of the chain-like alkyl group for $Rt^{104}$ and $Rt^{105}$ in the range described above, the more it is preferable because the solubility in a resist solvent is improved. Further, in the chain-like alkyl group for $Rt^{104}$ and $Rt^{105}$, it is preferable that the number of hydrogen atoms substituted with fluorine atoms is as large as possible because the acid strength increases and the transparency to high energy radiation of 200 nm or less or electron beam is improved. The ratio of fluorine atoms, that is, the fluorination ratio of the chain-like alkyl group is preferably from 70% to 100%, more preferably from 90% to 100%, and it is more preferable that the chain-like alkyl group to be a perfluoroalkyl group in which all hydrogen atoms are substituted with fluorine atoms.

In formula (T1-2), $Vt^{102}$ and $Vt^{103}$ each independently represents a single bond, an alkylene group or a fluorinated alkylene group, and is the same as those defined for $Vt^{101}$ in formula (T1-1).

In formula (T1-2), $Lt^{101}$ and $Lt^{102}$ each independently represents a single bond or an oxygen atom.

Anion Moiety of Component (T1-3)

In formula (T1-3), $Rt^{106}$ to $Rt^{108}$ each independently represents a cyclic group which may have a substituent, a chain-like alkyl group which may have a substituent or a chain-like alkenyl group which may have a substituent, and is the same as those defined for $Rt^{101}$ in formula (T1-1).

$Lt^{103}$ to $Lt^{105}$ each independently represents a single bond, —CO— or —SO$_2$—.

{Cation Moiety}

In the cation moieties in the formulae (T1-1) to (T1-3), $Rt^{301}$ to $Rt^{304}$ each independently represents a hydrogen atom or a linear, branched or cyclic fluorinated alkyl group having 1 to 12 carbon atoms. $Rt^{301}$ to $Rt^{303}$ may be mutually bonded to form a ring together with the nitrogen atom in the formula. As to the formed ring, one ring containing the nitrogen atom in the formula in the ring skeleton thereof is preferably a 3 to 10-membered ring, and particularly preferably a 5 to 7-membered ring including the nitrogen atom. A specific example of the formed ring includes a pyridine ring. Hereinafter, preferable specific examples of the cation moieties in the formulae (T1-1) to (T1-3) will be described.

[Chemical Formula 44]

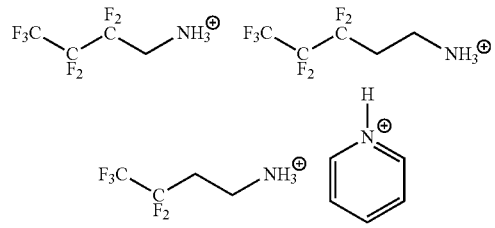

As the acid component (T1), a compound represented by the general formula (T1-1) is preferable. As the anion moiety of the compound represented by the general formula (T1-1), the anion moiety represented by the formula (an-1) is preferable.

In the solution containing an acid or a thermoacid generator, the aforementioned acid components (T0) and (T1) may be used alone or in combination of two or more kinds thereof.

In the solution containing an acid or a thermoacid generator according to the present invention, the content of the acid component (T0) or (T1) in the solution is preferably 0.1 parts by weight to 5 parts by weight, more preferably 0.15 parts by weight to 3 parts by weight, and still more preferably 0.15 parts by weight to 1.5 parts by weight, with respect to 100 parts by weight of the solution containing an acid or a thermoacid generator.

[Polymeric Compound (Tp)]

In the present invention, a polymeric compound which is preferably contained in the solution containing an acid or a thermoacid generator will be described. The polymeric compound which is preferably contained in the solution containing an acid or a thermoacid generator is referred to as "polymeric compound (Tp)" in some cases. The polymeric compound (Tp) is not particularly limited as long as it serves to improve the coating properties of the solution containing an acid or a thermoacid generator, and can be removed by the organic solvent development in the following step D, that is, it can be dissolved in an organic solvent.

In the present invention, it is preferable that the polymeric compound (Tp) contains a structural unit having a hydrocarbon group which may have a substituent. The structural unit having a hydrocarbon group which may have a substituent is, for example, a structural unit represented by general formula (Tp)-1.

[Chemical Formula 45]

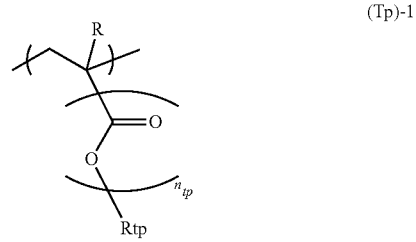

In the formula, R represents a hydrogen atom, an alkyl group having 1 to 5 carbon atoms, or a halogenated alkyl group having 1 to 5 carbon atoms, and Rtp represents a hydrocarbon group which may have a substituent. $n_{tp}$ is 0 or 1. When $n_{tp}$ is 0, Rtp may be a hydroxy group.

In the general formula (Tp)-1, R represents a hydrogen atom, an alkyl group having 1 to 5 carbon atoms, or a halogenated alkyl group having 1 to 5 carbon atoms, and is the same as those defined for R in formula (a1-1).

In the general formula (Tp)-1, Rtp represents a hydrocarbon group which may have a substituent.

The hydrocarbon group represented by Rtp is preferably an alkyl group having 1 to 20 carbon atoms, more preferably an alkyl group having 1 to 10 carbon atoms, and preferably a linear or branched alkyl group. Specific examples thereof include a methyl group, an ethyl group, a propyl group, an isopropyl group, an n-butyl group, an isobutyl group, a tert-butyl group, a pentyl group, an isopentyl group, a neopentyl group, a 1,1-dimethylethyl group, a 1,1-diethyl propyl group, a 2,2-dimethyl propyl group, and a 2,2-dimethyl butyl group.

When Rtp is a cyclic hydrocarbon group, the cyclic hydrocarbon group may be an aliphatic or aromatic hydrocarbon group, and may also be a monocyclic hydrocarbon group or a polycyclic hydrocarbon group. As the monocyclic alicyclic hydrocarbon group, a group in which one hydrogen atom has been removed from a monocycloalkane is preferable. The monocycloalkane preferably has 3 to 8 carbon atoms, and specific examples thereof include cyclopentane, cyclohexane, and cyclooctane. As the polycyclic alicyclic hydrocarbon group, a group in which one hydrogen atom has been removed from a polycycloalkane is preferable, and the polycycloalkane preferably has 7 to 12 carbon atoms. Specific examples of the polycycloalkane include adamantane, norbornane, isobornane, tricyclodecane and tetracyclododecane.

When Rtp is an aromatic hydrocarbon group, specific examples of the aromatic ring contained in the aromatic hydrocarbon group include aromatic hydrocarbon rings, such as benzene, biphenyl, fluorene, naphthalene, anthracene and phenanthrene; and aromatic hetero rings in which part of the carbon atoms constituting the aforementioned aromatic hydrocarbon rings has been substituted with a hetero atom. Examples of the hetero atom within the aromatic hetero rings include an oxygen atom, a sulfur atom and a nitrogen atom.

Specific examples of the aromatic hydrocarbon group include a group in which one hydrogen atom has been removed from the aforementioned aromatic hydrocarbon ring (aryl group); and a group in which one hydrogen atom of the aforementioned aryl group has been substituted with an alkylene group (such as a benzyl group, a phenethyl group, a 1-naphthylmethyl group, a 2-naphthylmethyl group, a 1-naphthylethyl group, or a 2-naphthylethyl group). The alkylene group (alkyl chain within the arylalkyl group) preferably has 1 to 4 carbon atom, more preferably 1 or 2 carbon atoms, and most preferably 1 carbon atom.

Rtp may or may not have a substituent. Examples of the substituent include an alkyl group, an alkoxy group, a halogen atom, a halogenated alkyl group, a hydroxy group and a carbonyl group.

The alkyl group as the substituent is preferably an alkyl group having 1 to 5 carbon atoms, and more preferably a methyl group, an ethyl group, a propyl group, an n-butyl group or a tert-butyl group.

The alkoxy group as the substituent is preferably an alkoxy group having 1 to 5 carbon atoms, more preferably a methoxy group, an ethoxy group, an n-propoxy group, an iso-propoxy group, an n-butoxy group or a tert-butoxy group, and most preferably a methoxy group or an ethoxy group.

Examples of the halogen atom as the substituent include a fluorine atom, a chlorine atom, a bromine atom and an iodine atom, and a fluorine atom is preferable.

Examples of the halogenated alkyl group as the substituent include groups in which part or all of the hydrogen atoms within the aforementioned alkyl groups has been substituted with the aforementioned halogen atoms.

In the cyclic aliphatic hydrocarbon group, a part of the carbon atoms constituting the ring structure thereof may be substituted with a substituent containing a hetero atom. As the substituent containing a hetero atom, —O—, —C(=O)—O—, —S—, —S(=O)$_2$— or —S(=O)$_2$—O— is preferable.

When $n_{tp}$ is 0, Rtp may be a hydroxy group.

The structural unit represented by the general formula (Tp)-1 is preferably a structural unit (Tp)-1-1 including a polar group-containing aliphatic hydrocarbon group having a polar group as a substituent, a structural unit (Tp)-1-2 derived from hydroxystyrene, a structural unit (Tp)-1-3 derived from styrene, a structural unit (Tp)-1-4 containing a chain-like or cyclic aliphatic hydrocarbon group, or a structural unit (Tp)-1-5 derived from vinyl alcohol.

In the present invention, as the structural unit (Tp)-1-1, the aforementioned structural unit (a3) including a polar group-containing aliphatic hydrocarbon group is preferable. In the structural unit (a3), the structural unit represented by the general formula (a3-1) or (a3-3) is preferable.

As the structural unit (Tp)-1-2, a structural unit represented by general formula (Tp)-1-2-1 below is exemplified. As the structural unit (Tp)-1-3, a structural unit represented by general formula (Tp)-1-3-1 below is exemplified.

[Chemical Formula 46]

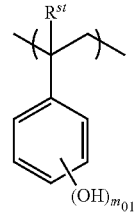

(Tp)-1-2-1

In the formula, $R^{st}$ represents a hydrogen atom or a methyl group, and mot represents an integer of 1 to 3.

[Chemical Formula 47]

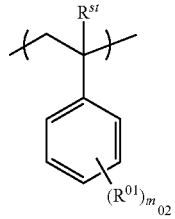

(Tp)-1-3-1

In the formula, $R^{st}$ represents a hydrogen atom or a methyl group, $R^{01}$ represents an alkyl group having 1 to 5 carbon atoms, and $m_{02}$ represents an integer of 0 or 1 to 3.

In the general formula (Tp)-1-2-1, $R^{st}$ is a hydrogen atom or a methyl group, and preferably a hydrogen atom.

$m_{01}$ is an integer of 1 to 3, and preferably 1.

The position of a hydroxy group may be any of an o-position, an m-position, and a p-position, but, in terms of easy availability and low price, it is preferable that $m_{01}$ is 1 and a hydroxy group is at a p-position. When $m_{01}$ is 2 or 3, it is possible to combine arbitrary substitution positions.

In the general formula (Tp)-1-3-1, $R^{st}$ is a hydrogen atom or a methyl group, and preferably a hydrogen atom.

The $R^{01}$ is a linear or branched alkyl group having 1 to 5 carbon atoms, and examples thereof include a methyl group, an ethyl group, a propyl group, an isopropyl group, an n-butyl group, an isobutyl group, a tert-butyl group, a pentyl group, an isopentyl group, and a neopentyl group. Industrially, a methyl group or an ethyl group is preferable.

The $m_{02}$ is an integer of 0 or 1 to 3. Among these, 0 or 1 is preferable, and, industrially, 0 is particularly preferable.

When $m_{02}$ is 1, the substitution position of $R^{01}$ may be any of an o-position, an m-position, and a p-position. When $m_{02}$ is 2 or 3, it is possible to combine arbitrary substitution positions.

As the structural unit (Tp)-1-4, the structural unit represented by any of the formulae (a4-1) to (a4-7), or a structural unit represented by general formula (Tp)-1-4-1 below is exemplified.

[Chemical Formula 48]

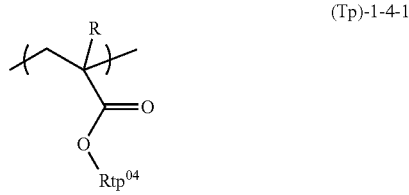

(Tp)-1-4-1

In the formula, R represents a hydrogen atom, an alkyl group having 1 to 5 carbon atoms, or a halogenated alkyl group having 1 to 5 carbon atoms, and $Rtp^{04}$ represents a linear alkyl group having 1 to 10 carbon atoms.

As the polymeric compound (Tp) preferably contained in the solution containing an acid or a thermoacid generator, a combination of the structural unit represented by (Tp)-1-2 and the structural unit represented by (Tp)-1-3, a combination of two or more kinds of the structural units represented by (Tp)-1-1, a combination of two or more kinds of the structural units represented by (Tp)-1-4, or polyvinyl alcohol is preferably exemplified.

In the solution containing an acid or a thermoacid generator, the aforementioned polymer compounds (Tp) may be used alone or in combination of two or more kinds thereof.

In the solution containing an acid or a thermoacid generator according to the present invention, the content of the polymer compounds (Tp) in the solution is preferably 0.1 parts by weight to 10 parts by weight, more preferably 0.2 parts by weight to 5 parts by weight, and still more preferably 0.3 parts by weight to 3 parts by weight, with respect to 100 parts by weight of the solution containing an acid or a thermoacid generator.

[Solvent]

In the present invention, a solvent (hereinafter, referred to as "solvent (B)" in some cases) contained in the solution containing an acid or a thermoacid generator will be described. In step B, the solution containing an acid or a thermoacid generator is applied so as to cover the first resist pattern to form a first layer. Therefore, it is preferable that the solvent contained in the solution containing an acid or a thermoacid generator is a solvent that does not dissolve the first resist pattern.

Specifically, as the solvent, water, an ether-based solvent, or a linear monohydric alcohol having 1 to 10 carbon atoms is preferably employed.

The ether-based solvent is an organic solvent containing C—O—C in the structure thereof. Examples of the ether-based solvent include diethyl ether, 1-(isopentyloxy)-3-methylbutane, diisopropyl ether, and tetrahydrofuran.

The alcohol-based solvent is preferably a monohydric alcohol having 6 to 8 carbon atoms, and the monohydric alcohol may be a linear, branched or cyclic monohydric alcohol. Specific examples of the alcohol-based solvent include 1-hexanol, 1-heptanol, 1-octanol, 2-hexanol, 2-heptanol, 2-octanol, 3-hexanol, 3-heptanol, 3-octanol, 4-octanol, benzyl alcohol, 4-methylpentane-2-ol, and 2-methylbutane-1-ol. Among these, 4-methylpentane-2-ol or 2-methylbutane-1-ol is more preferable.

The amount of solvent (B) to be used is not particularly limited, and is appropriately set so as to achieve a concentration capable of being applied on the first resist pattern depending on coating thickness. Generally, solvent (B) is used such that the solid content concentration in the solution containing an acid or a thermoacid generator is within a range of 0.1% by weight to 10% by weight, and preferably 1% by weight to 5% by weight.

The thickness of the first layer is not particularly limited as long as the first resist pattern is covered with the first layer. For example, the thickness thereof is preferably 0.2 to 2.0, more preferably 0.3 to 1.8, and particularly preferably 0.5 to 1.2, with respect to pattern height 1 of the first resist pattern.

Step B1

Step B1 is a step of applying a solvent-containing solution to cover the first layer.

As shown in FIG. 1(c), the solvent-containing solution 4 is applied to cover the first layer 3.

The solvent-containing solution is applied for the purpose of controlling the action of the acid contained in the first layer formed in step B. The solvent-containing solution 4 is applied to cover the first layer 3, and may be partially mixed with the upper portion of the first layer 3.

A solvent (hereinafter, referred to as "solvent (C)" in some cases) is not particularly limited as long as it can control the action of an acid.

As the solvent (C), in addition to the same solvent as the above solvent (B), solvents exemplified as the component (S) of the aforementioned resist composition, or a mixed solvent thereof are employed.

It is preferable that the solvent (C) does not dissolve the first layer. Therefore, it is preferable that a low-polarity solvent is employed as the solvent (C).

Examples of the low-polarity solvent include: aliphatic hydrocarbon solvents having 4 to 12 carbon atoms, such as butane, pentane, hexane, and octane; aromatic hydrocarbon solvents, such as toluene and xylene; and alicyclic hydrocarbon solvents, such as cyclohexane.

Among these, diethyl ether, 1-(isopentyloxy)-3-methylbutane, diisopropyl ether, tetrahydrofuran, or a mixed solvent of 1-(isopentyloxy)-3-methyl butane and PGMEA is preferable.

In the present invention, it is preferable that the solvent-containing solution contains an acid diffusion control agent.

The acid diffusion control agent is not particularly limited as long as it acts as a quencher trapping the acid of acid component in the first layer. In the present invention, a nitrogen-containing organic compound component, which is described as component (D2) of the resist composition, is preferably employed.

Further, an ionic nitrogen-containing organic compound component may be used, and a compound including a cation moiety represented by general formula (Cd) below and an anion moiety represented by the above general formula (d1-1) is preferably used.

[Chemical Formula 49]

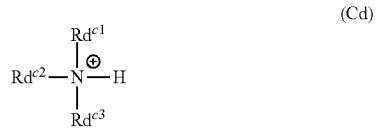

(Cd)

In the formula, $Rd^{c1}$ to $Rd^{c3}$ each independently represents an alkyl group which may have a substituent.

In the formula (Cd), $Rd^{c1}$ to $Rd^{c3}$ each independently represents an alkyl group which may have a substituent. Preferably, $Rd^{c1}$ to $Rd^{c3}$ each independently represents a linear alkyl group having 1 to 5 carbon atoms.

In the solvent-containing solution, the aforementioned acid diffusion control agents may be used alone or in combination of two or more kinds thereof.

In the solvent-containing solution according to the present invention, the content of the acid diffusion control agent in the solution is preferably 0.05 parts by weight to 5 parts by weight, more preferably 0.05 parts by weight to 2.5 parts by weight, and still more preferably 0.1 parts by weight to 1 part by weight, with respect to 100 parts by weight of the solvent-containing solution.

[Polymeric Compound (Cp)]

The preferable polymeric compound (Cp) contained in the solvent-containing solution is the same as the above polymeric compound (Tp).

As the polymeric compound (Cp), a combination of the structural unit represented by (Tp)-1-2 and the structural unit represented by (Tp)-1-3, a combination of two or more kinds of the structural units represented by (Tp)-1-4, a combination of the structural unit represented by (Tp)-1-1 and the structural unit represented by (Tp)-1-4, or polyvinyl alcohol is preferably exemplified.

In the solvent-containing solution, the aforementioned polymer compounds (Cp) may be used alone or in combination of two or more kinds thereof.

In the solution containing an acid or a thermoacid generator according to the present invention, the content of the polymer compounds (Cp) in the solution is preferably 0.1 parts by weight to 10 parts by weight, more preferably 0.5 parts by weight to 5 parts by weight, and still more preferably 0.6 parts by weight to 2 parts by weight, with respect to 100 parts by weight of the solution containing an acid or a thermoacid generator.

In the present invention, the solvent (B) contained in the solution containing an acid or a thermoacid generator and the solvent (C) contained in the solvent-containing solution, each of the solvent (B) and the solvent (C) being used for forming the first layer, may be the same as or different from each other. When the solvent (B) and the solvent (C) are different from each other, for example, a monohydric alcohol solvent may be selected as the solvent (B), and an ether solvent may be employed as the solvent (C); a monohydric alcohol solvent may be selected as the solvent (C), and an ether solvent may be employed as the solvent (B); water may be selected as the solvent (B), and an ether solvent may be employed as the solvent (C); and a monohydric alcohol solvent may be selected as the solvent (B), and water may be employed as the solvent (C).

The amount of the solvent (C) used is not particularly limited, and is appropriately set so as to achieve a concentration capable of being applied on the first layer depending on coating thickness. Generally, the solvent (C) is used such that the solid content concentration in the solvent-containing solution is within a range of 0.1% by weight to 10% by weight, and preferably 1% by weight to 5% by weight.

Step C

Step C is step of heating a structure containing the first resist pattern obtained from the steps (A) to (C) to change the solubility of the first resist pattern in a developing solution by the action of acid in the first layer. In step C, as the heating treatment, for example, baking treatment may be carried out at 90° C. to 110° C. for 50 to 120 seconds.

When the solvent-containing solution is applied to cover the first layer in step B1, the action of acid caused by the heating treatment can be controlled in step C.

In the above [step A], the first resist pattern 2 is formed by alkali development using the positive type resist composition. In other words, as shown in FIG. 1(a), the surface of the resist pattern 2 is provided with an alkali-insoluble region.

In step C, the solubility of the first resist pattern 2 in a developing solution is changed by the action of acid. Specifically, the surface of the first resist pattern is deprotected by the action of the acid in the first layer formed in [step B] to decrease the solubility of the first resist pattern in an organic solvent.

On the other hand, since a solvent-made layer 4 is formed on the pattern, it is considered that the action of acid on the upper portion of the pattern is suppressed. Therefore, as shown in FIG. 1(d), when the heating treatment is carried out in [step C], in the first resist pattern, a region 2a in which the solubility of the first resist pattern in an organic solvent is lowered, and a region 2b which has the solubility of the first resist pattern in an organic solvent are formed.

Step D

Step D is a step of developing the covered first resist pattern with an organic solvent and removing a region other than the region, in which the solubility of the first resist pattern in the developing solution is changed, to form a second resist pattern.

In step C, as shown in FIG. 1(d), in the first resist pattern, a region 2a in which the solubility of the first resist pattern in an organic solvent is lowered, and a region 2b which has the solubility of the first resist pattern in an organic solvent are formed. Therefore, when a region (2b in FIG. 1(d)) other than the region, in which the solubility of the first resist pattern in the developing solution is changed, is removed, the first resist pattern can be formed into a finer split pattern.

The organic solvent contained in the organic solvent used in the development may be appropriately selected from known organic solvents which can dissolve the solvent-containing solution 4, the layer 3 containing an acid or a thermoacid generator, and the region 2b having solubility in the organic solvent. Specific examples of the organic solvent include ketone solvents, ester solvents, and nitrile solvents. As an ester solvent, butyl acetate is preferable. As a ketone solvent, methyl amyl ketone (2-heptanone) is preferable.

A ketone solvent is an organic solvent containing C—C(=O)—C within the structure thereof. An ester solvent is an organic solvent containing C—C(=O)—O—C within the structure thereof. An alcohol solvent is an organic solvent containing an alcoholic hydroxy group within the structure thereof and an "alcoholic hydroxy group" refers to a hydroxy group bonded to a carbon atom of an aliphatic hydrocarbon group. An amide solvent is an organic solvent containing an amide group within the structure thereof. An ether solvent is an organic solvent containing C—O—C within the structure thereof. Some organic solvents have a plurality of the functional groups which characterizes the aforementioned solvents within the structure thereof. In such a case, the organic solvent can be classified as any kind of the solvent having the characteristic functional group which the organic solvent has. For example, diethylene glycol monomethylether can be classified as either an alcohol solvent or an ether solvent in the above classification. Further, a hydrocarbon solvent consists of a hydrocarbon, and does not have any substituent, a group or atom other than a hydrogen atom and a hydrocarbon group.

As specific examples of each solvent, examples of ketone solvents include 1-octanone, 2-octanone, 1-nonanone, 2-nonanone, acetone, 4-heptanone, 1-hexanone, 2-hexanone, diisobutyl ketone, cyclohexanone, methylcyclohexanone, phenylacetone, methyl ethyl ketone, methyl isobutyl ketone, acetylacetone, acetonylacetone, ionone, diacetonylalcohol, acetylcarbinol, acetophenone, methyl naphthyl ketone, isophorone, propylenecarbonate, γ-butyrolactone and methyl amyl ketone (2-heptanone).

Examples of ester solvents include methyl acetate, butyl acetate, ethyl acetate, isopropyl acetate, amyl acetate, isoamyl acetate, ethyl methoxyacetate, ethyl ethoxyacetate, propylene glycol monomethyl ether acetate, ethylene glycol monoethyl ether acetate, ethylene glycol monopropyl ether acetate, ethylene glycol monobutyl ether acetate, ethylene glycol monophenyl ether acetate, diethylene glycol monomethyl ether acetate, diethylene glycol monopropyl ether acetate, diethylene glycol monoethyl ether acetate, diethylene glycol monophenyl ether acetate, diethylene glycol monobutyl ether acetate, diethylene glycol monoethyl ether acetate, 2-methoxybutyl acetate, 3-methoxybutyl acetate, 4-methoxybutyl acetate, 3-methyl-3-methoxybutyl acetate, 3-ethyl-3-methoxybutyl acetate, propylene glycol monomethyl ether acetate, propylene glycol monoethyl ether acetate, propylene glycol monopropyl ether acetate, 2-ethoxybutyl acetate, 4-ethoxybutyl acetate, 4-propoxybutyl acetate, 2-methoxypentyl acetate, 3-methoxypentyl acetate, 4-methoxypentyl acetate, 2-methyl-3-methoxypentyl acetate, 3-methyl-3-methoxypentyl acetate, 3-methyl-4-methoxypentyl acetate, 4-methyl-4-methoxypentyl acetate, propylene glycol diacetate, methyl formate, ethyl formate, butyl formate, propyl formate, ethyl lactate, butyl lactate, propyl lactate, ethyl carbonate, propyl carbonate, butyl carbonate, methyl pyruvate, ethyl pyruvate, propyl pyruvate, butyl pyruvate, methyl acetoacetate, ethyl acetoacetate, methyl propionate, ethyl propionate, propyl propionate, isopropyl propionate, methyl 2-hydroxypropionate, ethyl 2-hydroxypropionate, methyl-3-methoxypropionate, ethyl-3-methoxypropionate, ethyl-3-ethoxypropionate and propyl-3-methoxypropionate.

Examples of nitrile solvents include acetonitrile, propionitrile, valeronitrile, butyronitrile and the like.

If necessary, a known surfactant may be combined with the organic developing solution as an additive.

The developing treatment using the organic developing solution can be carried out by known developing methods. Examples of the known developing methods include a method in which the support is immersed in the developing solution for a predetermined time (a dip method), a method in which the developing solution is piled up on the surface of the support by surface tension and maintained for a predetermined time (a puddle method), a method in which the developing solution is sprayed onto the surface of the support (spray method), and a method in which the developing solution is continuously ejected from a developing solution ejecting nozzle while scanning at a constant rate to apply the developing solution to the support while rotating the support at a constant rate (dynamic dispense method).

Before drying is carried out after the above developing treatment, rinse treatment can be performed using a rinse liquid containing an organic solvent. When the rinse treatment is performed, good pattern can be formed.

As the organic solvent used for the rinse liquid, among the aforementioned organic solvents contained in the organic developing solution, those which hardly dissolves the resist pattern can be appropriately selected and used. In general, at least one solvent selected from the group consisting of hydrocarbon solvents, ketone solvents, ester solvents, alcohol solvents, amide solvents and ether solvents is used. Among these, at least one solvent selected from the group consisting of hydrocarbon solvents, ketone solvents, ester solvents, alcohol solvents and amide solvents is preferable, more preferably at least one solvent selected from the group consisting of alcohol solvents and ester solvents, and an alcohol solvent is particularly preferable.

The alcohol solvent used for the rinse liquid is preferably a monohydric alcohol having 6 to 8 carbon atoms, and the monohydric alcohol may be linear, branched or cyclic. Specific examples thereof include 1-hexanol, 1-heptanol, 1-octanol, 2-hexanol, 2-heptanol, 2-octanol, 3-hexanol, 3-heptanol, 3-octanol, 4-octanol and benzyl alcohol. Among these, 1-hexanol, 2-heptanol and 2-hexanol are preferable, and 1-hexanol and 2-hexanol are more preferable.

These organic solvents can be used individually, or at least 2 solvents may be mixed together. Further, an organic solvent other than the aforementioned examples or water may be mixed together. However, in consideration of the development characteristics, the amount of water within the rinse liquid, based on the total amount of the rinse liquid is preferably 30% by weight or less, more preferably 10% by weight or less, still more preferably 5% by weight or less, and particularly preferably 3% by weight or less.

If necessary, the organic developing solution may have a conventional additive blended. Examples of the additive include surfactants. As the surfactant, the same surfactants as those described above can be mentioned, and a non-ionic surfactant is preferable, and a fluorine surfactant or a silicon surfactant is more preferable.

When a surfactant is added, the amount thereof is generally 0.001% by weight to 5% by weight, preferably 0.005% by weight to 2% by weight, and more preferably 0.01% by weight to 0.5% by weight, based on the total amount of the rinse liquid.

The rinse treatment (washing treatment) using the rinse liquid can be conducted by a conventional rinse method. Examples of the rinse method include a method in which the rinse liquid is continuously applied to the support while rotating it at a constant rate (rotational coating method), a method in which the support is immersed in the rinse liquid for a predetermined time (dip method), and a method in which the rinse liquid is sprayed onto the surface of the support (spray method).

According to the method of forming a resist pattern (I) of the present invention, a fine pattern obtained by dividing the first resist pattern, so-called a split pattern, can be satisfactorily formed.

The reason is considered as follows.

Since the method of forming a resist pattern (I) according to the present invention includes the [step B1], the action of acid in the first layer formed on the upper surface of the first resist pattern is suppressed, and the action of acid in the first layer formed on the side surface of the first resist pattern is exhibited, so that it is possible to control the solubility of each of the central portion and side wall portion of the first resist pattern in a developing solution. Therefore, it is considered that satisfactory pattern separation can be obtained.

Further, in the method of forming a resist pattern (I) according to the present invention, when a predetermined solvent or polymeric compound is employed as the solvent or polymeric compound contained in the first layer and the layer composed of the solvent, it is considered that it is possible to prevent the first resist pattern from being dissolved and to prevent the first layer and the layer composed of the solvent from being entirely mixed. In addition, it is considered that, in the organic solvent development in [step D], the solubility thereof in an organic solvent can be made good, and thus a desired split pattern can be obtained.

Second Embodiment

Method of Forming a Resist Pattern (II)

The method of forming a resist pattern according to the second embodiment of the present invention (hereafter, sometimes referred to as "method of forming a resist pattern (II)") includes a step A in which a positive resist composition is applied to a substrate to form a positive resist film, the positive resist film is exposed and the resist film is subjected to an alkali development to form a first resist pattern; a step B in which a solution containing an acid or a thermoacid generator is applied to the substrate whereon the first resist pattern is formed, so as to cover the first resist pattern, to form a structure having the first resist pattern and a first layer covering the first resist pattern; a step C in which the structure is heated and the solubility of the first resist pattern in an organic solvent is changed under action of the acid or under action of acid generated from the thermoacid generator; a step D in which the structure after heating is developed with the organic solvent to remove a region of the first resist pattern other than the region of the first resist pattern where the solubility in the organic solvent is changed, so as to form a second resist pattern; and a step E in which a pattern reversing composition containing an organic solvent that does not dissolve the second resist pattern is applied to form a pattern reversing film, and the pattern reversing film is subjected to an alkali development using an alkali developing solution to remove the second resist pattern and conduct patterning of the pattern reversing film, so as to form a third pattern.

Hereinbelow, the method of forming a resist pattern (II) according to the present invention will be described, with reference to the drawings.

Step A

Step A is a step of forming a positive resist film, exposing the positive resist film, and subjecting the positive resist film to an alkali development to form a first resist pattern. In the step A, as shown in FIG. 2(A), a first resist pattern 1P' is formed on a substrate 1'. The step A can be performed in the same manner as in the step A of the method of forming a resist pattern (I) according to the first embodiment described above.

Step B

In the step B, a solution containing an acid or a thermoacid generator is applied to cover the first resist pattern, so as to form a first layer. In the step B, as shown in FIG. 2(B), a first layer 2' is formed to cover the first resist pattern 1P' formed in the step A.

The first layer formed in the step B by applying a solution containing an acid or a thermoacid generator can act on the first resist pattern surface and change the solubility of the first resist pattern surface in a developing solution during the later step C. The step B can be performed in the same manner as in the step B of the method of forming a resist pattern (I) according to the first embodiment described above.

[Optional Step; Step B1]

In the method of forming a resist pattern (II) of the present invention, it is preferable to further include a [step B1] after the [step B].

The step B1 is a step in which a solution containing a solvent is applied to cover the first layer.

Figure 2:
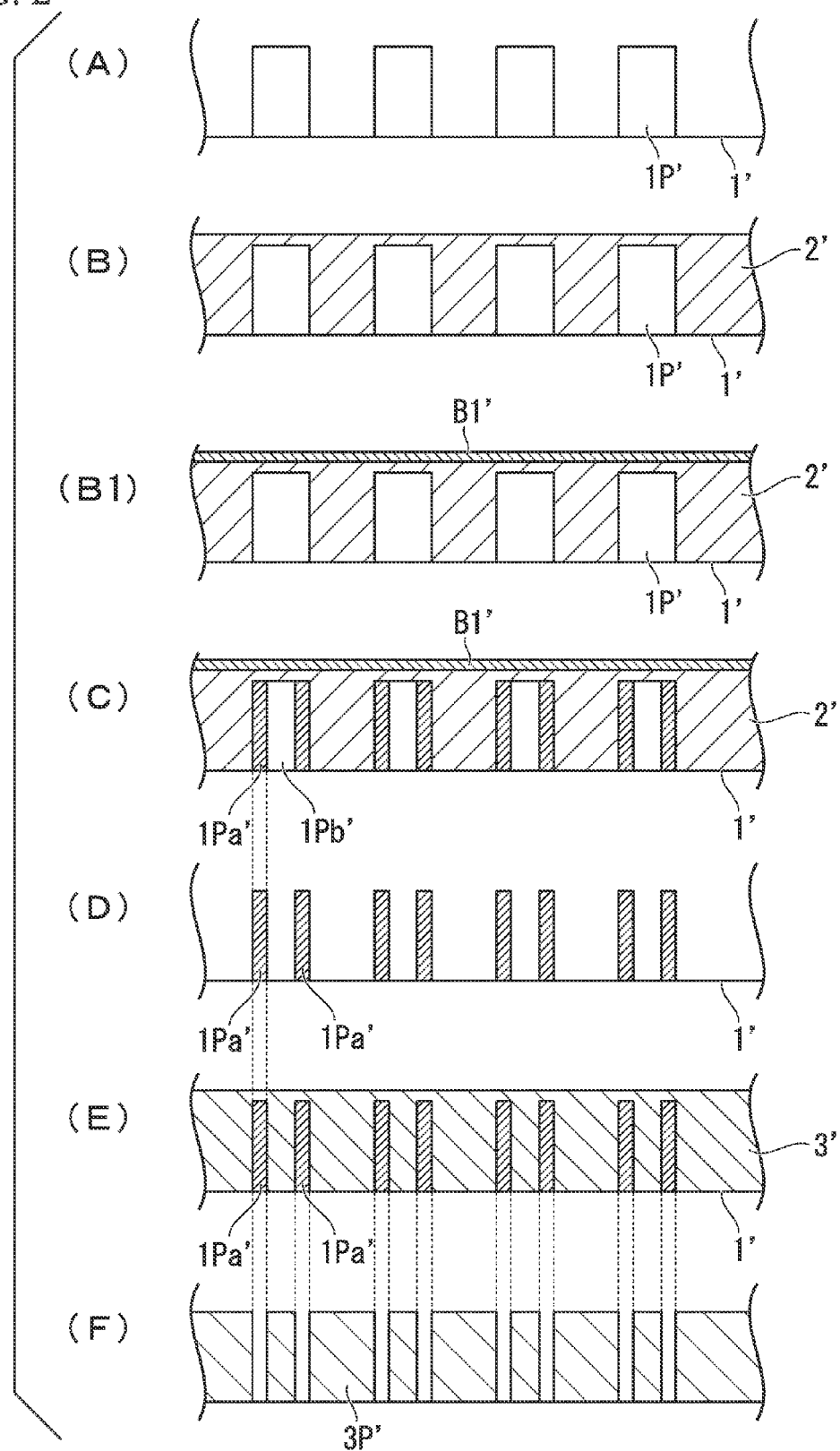
FIG. 2 shows an example of schematic steps of the method of forming a resist pattern (II) according to the present invention.

As shown in FIG. 2(B1), a solution consisted of a solvent is applied to cover the first layer 3, so as to form a layer B1'.

The solution consisted of a solvent is applied, in order to control the action of the acid contained in the first layer formed in the step B described above. The solution consisted of a solvent is applied to cover the first layer 2', however the solution can be partly mixed with the upper portion of the first layer.

The step B1 can be performed in the same manner as in the step B1 of the method of forming a resist pattern (I) according to the first embodiment described above.

Step C

Step C is a step in which the structure having the first resist pattern which is formed in the step A to B (or in the step A to B1) is heated, and the solubility of the first resist pattern in a developing solution is changed under action of the acid contained in the first layer described above. As the heating process, for example, a method of heating at 90 to 110° C. for 50 to 120 seconds can be adopted.

In the step C, as shown in FIG. 2(C), the solubility of the first resist pattern surface in a developing solution changes, and a developing solution-insoluble region 1Pa' can be formed.

In the step A, the first resist pattern 1P' is formed by an alkali development using a positive resist composition. That is, on the surface of the first resist pattern 1P', an alkali-insoluble region is formed.

In the step C, the surface of the first resist pattern 1P' can be deprotected, and the solubility of the first resist pattern 1P' surface can be decreased, by heating the structure having the first resist pattern obtained in the step A to B (or in the step A to B1).

When the solution consisted of a solvent is coated to cover the first layer 2 in the step B1, the acid of the first layer can act at the side wall portion of the first resist pattern, while the action of the acid of the first layer is suppressed in the upper portion of the first resist pattern. As a result, the solubility of both the first resist pattern center portion and the first resist pattern side wall portion is controlled. Hence, the pattern separation can be improved.

Step D

Step D is a step in which the first resist pattern covered is developed with the organic solvent to remove a region of the first resist pattern other than the region of the first resist pattern where the solubility in the organic solvent is changed, so as to form a second resist pattern.

In the step C, as shown in FIG. 2(C), the region 1Pa' exhibiting decreased solubility in the organic solvent and the region 1Pb' exhibiting solubility in the organic solvent are formed in the first resist pattern. Thus, the split pattern that is finer than the first resist pattern can be formed by removing the region (1Pb' in FIG. 2(C)) other than the region of the first resist pattern where the solubility in the developing solution is changed.

Further, in the step D, the first layer 2' can be also removed by the development, and thus the split pattern finer than the first resist pattern can be formed.

The step D can be performed in the same manner as in the step D of the method of forming a resist pattern (I) according to the first embodiment described above.

Step E

In the step E, a pattern reversing composition containing an organic solvent that does not dissolve the second resist pattern is applied to the substrate to form a pattern reversing film, and the pattern reversing film is subjected to an alkali development to remove the second resist pattern and conduct patterning of the pattern reversing film, so as to form a third pattern.

As shown in FIG. 2(E), a pattern reversing composition containing an organic solvent that does not dissolve the second resist pattern is applied to cover the second resist pattern 1Pa' obtained in the step A to D, so as to form a pattern reversing film 3'.

<Pattern Reversing Composition>

The pattern reversing composition used in the method of forming a resist pattern (II) comprises an organic solvent that does not dissolve the first resist pattern (hereinafter, referred to as "component (S')") and a base component (A") (hereinafter, referred to as "component (A")") for forming the pattern reversing film.

By virtue of the component (S') included in the pattern reversing composition, dissolving of the first resist pattern by an organic solvent in the pattern reversing composition when applying the pattern reversing composition can be suppressed, thereby preventing deterioration of the shape of the first resist pattern, dissipation of the first resist pattern, and mixing which occur at an interface between the first resist pattern and the pattern reversing film.

<<Component (S')>>

The component (S) is an organic solvent that does not dissolve the first resist pattern.

The expression "does not dissolve the first resist pattern" in the component (S') means that that, when a resist composition is applied to a substrate, dried and a resist film having a film thickness of 0.2 µm is formed, the resist film is not dissipated or the film thickness is not markedly changed by immersing the resist film in an organic solvent for 60 minutes (preferably, the film thickness of the resist film does not become 0.16 µm or less).

As the component (S'), a solvent which does not dissolve the first resist pattern but is capable of dissolving the components of the pattern reversing composition can be used. Among these, in terms of the coatability on the substrate and the solubility of components such as the resin component and the like blended in the pattern reversing composition, an alcohol organic solvent and an ester organic solvent is preferable, and an ester organic solvent is more preferable.

Here, the term "ester organic solvent" refers to a compound containing C—C(=O)—O—C within the structure thereof. The term "alcohol organic solvent" refers to a solvent containing an alcoholic hydroxy group within the structure thereof and a compound in which at least one hydrogen atom within an aliphatic hydrocarbon has been substituted with a hydroxy group and is a liquid at normal temperature (room temperature) and normal pressure (atmospheric pressure). The structure of the main chain constituting the aforementioned aliphatic hydrocarbon may be a chain-like structure or a cyclic structure, or may include a cyclic structure within the chain-like structure, or may include an ether bond within the chain-like structure.

As the ester organic solvent, the same ester organic solvents as those described above in the explanation of the solvents contained in the organic developing solution can be used. Among these, butyl acetate and ethyl-3-ethoxypropionate is preferable.

As the alcohol organic solvent, a monohydric alcohol, a dihydric alcohol or a dihydric alcohol derivative is preferable.

Although it depends on the number of carbon atoms, as the monohydric alcohol, a primary or secondary monohydric alcohol is preferable, and a primary monohydric alcohol is particularly desirable.

The term "monohydric alcohol" refers to a compound in which a hydrocarbon compound composed of only carbon atom and hydrogen atom has one hydrogen atom substituted with a hydroxy group, and does not include polyhydric alcohol derivatives having two or more hydroxy groups. The hydrocarbon compound may have a chain-like structure or a ring structure.

The term "dihydric alcohol" refers to a compound in which the aforementioned hydrocarbon compound has two hydrogen atoms substituted with hydroxy groups, and does not include polyhydric alcohol derivatives having three or more hydroxy groups.

Examples of the dihydric alcohol derivative include compounds in which a dihydric alcohol has one hydroxy group substituted with a substituent (e.g., alkoxy group, alkoxyalkyloxy group or the like).

The boiling point of the alcohol organic solvent (under normal pressure) is preferably 80 to 250° C., and more preferably 90 to 220° C. In terms of coatability, stability of the composition during storage and the heat temperature in the bake treatment, the boiling point is most preferably 100 to 200° C.

Specific examples of the alcohol organic solvent having a chain-like structure include propylene glycol (PG), 1-butoxy-2-propanol (PGB), n-hexanol, 2-heptanol, 3-heptanol, 1-heptanol, 5-methyl-1-hexanol, 6-methyl-2-heptanol, 1-octanol, 2-octanol, 3-octanol, 4-octanol, 2-ethyl-1-hexanol, 2-(2-butoxyethoxy)ethanol, n-pentylalcohol, s-pentylalcohol, t-pentylalcohol, isopentylalcohol, isobutanol (also referred to as isobutylalcohol or 2-methyl-1-propanol; IBA), 2-ethylbutanol, neopentylalcohol, n-butanol, s-butanol, t-butanol, 1-propanol, 2-methyl-1-butanol, 2-methyl-2-butanol and 4-methyl-2-pentanol (MIBC).

Further, specific examples of those having a ring structure include cyclopentane methanol, 1-cyclopentylethanol, cyclohexanol, cyclohexane methanol (CM), cyclohexane ethanol, 1,2,3,6-tetrahydrobenzyl alcohol, exo-norborneol, 2-methylcyclohexanol, cycloheptanol, 3,5-dimethylcyclohexanol, and benzyl alcohol.

Among alcohol organic solvents, a monohydric alcohol or a dihydric alcohol derivative having a chain-like structure is preferable, 1-butoxy-2-propanol (PGB), isobutanol (also referred to as isobutyl alcohol or 2-methyl-1-propanol; IBA), 4-methyl-2-pentanol (MIBC), and n-butanol are preferable, and isobutanol (2-methyl-1-propanol) and 1-butoxy-2-propanol (PGB) are particularly desirable.

As the component (S') used in the pattern reversing composition, one type of solvent may be used, or two or more types of solvents may be used.

The amount of the component (S') is not particularly limited, and is appropriately adjusted to a concentration which enables coating of a coating solution to a substrate. For example, the component (S') is used in an amount such that the amount of the base component (component (A)) described below in the pattern reversing composition becomes within the range preferably from 0.5 to 20% by weight, and more preferably from 1.0 to 15% by weight.

Further, the pattern reversing composition may contain an organic solvent other than the component (S') (hereafter, referred to as "component (S")"), as long as the effects of using the component (S') are not impaired.

As the component (S"), a solvent capable of dissolving the components blended in the pattern reversing composition is preferable. Specifically, the same as the component (S) described above in relation to the resist material forming the first resist pattern can be mentioned.

The amount of the component (S") based on the combined total of all organic solvents is preferably 20% by weight or less, and more preferably 1 to 15% by weight.

There are no particular limitations on the overall amount used of organic solvent in the pattern reversing composition, and an amount that produces a liquid having a concentration that is suitable for application of the pattern reversing composition onto a substrate is used. For example, the organic solvent is used in an amount such that the solid content of the pattern reversing composition becomes within the range from 1 to 30% by weight.

<<Component (A")>>

The component (A1") is a base component that contributes to the formation of the pattern reversing film and a polymeric compound having a film-forming ability.

As the component (A"), it is preferable that a dissolution rate of the base component as measured along with the [Method of determining dissolution rate in alkali developing solution] stated below be 1.0 to 3.5 nm/s.

[Method of Determining Dissolution Rate in Alkali Developing Solution]

A pattern reversing composition is applied to a substrate such as silicon substrate or the like, using a spinner or the like, and a prebake treatment (PAB) or the like is conducted so as to form a pattern reversing film. Subsequently, the pattern reversing film is conducted alkali development as described above and determined the dissolution rate (an amount of thickness loss per unit time, unit: nm/s) using Nanospec (manufactured by Nanometrics Incorporated).

As shown in FIG. 2(E), the pattern reversing film 3' is also formed on the upper portion of the second resist pattern 1Pa'. In the step E, the second resist pattern 1Pa' is removed by development. By ensuring the solubility of the pattern reversing composition in an alkali developing solution within the above-mentioned range, the pattern reversing film 3' on the upper portion of the second resist pattern 1Pa' can be appropriately dissolved in the developing solution, and thus the second resist pattern can be satisfactorily removed.

Component (A"1)

A component (A") preferably contains a resin component (A"1) (hereafter, sometimes referred to as "component (A"1)").

As the component (A"1), a resin which includes a structural unit having a polar group can be used. By including the structural unit having a polar group, the solubility of the component (A"1) in the component (S') improves. Furthermore, by including the structural unit having a polar group, the component (A"1) exhibits a satisfactory solubility in an alkali developing solution.

Examples of the component (A"1) include a resin component containing a structural unit (a"1) having at least one polar group selected from the group consisting of a hydroxy group, a cyano group, a carboxy group, a base dissociable group, a group represented by following general formula (f2-0-1), a group represented by following general formula (f2-0-2) and a group represented by following general formula (f2-0-3).

[Chemical Formula 50]

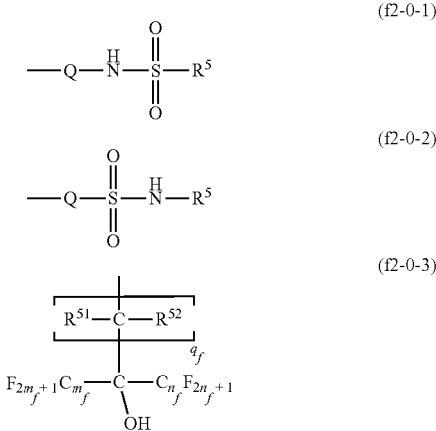

In general formula (f2-0-1), Q represents a divalent linking group or a single bond; and $R^5$ represents a fluorinated alkyl group. In general formula (f2-0-2), Q and $R^5$ are the same as defined above. In general formula (f2-0-3), each of $R^{51}$ and $R^{52}$ independently represents a hydrogen atom, a alkyl group of 1 to 5 carbon atoms, a fluorine atom or a fluorinated alkyl group of 1 to 5 carbon atoms; each of $m_f$ and $n_f$ independently represents an integer of 0 to 5 (with the provision that $m_f+n_f \geq 1$); and $q_f$ represents an integer of 0 to 5.

Structural Unit (a"1):

The structural unit (a"1) is a structural unit having at least one group selected from the group consisting of a hydroxy group, a cyano group, a carboxy group, a base dissociable group, a group represented by aforementioned general formula (f2-0-1), a group represented by aforementioned general formula (f2-0-2) and a group represented by aforementioned general formula (f2-0-3), as a polar group.

Base Dissociable Group

In the present invention, the term "base dissociable group" refers to an organic group which can be dissociated by the action of a base. Examples of the base include an alkali developing solution which is generally used in the fields of lithography. Therefore, a "base dissociable group" can be dissociated by the action of an alkali developing solution (e.g., a 2.38% by weight aqueous solution of tetramethylammonium hydroxide (TMAH) at 23° C.).

A base dissociable group dissociates due to hydrolysis caused by the action of an alkali developing solution. Therefore, a hydrophilic group is formed when the base dissociable group dissociates and the hydrophilicity of the component (A"1) is enhanced, and hence, the compatibility of the component (A"1) with the alkali developing solution is appropriately improved.

In the structural unit (a"1), the base dissociable group is not particularly limited as long as it is an organic group that satisfies the definition described above, and the base dissociable group may or may not contain a fluorine atom, although it preferably contains a fluorine atom. It is particularly desirable that the fluorine atom contained in the structural unit (a"1) is present only in the base dissociable group. If the base dissociable group contains a fluorine atom, since the fluorine atom contained in the base dissociable group is also dissociated from the structural unit (a"1) when the base dissociable group is dissociated by the action of an alkali developing solution, the affinity for the alkali developing solution is enhanced.

Specific examples of the base dissociable group include those represented by any one of general formulas (II-1) to (II-5) shown below.

In the present invention, the base dissociable group is preferably at least one base dissociable group selected from those represented by general formulas (II-1) to (II-5) shown below. In consideration of the excellent characteristic of exhibiting hydrophilicity during development, and ease in synthesis, a group represented by any one of general formulas (II-1), (II-4) or (II-5) shown below is particularly desirable.

[Chemical Formula 51]

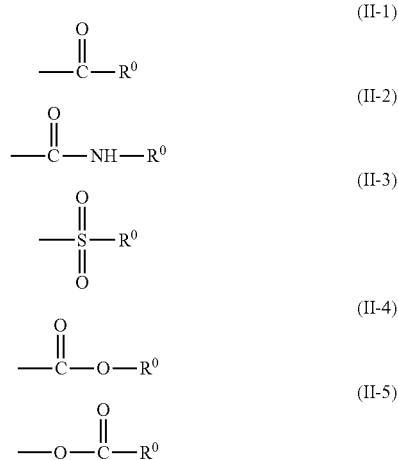

In the formulas, each $R^0$ independently represents an organic group which may have a fluorine atom.

In general formulas (II-1) to (II-5), each $R^0$ represents an organic group which may have a fluorine atom.

An "organic group" is a group containing at least one carbon atom.

The structure of $R^0$ may be linear, branched or cyclic, and is preferably linear or branched.

In $R^0$, the organic group preferably has 1 to 20 carbon atoms, more preferably 1 to 15 carbon atoms, still more preferably 1 to 10 carbon atoms, and most preferably 1 to 5 carbon atoms.

The fluorination ratio within $R^0$ is preferably 25% or more, more preferably 50% or more, and most preferably 60% or more.

The term "fluorination ratio" refers to the percentage (%) of the number of fluorine atoms based on the total number of hydrogen atoms and fluorine atoms contained within the organic group.

As a preferable example of $R^0$, a methyl group, an ethyl group and a fluorinated hydrocarbon group which may have a substituent can be given.

With respect to the fluorinated hydrocarbon group for $R^0$ which may have a substituent, the hydrocarbon group may be either an aliphatic hydrocarbon group or an aromatic hydrocarbon group, and an aliphatic hydrocarbon group is preferable.

An aliphatic hydrocarbon group refers to a hydrocarbon group having no aromaticity. The aliphatic hydrocarbon group may be either saturated or unsaturated, but in general, the aliphatic hydrocarbon group is preferably saturated.

As $R^0$, a fluorinated, saturated hydrocarbon group or a fluorinated, unsaturated hydrocarbon group is preferable, more preferably a fluorinated, saturated hydrocarbon group, and most preferably a fluorinated alkyl group.

Examples of fluorinated alkyl groups include groups in which part or all of the hydrogen atoms within the below described unsubstituted alkyl groups have been substituted with a fluorine atom. The fluorinated alkyl group may be either a group in which part of the hydrogen atoms within an unsubstituted alkyl group described below has been substituted with a fluorine atom, or a group in which all of the hydrogen atoms within an unsubstituted alkyl group described below has been substituted with a fluorine atom (i.e., a perfluoroalkyl group).

The unsubstituted alkyl group may be linear, branched or cyclic. Alternatively, the unsubstituted alkyl group may be a combination of a linear or branched alkyl group with a cyclic alkyl group.

The unsubstituted linear alkyl group preferably has 1 to 10 carbon atoms, and more preferably 1 to 8. Specific examples include a methyl group, an ethyl group, an n-propyl group, an n-butyl group, an n-pentyl group, an n-hexyl group, an n-heptyl group, an n-octyl group, an n-nonyl group and an n-decyl group.

The unsubstituted branched alkyl group preferably has 3 to 10 carbon atoms, and more preferably 3 to 8. As the branched alkyl group, a tertiary alkyl group is preferable.

As an example of an unsubstituted cyclic alkyl group, a group in which one hydrogen atom has been removed from a monocycloalkane or a polycycloalkane such as a bicycloalkane, tricycloalkane or tetracycloalkane can be given. Specific examples include monocycloalkyl groups such as a cyclopentyl group and a cyclohexyl group; and polycycloalkyl groups such as an adamantyl group, a norbornyl group, an isobornyl group, a tricyclodecyl group and a tetracyclododecyl group.

Examples of the combination of a linear or branched alkyl group with a cyclic alkyl group include groups in which a cyclic alkyl group as a substituent is bonded to a linear or branched alkyl group, and groups in which a linear or branched alkyl group as a substituent is bonded to a cyclic alkyl group.

Examples of substituents for the fluorinated hydrocarbon group include an alkyl group of 1 to 5 carbon atoms.

As the fluorinated alkyl group for $R^0$, a linear or branched fluorinated alkyl group is preferable. In particular, a group represented by general formula (III-1) or (III-2) shown below is desirable, and a group represented by general formula (III-1) is more preferable.

[Chemical Formula 52]

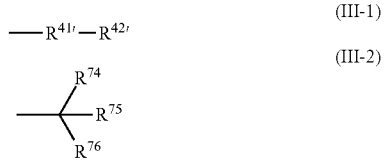

(III-1)

(III-2)

In general formula (III-1), $R^{41'}$ represents an unsubstituted alkylene group of 1 to 9 carbon atoms, and $R^{42'}$ represents a fluorinated alkyl group of 1 to 9 carbon atoms, provided that the total number of carbon atoms of $R^{41'}$ and $R^{42'}$ is no more than 10. In general formula (III-2), each of $R^{74}$ to $R^{76}$ independently represents a linear alkyl group of 1 to 5 carbon atoms, with the provision that at least one of $R^{74}$ to $R^{76}$ represents an alkyl group having a fluorine atom.

In general formula (III-1), the alkylene group for $R^{41'}$ may be linear, branched or cyclic, and is preferably linear or branched. Further, the number of carbon atoms within the alkylene group is preferably within a range of from 1 to 5.

As $R^{41'}$, a methylene group, an ethylene group or a propylene group is particularly desirable.

As $R^{42'}$, a linear or branched fluorinated alkyl group of 1 to 5 carbon atoms is preferable, and a perfluoroalkyl group is particularly desirable. Among perfluoroalkyl groups, a trifluoromethyl group (—$CF_3$), a tetrafluoroethyl group (—$C_2F_4H$) or —$C_2F_5$ is preferable.

In general formula (III-2), as the alkyl group for $R^{74}$ to $R^{76}$, an ethyl group or a methyl group is preferable, and a methyl group is particularly desirable. At least one of the alkyl groups for $R^{74}$ to $R^{76}$ is a fluorinated alkyl group, and all of the alkyl groups for $R^{74}$ to $R^{76}$ may be fluorinated alkyl groups.

"Group Represented by General Formula (f2-0-1)"

In aforementioned general formula (f2-0-1), Q represents a divalent linking group or a single bond.

Examples of divalent linking groups include linear, branched or cyclic alkylene groups of 1 to 8 carbon atoms such as a methylene group, an ethylene group, a propylene group, an isopropylene group, a cyclopropylene group, an n-butylene group, an isobutylene group, a pentene group, an isopentene group, a neopentene group, a cyclopentylene group, a cyclohexylene group, a cycloheptylene group and a cyclooctylene group. The divalent group for Q may contain a hetero atom, and examples of such divalent linking groups include an ether group, an ester group and a group in which at least one hydrogen atom and/or carbon atom within the aforementioned alkylene group has been substituted with a hetero atom. Among these, in terms of ease in synthesis, a linear alkylene group is preferable, and a methylene group is particularly desirable.

$R^5$ represents a fluorinated alkyl group. The fluorinated alkyl group is a group in which part or all of the hydrogen atoms of a linear, branched or cyclic alkyl group have been substituted with fluorine atoms.

The linear or branched alkyl group is preferably an alkyl group of 1 to 10 carbon atoms, more preferably an alkyl group of 1 to 8 carbon atoms, and still more preferably an alkyl group of 1 to 5 carbon atoms. Examples of alkyl groups include a methyl group, an ethyl group, a propyl group, an isopropyl group, an n-butyl group, an isobutyl group, a pentyl group, an isopentyl group and a neopentyl group. Among these, a methyl group is particularly desirable.

The cyclic alkyl group preferably has 4 to 12 carbon atoms, more preferably 5 to 10 carbon atoms, and most preferably 6 to 10 carbon atoms.

The fluorination ratio within the fluorinated alkyl group is preferably from 10 to 100%, more preferably from 30 to 100%, still more preferably from 50 to 100%, and is most preferably 100%, meaning groups in which all the hydrogen atoms have been substituted with fluorine atoms are the most preferred. Provided the fluorination ratio is at least 10%, the hydrophobicity of the pattern reversing film surface is enhanced, and the controllability of the dissolution rate in an alkali developing solution becomes excellent.

Among these examples, the fluorinated alkyl group for $R^5$ is preferably a linear or branched fluorinated alkyl group, more preferably a fluorinated alkyl group of 1 to 5 carbon atoms, and most preferably a perfluoroalkyl group in which all of the hydrogen atoms within the alkyl group have been substituted with fluorine atoms. Specific examples of such perfluoroalkyl groups include a trifluoromethyl group and a pentafluoroethyl group, and a trifluoromethyl group is particularly desirable.

"Group Represented by General Formula (f2-0-2)"

In general formula (f2-0-2), Q and $R^5$ are the same as defined for Q and $R^5$ in general formula (f2-0-1).

"Group Represented by General Formula (f2-0-3)"

In general formula (f2-0-3), each of $R^{51}$ and $R^{52}$ independently represents a hydrogen atom, an alkyl group of 1 to 5 carbon atoms, a fluorine atom or a fluorinated alkyl group of 1 to 5 carbon atoms.

As the alkyl group of 1 to 5 carbon atoms for $R^{51}$ and $R^{52}$, a linear or branched alkyl group is preferable, and specific examples thereof include a methyl group, an ethyl group, a propyl group, an isopropyl group, an n-butyl group, an isobutyl group, a tert-butyl group, a pentyl group, an isopentyl group and a neopentyl group. Among these, a methyl group is particularly desirable.

Examples of the fluorinated alkyl group for $R^{51}$ and $R^{52}$ include groups in which at least one hydrogen atom within the aforementioned alkyl group for $R^{51}$ and $R^{52}$ has been substituted with a fluorine atom.

Among these examples, as $R^{51}$ and $R^{52}$, a hydrogen atom is preferable, and it is particularly desirable that both $R^{51}$ and $R^{52}$ are hydrogen atoms.

Each of $m_f$ and $n_f$ independently represents an integer of 0 to 5 (with the provision that $m_f + n_f \geq 1$), and is preferably an integer of 1 to 3. In terms of superior dissolution rate in alkali developing solution, $m_f$ and $n_f$ are most preferably both 1.

$q_f$ is an integer of 0 to 5, preferably an integer of 0 to 3, more preferably 0 or 1, and most preferably 1.

As an example of a structural unit containing a group represented by aforementioned general formula (f2-0-3), a structural unit represented by general formula (f2-0-3-1) shown below can be given.

[Chemical Formula 53]

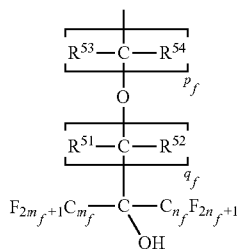

(f2-0-3-1)

In the formula, $R^{51}$, $R^{52}$, $m_f$, $n_f$, $q_f$ are the same as defined above. $R^{53}$ and $R^{54}$ independently represents a hydrogen atom, a alkyl group of 1 to 5 carbon atoms, a fluorine atom or a fluorinated alkyl group of 1 to 5 carbon atoms; $p_f$ represents an integer of 1 to 5.

In aforementioned general formula (f2-0-3-1), as $R^{53}$ and $R^{34}$, the same groups as those described above for $R^{51}$ and $R^{52}$ may be mentioned, respectively. Among these examples, a hydrogen atom is preferable, and it is particularly desirable that both $R^{53}$ and $R^{54}$ are hydrogen atoms.

$p_f$ is an integer of 1 to 5, preferably an integer of 1 to 3, more preferably 1 or 2, and most preferably 2.

Of these, as a polar group of the structural unit (a"1), it is preferable to be at least one selected from the group consisting of hydroxy group and groups represented by aforementioned general formula (f2-0-3).

Examples of the structural unit (a"1) includes a structural unit derived from a hydroxystyrene, a structural unit having a cyclic main chain (hereafter, referred to as "cyclic-main chain structural unit"), and a structural unit derived from an acrylate ester which may have the hydrogen atom bonded to the carbon atom on the α-position substituted with a substituent. Of these, a structural unit derived from hydroxystyrene, and a structural unit derived from an acrylate ester which may have the hydrogen atom bonded to the carbon atom on the α-position substituted with a substituent are preferable.

Further, in the present invention, a "cyclic-main chain structural unit" refers to a structural unit having a monocyclic or polycyclic ring structure, and at least one carbon atom within the ring structure, preferably two or more carbon atoms within the ring structure constitutes the main chain. By virtue of including a cyclic-main chain structural unit, the hydrophobicity of the pattern reversing film surface improves, and thus, the etching resistance also improves. It is presumed that such improvement in the etching resistance is due to the high carbon density of the cyclic main chain.

Examples of the cyclic-main chain structural unit includes a structural unit derived from a polycycloolefin, such as a structural unit derived from bicyclo[2.2.1]-2-heptene (norbornene), a structural unit derived from tetracyclo [4.4.0.1$^{2.5}$.1$^{7.10}$]-3-dodecene, or these structural units having a substituent within the ring structure.

Examples of the cyclic-main chain structural unit include structural units exemplified above, also having a group represented by general formula (f2-0-1), a group represented by general formula (f2-0-2) or a group represented by general formula (f2-0-3) as a substituent at a specific position on the ring structure.

Preferred examples of the structural unit (a"1) include a structural unit represented by the following general formula (a"11-1) (hereafter, referred to as "structural unit (a"11)").

Structural Unit (a"11)

As the structural unit (a"1), a structural unit represented by general formula (a"11-1) shown below (hereafter, referred to as "structural unit (a"11)") is preferable, because the solubility in the component (S') becomes excellent, a satisfactory solubility in an alkali developing solution is obtained, and the etching resistance becomes excellent.

[Chemical Formula 54]

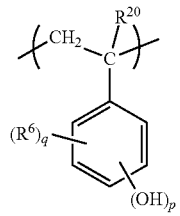

(a"11-1)

In the formula, $R^{20}$ represents a hydrogen atom or an alkyl group of 1 to 5 carbon atoms; $R^6$ represents an alkyl group of 1 to 5 carbon atoms; p represents an integer of 1 to 3; and q represents an integer of 0 to 2.

In the formula (a"11-1), specific examples of the alkyl group of 1 to 5 carbon atoms for $R^{20}$ include linear or branched alkyl groups such as a methyl group, an ethyl group, a propyl group, an isopropyl group, an n-butyl group, an isobutyl group, a tert-butyl group, a pentyl group, an isopentyl group and a neopentyl group.

As $R^{20}$, a hydrogen atom or a methyl group is preferable.

p represents an integer of 1 to 3, and is preferably 1.

The bonding position of the hydroxy group may be any of the o-position, m-position and p-position of the phenyl group. When p is 1, the p-position is preferable in terms of availability and low cost. When p is 2 or 3, a desired combination of the bonding positions can be used.

q represents an integer of 0 to 2. q is preferably 0 or 1, and most preferably 0 from industrial viewpoint.

As the alkyl group for $R^6$, the same alkyl groups as those for $R^{20}$ can be mentioned.

When q is 1, the bonding position of $R^6$ may be any of the o-position, the m-position and the p-position. When q is 2, a desired combination of the bonding positions can be used. Here, the plurality of the $R^6$ group may be the same or different from each other.

As the structural unit (a"11), one type of structural unit may be used alone, or two or more types of structural units may be used in combination.

In the component (A"1), the amount of the structural unit (a"11) based on the combined total of all structural units constituting the component (A) is preferably 40 to 75 mol %, more preferably 50 to 70 mol %, and still more preferably 55 to 65 mol %.

When the amount of the structural unit (a"11) is at least as large as the lower limit of the above-mentioned range, a desired solubility in alkali solution can be obtained using a pattern reversing composition prepared from the structural unit (a"11). On the other hand, when the amount of the structural unit (a"11) is no more than the upper limit of the above-mentioned range, a good balance can be achieved with the other structural units.

Structural Unit (a"2)

The component (A"1) may include a structural unit other than the structural unit (a"1) (hereafter, referred to as "structural unit (a"2)"), as long as the effects of the present invention are not impaired.

As the structural unit (a"2), any other structural unit which cannot be classified as the above structural unit (a"1) can be used without any particular limitation, and any of the multitude of conventional structural units used within resist resins for ArF excimer lasers or KrF excimer lasers (and particularly for ArF excimer lasers) can be used.

Examples of the structural unit (a"2) includes a structural unit derived from styrene, the structural unit (a1) stated above, the structural unit (a4) stated above, a structural unit derived from polycycloolefin having no substituent, and a structural unit derived from polycycloolefin having an aliphatic polycyclic group as a substituent.

Examples of the structural unit derived from polycycloolefin having no substituent includes bicyclo[2.2.1]-2-heptene (norbornene), and tetracyclo[4.4.0.12.5.1.7.10]-3-dodecene.

Examples of the structural unit derived from polycycloolefin having an aliphatic polycyclic group as a substituent includes the structural unit derived from polycycloolefin having no substituent, further having a polycyclic group, as a substituent, such as a tricyclodecanyl group, an adamantyl group and a tetracyclododecanyl group on the ring structure.

Among these examples, as the structural unit (a"2), a structural unit derived from styrene and the structural unit (a1) described above are preferable in terms of adjustable solubility in an alkali developing solution.

Further, it is preferable that the component (A"1) is a resin having a structural unit derived from styrene as the structural unit (a"2) (hereafter, referred to as "structural unit (a"21)"), as well as the structural unit (a"1).

By virtue of including the structural unit (a"21) as a structural unit (a"2), the solubility in an alkali developing solution be adjustable. Further, heat resistance and etching resistance of the pattern reversing film improves.

Specific examples of the structural unit (a"21) include the structural units represented by general formula (a"21-1) shown below.

[Chemical Formula 55]

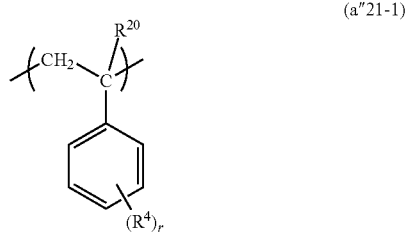

(a"21-1)

In the formula, $R^{20}$ is the same as defined above; $R^4$ represents an alkyl group of 1 to 5 carbon atoms; and r represents an integer of 0 to 3.

In general formula (a"21-1), $R^{20}$ is the same as defined above for $R^{20}$ in the aforementioned general formula (a"11-1).

In the formula (a"21-1), as the alkyl group for $R^4$, the same alkyl groups as those for $R^6$ in the aforementioned formula (a"11-1) can be mentioned.

r represents an integer of 0 to 3, preferably 0 or 1, and most preferably 0 in terms of industry.

When r represents 1, the substitution position of $R^4$ may be any of o-position, m-position or p-position of the phenyl group. When r is 2 or 3, a desired combination of the bonding positions can be used. Here, the plurality of the $R^4$ group may be the same or different from each other.

As the structural unit (a"21), one type of structural unit may be used alone, or two or more types of structural units may be used in combination.

In the component (A"1), the amount of the structural unit (a"21) based on the combined total of all structural units constituting the component (A) is preferably 10 to 25 mol %, more preferably 10 to 20 mol %, and still more preferably 10 to 15 mol %.

When the amount of the structural unit (a"21) is at least as large as the lower limit of the above-mentioned range, a desired solubility in alkali solution can be obtained using a pattern reversing composition prepared from the structural unit (a"21). On the other hand, when the amount of the structural unit (a"21) is no more than the upper limit of the above-mentioned range, a good balance can be achieved with the other structural units.

Further, the component (A"1) can include a resin having the structural unit (a1) described above, in addition to the structural unit (a"1), or in addition to the structural unit (a"1) and the structural unit (a"21).

By virtue of including the structural unit (a1) as a structural unit (a"2), the solubility in an alkali developing solution becomes adjustable. Further, a reversing pattern having higher resolution and excellent shape can be formed.

Examples of the structural unit (a1) in the component (A"1) include a structural unit derived from an acrylate ester which may have the hydrogen atom bonded to the carbon atom on the α-position substituted with a substituent and contains an acid decomposable group which exhibits increased polarity by the action of acid (hereafter, sometimes referred to as "structural unit (a"22-1)"); or a structural unit derived from hydroxystyrene or a hydroxystyrene derivative in which at least a part of the hydrogen atom of the hydroxy group is protected with a substituent containing an acid decomposable group (hereafter, sometimes referred to as "structural unit (a"22-2)").

When the structural unit (a1) in the component (A"1) is the structural unit (a"22-1), a structural unit having an acid decomposable group represented by the general formula (a1-r-2) described above is preferable, and a structural unit having a group represented by the general formula (a1-r2-2) described above is more preferable.

When the structural unit (a1) in the component (A"1) is the structural unit (a"22-2), a structural unit having an acid decomposable group represented by the general formula (a1-r-1) described above (acetal-type acid dissociable group) is preferable.

Structural Unit (a"23)

Furthermore, it is preferable that the component (A"1) includes a structural unit having a silicon atom (a"23) as a structural unit (a"2). As the structural unit (a"23), structural units represented by general formula (a"23-1) shown below are preferred. By virtue of adopting a structural unit having a silicon atom, etching resistance of the pattern reversing film improves.

[Chemical Formula 56]

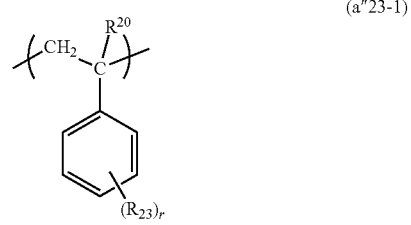

(a"23-1)

In the formula, $R^{20}$ is the same as defined above; $R^{23}$ represents an alkyl group in which part of the carbon atoms constituting the alkyl group has been substituted with silicon atom; and r represents an integer of 1 to 3.

Specific examples of the alkyl group of $R^{23}$ include linear or branched alkyl groups such as a methyl group, an ethyl group, a propyl group, an isopropyl group, an n-butyl group, an isobutyl group, a tert-butyl group, a pentyl group, an isopentyl group and a neopentyl group.

As $R^{23}$, an isopropyl group in which part of the carbon atoms has been substituted with a silicon atom.

As a structural unit having a silicon atom (a"23), a polyhedral oligomeric silsesquioxane (POSS) structure-containing structural unit is also preferable.

Polyhedral Oligomeric Silsesquioxane (POSS) Structure-Containing Structural Unit The component (A"1) preferably includes a polyhedral oligomeric silsesquioxane (POSS) structure-containing structural unit. Specific examples of the polyhedral oligomeric silsesquioxane (POSS) structure-containing structural unit include a structural unit represented by general formula (POSS-1) shown below.

[Chemistry Formula 57]

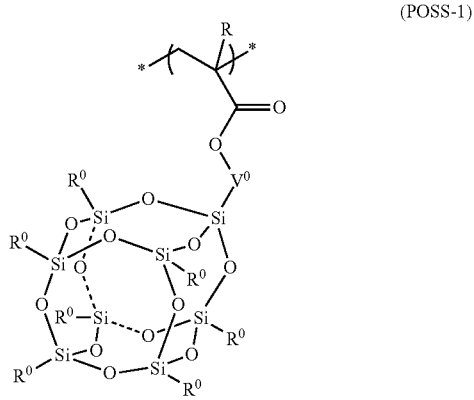

(POSS-1)

In the formula, R represents a hydrogen atom, an alkyl group of 1 to 5 carbon atoms or a halogenated alkyl group of 1 to 5 carbon atoms; $V^0$ represents a divalent hydrocarbon group which may have a substituent; $R^0$ represents a monovalent hydrocarbon group which may have a substituent, wherein the plurality of $R^0$ groups may be the same or different from each other. "*" represents a valence bond.

In the aforementioned formula (POSS-1), as the alkyl group of 1 to 5 carbon atoms for R, a linear or branched alkyl group of 1 to 5 carbon atoms is preferable, and specific examples thereof include a methyl group, an ethyl group, a propyl group, an isopropyl group, an n-butyl group, an isobutyl group, a tert-butyl group, a pentyl group, an isopentyl group and a neopentyl group. The halogenated alkyl group of 1 to 5 carbon atoms represented by R is a group in which part or all of the hydrogen atoms of the aforementioned alkyl group of 1 to 5 carbon atoms have been substituted with halogen atoms. Examples of the halogen atom include a fluorine atom, a chlorine atom, a bromine atom and an iodine atom, and a fluorine atom is particularly desirable.

As R, a hydrogen atom, an alkyl group of 1 to 5 carbon atoms or a fluorinated alkyl group of 1 to 5 carbon atoms is preferable, and a hydrogen atom or a methyl group is particularly desirable in terms of industrial availability.

In formula (POSS-1), the monovalent hydrocarbon group for $R^0$ preferably contains 1 to 20 carbon atoms, more preferably 1 to 10 carbon atoms, and still more preferably 1 to 8 carbon atoms. However, this number of carbon atoms does not include any carbon atoms within any of the substituents described below.

The monovalent hydrocarbon group for $R^0$ may be an aliphatic hydrocarbon group or an aromatic hydrocarbon group, but is preferably an aliphatic hydrocarbon group, and more preferably a monovalent aliphatic saturated hydrocarbon group (alkyl group).

More specific examples of this alkyl group include chain-like aliphatic hydrocarbon groups (linear or branched alkyl groups), and aliphatic hydrocarbon groups that include a ring within the structure.

The linear alkyl group preferably contains 1 to 8 carbon atoms, more preferably 1 to 5 carbon atoms, and still more preferably 1 to 3 carbon atoms. Specific examples include a methyl group, an ethyl group, an n-propyl group, an isopropyl group, an n-butyl group, an isobutyl group and an n-pentyl group. Among these, a methyl group, an ethyl group or an n-propyl group is preferable, a methyl group, an ethyl group or an isobutyl group is more preferable, and an ethyl group is most preferable.

The branched alkyl group preferably has 3 to 5 carbon atoms. Specific examples include an isopropyl group, an isobutyl group, a tert-butyl group, an isopentyl group and a neopentyl group, and an isopropyl group or a tert-butyl group is particularly desirable.

As examples of the hydrocarbon group containing a ring in the structure thereof, a cyclic aliphatic hydrocarbon group (a group in which 1 hydrogen atom has been removed from an aliphatic hydrocarbon ring), a group in which the cyclic aliphatic hydrocarbon group is bonded to the terminal of the aforementioned chain-like aliphatic hydrocarbon group, and a group in which the cyclic aliphatic hydrocarbon group is interposed within the aforementioned chain-like aliphatic hydrocarbon group, can be given.

The cyclic aliphatic hydrocarbon group preferably has 3 to 8 carbon atoms, and more preferably 4 to 6 carbon atoms. The cyclic aliphatic hydrocarbon group may be either a polycyclic group, or a monocyclic group. As the monocyclic group, a group in which 1 or more hydrogen atoms have been removed from a monocycloalkane of 3 to 6 carbon atoms is preferable. Examples of the monocycloalkane include cyclopentane and cyclohexane. As the polycyclic group, a group in which 1 or more hydrogen atom has been removed from a polycycloalkane of 7 to 12 carbon atoms is preferable. Examples of the polycycloalkane include adamantane, norbornane, isobornane, tricyclodecane and tetracyclododecane.

The chain-like aliphatic hydrocarbon group may have a substituent. Examples of the substituent include a fluorine atom, a fluorinated alkyl group of 1 to 5 carbon atoms, and an oxygen atom (=O).

The cyclic aliphatic hydrocarbon group may have a substituent. Examples of the substituent include an alkyl group of 1 to 5 carbon atoms, a fluorine atom, a fluorinated alkyl group of 1 to 5 carbon atoms, and an oxygen atom (=O).

In the case where the monovalent hydrocarbon group for $R^0$ is an aromatic hydrocarbon group, the aromatic hydrocarbon group is a monovalent hydrocarbon group having at least 1 aromatic ring.

The aromatic ring is not particularly limited, as long as it is a cyclic conjugated compound having (4n+2) π electrons, and may be either monocyclic or polycyclic. The aromatic ring preferably has 5 to 30 carbon atoms, more preferably 5 to 20, still more preferably 6 to 15, and most preferably 6 to 12. However, this number of carbon atoms does not include any carbon atoms within any of the substituents described below.

Examples of the aromatic ring include aromatic hydrocarbon rings, such as benzene, naphthalene, anthracene and phenanthrene; and aromatic hetero rings in which part of the carbon atoms constituting the aforementioned aromatic hydrocarbon rings has been substituted with a hetero atom. Examples of the hetero atom within the aromatic hetero rings include an oxygen atom, a sulfur atom and a nitrogen atom. Specific examples of the aromatic hetero ring include pyridine ring, thiophene ring, and the like.

Specific examples of the aromatic hydrocarbon group include a group in which one hydrogen atom has been removed from the aforementioned aromatic hydrocarbon ring or aromatic hetero ring (aryl group or heteroaryl group); a group in which one hydrogen atom has been removed from an aromatic compound having two or more aromatic rings (biphenyl, fluorene or the like); and a group in which one hydrogen atom of the aforementioned aromatic hydrocarbon ring or aromatic hetero ring has been substituted with an alkylene group (an arylalkyl group such as a benzyl group, a phenethyl group, a 1-naphthylmethyl group, a 2-naphthylmethyl group, a 1-naphthylethyl group, or a 2-naphthylethyl group).

The alkylene group which is bonded to the aforementioned aryl group or heteroaryl group preferably has 1 to 4 carbon atoms, more preferably 1 or 2 carbon atoms, and most preferably 1 carbon atom.

The aromatic hydrocarbon group may or may not have a substituent. Examples of the substituent include an alkyl group of 1 to 5 carbon atoms, a fluorine atom, a fluorinated alkyl group of 1 to 5 carbon atoms, and an oxygen atom (=O).

In aforementioned formula (POSS-1), the divalent hydrocarbon group for $V^0$ may be either an aliphatic hydrocarbon group or an aromatic hydrocarbon group. An "aliphatic hydrocarbon group" refers to a hydrocarbon group that has no aromaticity.

The aliphatic hydrocarbon group as the divalent hydrocarbon group for $V^0$ may be either saturated or unsaturated. In general, the aliphatic hydrocarbon group is preferably saturated.

As specific examples of the aliphatic hydrocarbon group, a linear or branched aliphatic hydrocarbon group, and an aliphatic hydrocarbon group containing a ring in the structure thereof can be given.

The linear or branched aliphatic hydrocarbon group preferably has 1 to 10 carbon atoms, more preferably 1 to 6, still more preferably 1 to 4, and most preferably 1 to 3.

As the linear aliphatic hydrocarbon group, a linear alkylene group is preferable. Specific examples thereof include a methylene group [—$CH_2$—], an ethylene group [—$(CH_2)_2$—], a trimethylene group [—$(CH_2)_3$—], a tetramethylene group [—$(CH_2)_4$—] and a pentamethylene group [—$(CH_2)_5$—].

As the branched aliphatic hydrocarbon group, branched alkylene groups are preferred, and specific examples include various alkylalkylene groups, including alkylmethylene groups such as —CH($CH_3$)—, —CH($CH_2CH_3$)—, —C($CH_3$)$_2$—, —C($CH_3$)($CH_2CH_3$)—, —C($CH_3$)($CH_2CH_2CH_3$)—, and —C($CH_2CH_3$)$_2$—; alkylethylene groups such as —CH($CH_3$)$CH_2$—, —CH($CH_3$)CH($CH_3$)—, —C($CH_3$)$_2CH_2$—, —CH($CH_2CH_3$)$CH_2$—, and —C($CH_2CH_3$)$_2$—$CH_2$—; alkyltrimethylene groups such as —CH($CH_3$)$CH_2CH_2$—, and —$CH_2$CH($CH_3$)$CH_2$—; and alkyltetramethylene groups such as —CH($CH_3$)$CH_2CH_2CH_2$—, and —$CH_2$CH($CH_3$)$CH_2CH_2$—. As the alkyl group within the alkylalkylene group, a linear alkyl group of 1 to 5 carbon atoms is preferable.

As examples of the hydrocarbon group containing a ring in the structure thereof, an alicyclic hydrocarbon group (a group in which two hydrogen atoms have been removed from an aliphatic hydrocarbon ring), a group in which the alicyclic hydrocarbon group is bonded to the terminal of the aforementioned chain-like aliphatic hydrocarbon group, and a group in which the alicyclic group is interposed within the aforementioned linear or branched aliphatic hydrocarbon group, can be given. As the linear or branched aliphatic hydrocarbon group, the same groups as those described above can be used.

The alicyclic hydrocarbon group preferably has 3 to 20 carbon atoms, and more preferably 3 to 12 carbon atoms.

The alicyclic hydrocarbon group may be either a polycyclic group or a monocyclic group. As the monocyclic aliphatic hydrocarbon group, a group in which 2 hydrogen atoms have been removed from a monocycloalkane is preferable. The monocycloalkane preferably has 3 to 6 carbon atoms, and specific examples thereof include cyclopentane and cyclohexane.

As the polycyclic group, a group in which 2 hydrogen atoms have been removed from a polycycloalkane is preferable, and the polycyclic group preferably has 7 to 12 carbon atoms. Examples of the polycycloalkane include adamantane, norbornane, isobornane, tricyclodecane and tetracyclododecane.

The aromatic hydrocarbon group is a hydrocarbon group having an aromatic ring.

The aromatic ring is not particularly limited, as long as it is a cyclic conjugated compound having (4n+2) π electrons, and may be either monocyclic or polycyclic. The aromatic ring preferably has 5 to 30 carbon atoms, more preferably 5 to 20, still more preferably 6 to 15, and most preferably 6 to 12. However, this number of carbon atoms does not include any carbon atoms within any of the substituents described below.

Examples of the aromatic ring include aromatic hydrocarbon rings, such as benzene, naphthalene, anthracene and phenanthrene; and aromatic hetero rings in which part of the carbon atoms constituting the aforementioned aromatic hydrocarbon rings has been substituted with a hetero atom. Examples of the hetero atom within the aromatic hetero rings include an oxygen atom, a sulfur atom and a nitrogen atom. Specific examples of the aromatic hetero ring include pyridine ring, thiophene ring, and the like.

Specific examples of the aromatic hydrocarbon group include a group in which two hydrogen atoms have been removed from the aforementioned aromatic hydrocarbon ring or aromatic hetero ring (arylene group or heteroarylene group); a group in which two hydrogen atoms have been removed from an aromatic compound having two or more aromatic rings (biphenyl, fluorene or the like); and a group in which one hydrogen atom of the aforementioned aromatic hydrocarbon ring or aromatic hetero ring has been substituted with an alkylene group (a group in which one hydrogen atom has been removed from the aryl group within the aforementioned arylalkyl group such as a benzyl group, a phenethyl group, a 1-naphthylmethyl group, a 2-naphthylmethyl group, a 1-naphthylethyl group, or a 2-naphthylethyl group, or a heteroarylalkyl group).

The alkylene group which is bonded to the aforementioned aryl group or heteroaryl group preferably has 1 to 4 carbon atoms, more preferably 1 or 2 carbon atoms, and most preferably 1 carbon atom.

Specific examples of structural unit represented by formula (POSS-1) are shown below. In the formulas shown below, $R^\alpha$ represents a hydrogen atom, a methyl group or a trifluoromethyl group.

[Chemical Formula 58]

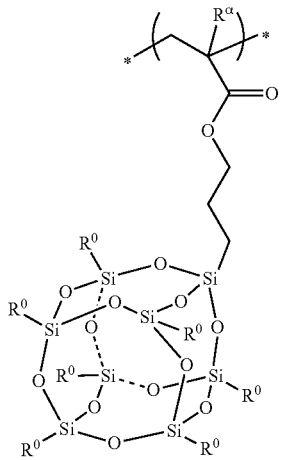

$R^0$ represents an ethyl group or an isobutyl group.

In the component (A"1), as the structural unit (a"1), one type of structural unit may be used alone, or two or more types of structural units may be used in combination.

In the component (A"1), the amount of the structural unit (a"1) based on the combined total of all structural units constituting the component (A"1) is preferably 20 to 50 mol %, more preferably 20 to 45 mol %, and still more preferably 20 to 40 mol %.

When the amount of the structural unit (a"1) is at least as large as the lower limit of the above-mentioned range, a desired solubility in alkali solution can be obtained using a pattern reversing composition prepared from the structural unit (a"1). Further, the resolution is improved, and a reversing pattern having an excellent shape can be obtained. On the other hand, when the amount is no more than the upper limit of the above-mentioned range, a good balance can be achieved with the other structural units.

In the component (A"1), the amount of the structural unit (a"2) based on the combined total of all structural units constituting the component (A"1) is preferably 1 to 50 mol %, more preferably 3 to 40 mol %, and still more preferably 3 to 35 mol %.

In the component (A"1), the amount of the structural unit (a"21) based on the combined total of all structural units constituting the component (A"1) is preferably 20 to 40 mol %, more preferably 20 to 35 mol %, and still more preferably 25 to 35 mol %.

In the component (A"1), the amount of the structural unit (a"23) based on the combined total of all structural units constituting the component (A"1) is preferably 1 to 30 mol %, more preferably 10 to 25 mol %, and still more preferably 15 to 25 mol %.

In the component (A"1), the amount of the structural unit containing (POSS) structure, based on the combined total of all structural units constituting the component (A"1), is preferably 1 to 30 mol %, more preferably 5 to 25 mol %, and still more preferably 5 to 20 mol %.

A component (A"1) preferably contains a resin component having the structural unit (a"1) (hereafter, referred to as "component (A"1-1)").

Preferable examples of the component (A"1-1) include a copolymer having the structural unit (a"1) and the structural unit (a"2). Preferable examples of the copolymer having the structural unit (a"1) and the structural unit (a"2) include a copolymer having the structural unit (a"11) and the structural unit (a"21); a copolymer having the structural unit (a"11) and the structural unit (a4); a copolymer having the structural unit (a"11) and the structural unit (a"23); and a copolymer having the structural unit (a"11) and the structural unit containing (POSS) structure.

As the component (A"1), one type may be used, or two or more types of compounds may be used in combination.

As the component (A"1), a copolymer that includes a combination of structural units such as that shown below is particularly desirable.

[Chemistry Formula 59]

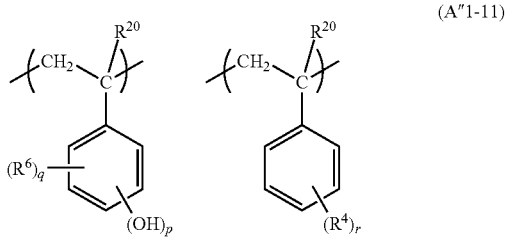

(A"1-11)

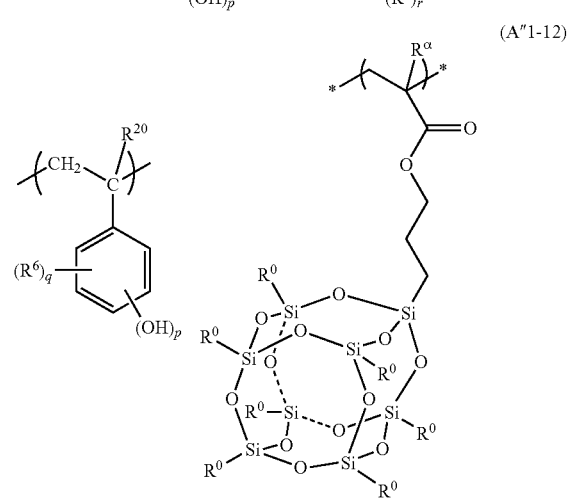

(A"1-12)

$R^0$ represents an ethyl group or an isobutyl group.

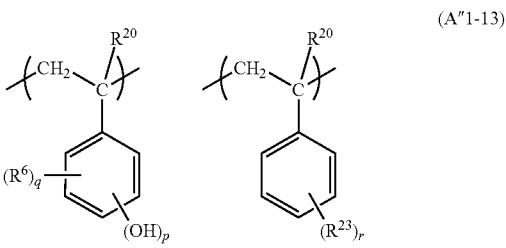

(A"1-13)

In general formulas (A"1-11) to (A"1-13), $R^{20}$, $R^6$, p and q are respectively the same as defined above for $R^{20}$, $R^6$, p and q in the aforementioned general formula (a"11-1). $R^4$ and r are respectively the same as defined for $R^4$ and r in the aforementioned formula (a"21-1). The plurality of $R^{20}$ may be the same or different from each other. $R^{23}$ and $R^\alpha$ are the same as defined above.

The weight average molecular weight (Mw) (the polystyrene equivalent value determined by gel permeation chromatography) of the component (A"1) is not particularly limited, but is preferably 1,000 to 50,000, more preferably 1,500 to 30,000, and most preferably 2,000 to 20,000. When the weight average molecular weight is no more than the upper limit of the above-mentioned range, the component exhibits a satisfactory solubility in an organic solvent as a resin component constituting the pattern reversing film. On the other hand, when the weight average molecular weight is at least as large as the lower limit of the above-mentioned range, dry etching resistance and the cross-sectional shape of the resist pattern becomes satisfactory.

Further, the dispersity (Mw/Mn) of the component (A"1) is not particularly limited, but is preferably 1.0 to 5.0, more preferably 1.0 to 3.0, and most preferably 1.0 to 2.5.

The component (A"1) can be obtained, for example, by a conventional radical polymerization or the like of the monomers corresponding with each of the structural units, using a radical polymerization initiator such as azobisisobutyronitrile (AIBN).

Further, when the polymer (A"1) has a cyclic-main chain structural unit, the polymer (A"1) can be synthesized, for example, by a method described in Japanese Unexamined Patent Application, First Publication No. 2006-291177.

Further, the component (A") may contain a base component (a resin or a low molecular weight compound), other than the component (A"1).

In the pattern reversing composition used in the present invention, as the component (A"), one type may be used, or two or more types of compounds may be used in combination.

In the pattern reversing composition, the amount of the component (A") can be appropriately adjusted depending on the thickness of the film to be formed, and the like.

<Other Components>

If desired, other miscible additives can also be added to the pattern reversing composition according to the present invention, in addition to the component (S') and the component (S") described above. Examples of such miscible additives include additive resins for improving the performance of the pattern reversing film, surfactants for improving the applicability, dissolution inhibitors, plasticizers, stabilizers, colorants, halation prevention agents, and dyes.

Of these, by including a dissolution inhibitor in combination with the base component (A"), the dissolution rate of the pattern reversing film in an alkali developing solution can be adjustable.

Dissolution Inhibitor

Preferable examples of a dissolution inhibitor includes an onium salt acid generator described above in the explanation of the component (B) blended in the resist composition. Of these, the compound represented by formula (b-1) is preferable in terms of the effect of dissolution inhibition in alkali developing solution and adjustability for desirable dissolution rate.

As the dissolution inhibitor, one type may be used alone, or two or more types may be used in combination.

In the pattern reversing composition, the amount of the dissolution inhibitor relative to 100 parts by weight of the component (A") is preferably 25 parts by weight or less, and more preferably 0.1 to 20 parts by weight, and still more preferably 0.5 to 18 parts by weight. When the amount of the dissolution inhibitor is within the above-mentioned range, the dissolution rate of the pattern reversing film in an alkali developing solution can be easily adjustable. Further, by virtue of the above-mentioned range, a uniform solution can be obtained and the storage stability becomes satisfactory.

In the step E, the pattern reversing composition is applied to cover the second resist pattern using a spinner, and a prebake treatment (PAB) is conducted, so as to form a pattern reversing film. Subsequently, the pattern reversing film is subjected to the alkali development to remove the second resist pattern and conduct patterning of the pattern reversing film, so as to form a third pattern.

Specifically, as shown in FIG. 2(F), the second resist pattern is removed, and thus the third pattern 3P' which has been formed by patterning the pattern reversing film.

In the step E, the developing treatment can be conducted with 0.1 to 10% by weight of aqueous tetramethylammonium hydroxide (TMAH) solution The developing time is preferably 5 to 40 seconds, and more preferably 10 to 30 seconds in terms of forming the third pattern satisfactorily.

In the method of forming a resist pattern (II) according to the present invention, by virtue of including the step A to the step E, a resist pattern having finer line width that is difficult to form by a general ArF positive resist patterning can be obtained. Specifically, in the general ArF positive resist patterning, the line width of the pattern formation is limited to around 80 nm. On the other hand, according to the present invention, a pattern having a line width of 80 nm or less, more specifically, a pattern having a line width of around 60 nm can be formed.

Further, when the pattern reversing composition includes a resin containing a structural unit having a silicon atom, the pattern formed exhibits excellent etching resistance.

Third Embodiment

Method of Forming Resist Pattern (III)

The method of forming a resist pattern according to the third embodiment of the present invention (hereafter, sometimes referred to as "method of forming a resist pattern (III)") includes a step A in which a positive resist composition is applied to a substrate to form a positive resist film, the positive resist film is exposed and the positive resist film is subjected to an alkali development to form a first resist pattern; a step B in which the first resist pattern is covered by coating a solution containing an acid or a thermoacid generator, so as to form a first layer, a step C in which a structure containing the first resist pattern formed in the step A to B is heated, and the solubility of the first resist pattern in a developing solution is changed under action of the acid contained in the first layer, and a step D in which the covered first resist pattern is developed with an organic solvent to remove a region of the first resist pattern other than the region of the first resist pattern where the solubility in the developing solution is changed, so as to form a second resist pattern.

The positive resist composition used in the step A includes an acid diffusion control agent component and the acid diffusion control agent component contains an acid having the dissociation constant (pKa) of 3.0 or more.

Hereinbelow, the method of forming a resist pattern (III) according to the present aspect will be described, with reference to the drawings.

Embodiment 3-1

Figure 3:
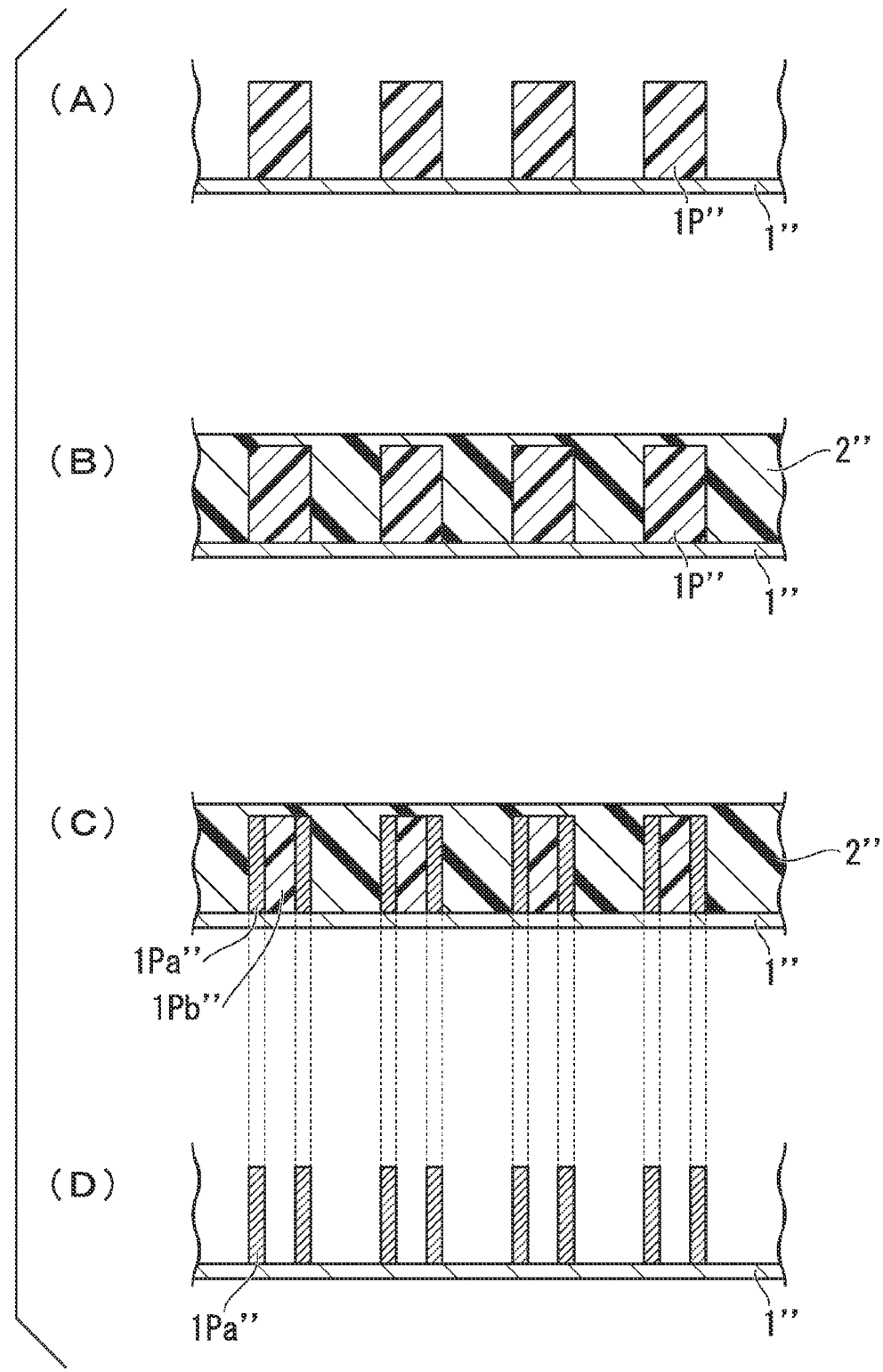
FIG. 3 shows schematic steps in the embodiment 3-1 of the method of forming a resist pattern (III) according to the present invention.

FIG. 3 shows schematic steps of the resist pattern forming method according to the first embodiment. FIGS. 3(A) to (D) show a cross-sectional view of the resist pattern.

In this embodiment, a positive resist composition comprising an acid diffusion control agent containing an acid having the acid dissociation constant (pKa) of 3.0 or more, and a base component (A) which exhibits increased solubility in an alkali developing solution under action of acid.

Firstly, as shown in FIG. 3(A), a resist pattern 1P" having a line and space pattern is formed on a substrate 1" using the positive resist composition (step A).

Subsequently, as shown in FIG. 3(B), the resist pattern 1P" is covered by coating a solution containing an acid or a thermoacid generator, so as to form a structure 3" composed of the first resist pattern 1P" and a first layer 2" covering the first resist pattern (step B).

Then, as shown in FIG. 3(C), the solubility of the first resist pattern 1P" surface in a developing solution changes by heating the structure 3" (step C).

Further, a development with an organic solvent is conducted to remove the region shown as 1Pb" in FIG. 3(C), so as to form a fine pattern in which the first resist pattern is split into line, space and line (hereafter, sometimes referred to as "split pattern") as shown in FIG. 3(D) (step D).

Step A

Step A is a step of applying a positive resist composition to a substrate to form a positive resist film, exposing the positive resist film, and subjecting the positive resist film to an alkali development, so as to form a first resist pattern. The step A can be performed in the same manner as in the step A of the method of forming a resist pattern (I) according to the first embodiment described above.

In the method of forming a resist pattern (III) according to the third embodiment, the positive resist composition includes an acid diffusion control agent component and the acid diffusion control agent component contains an acid having the acid dissociation constant (pKa) of 3.0 or more.

In the present embodiment, "the acid dissociation constant (pKa)" refers to a parameter generally used to show the acid strength of an objective substance. The pKa value shown in the present specification is a value determined at a temperature of 25° C. The pKa value can be determined by a conventional method. Alternatively, a calculated value determined by using a conventional software such as "ACD/Labs" (trade name; manufactured by Advanced Chemistry Development, Inc.) can be used.

In this embodiment, the acid diffusion control agent component contains preferably an acid having the acid dissociation constant (pKa) of 4.0 or more, and more preferably an acid having the pKa of 4.5 or more.

Further, the acid dissociation constant (pKa) is preferably 10 or less, and more preferably 8.0 or less.

A desired combination of the above upper limit and the lower limit can be used.

Examples of the acid diffusion control agent component include any of the acid diffusion control agent component (D) aforementioned in the first embodiment which includes an acid having the acid dissociation constant of 3.0 or more.

In the (D1) component, specific examples of preferable anion moieties for the component (d1-1) are shown below. The acid dissociation constant (pKa) of each acid generated from the compounds having these anions is also indicated.

[Chemical Formula 60]

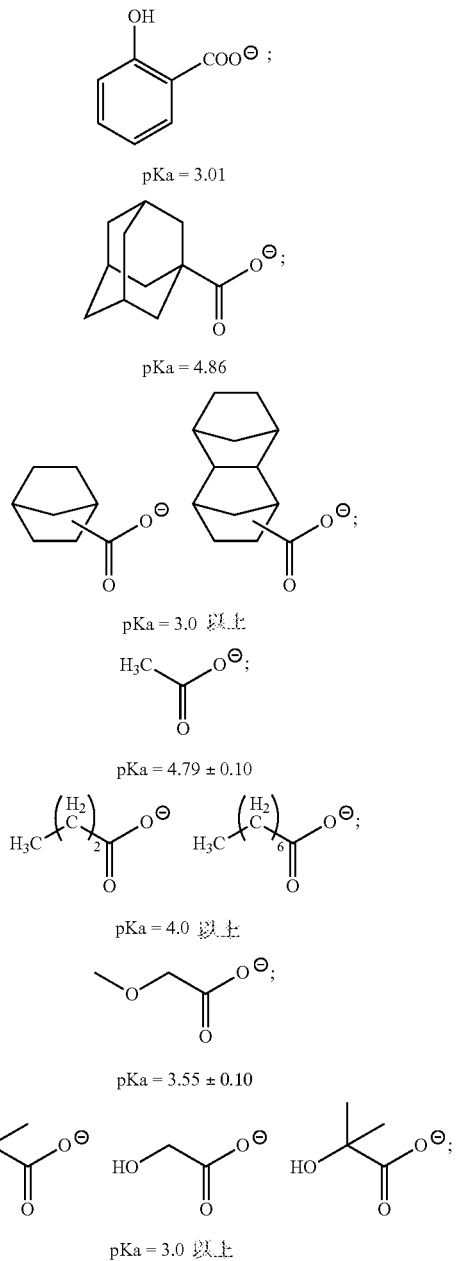

[Chemical Formula 61]

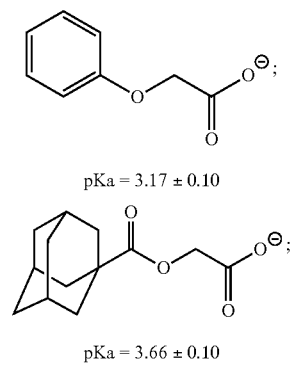

-continued pKa = 3.55 ± 0.10 pKa = 3.74 ± 0.10 pKa = 4.39 ± 0.10 pKa = 4.39 ± 0.10 pKa = 3.99 ± 0.20 pKa = 3.0 以上

In the (D1) component, specific examples of preferable anion moieties for the component (d1-2) are shown below. The acid dissociation constant (pKa) of each acid generated from the compounds having these anions is −1.0 to 10.0.

[Chemical Formula 62]

-continued $H_3C-SO_3^{\ominus}$  $H_3C\smallsetminus SO_3^{\ominus}$  $C_aH_{2a+1}SO_3^{\ominus}$ (a = 3 - 10)

In the component (D1), the acid dissociation constants (pKa) of the acids generated from the compounds having the anion moieties shown as preferable examples of the component (d1-3) are 3.0 to 10.0.

When the component (D2) is used as an acid diffusion control agent, as the component (D2), there is no particular limitation as long as the acid dissociation constant thereof is 3.0 or more, and it does not fall under the definition of the component (D1).

Among these, an aliphatic amine, particularly a secondary aliphatic amine or tertiary aliphatic amine having the acid dissociation constant (pKa) of 3.0 or more is preferable.

An aliphatic amine is an amine having one or more aliphatic groups, and the aliphatic groups preferably have 1 to 12 carbon atoms.

Examples of these aliphatic amines include amines in which at least one hydrogen atom of ammonia ($NH_3$) has been substituted with an alkyl group or hydroxyalkyl group of no more than 12 carbon atoms (i.e., alkylamines or alkylalcoholamines), and cyclic amines.

Examples of the cyclic amine include heterocyclic compounds containing a nitrogen atom as a hetero atom. The heterocyclic compound may be a monocyclic compound (aliphatic monocyclic amine), or a polycyclic compound (aliphatic polycyclic amine).

Further, as the component (D2), an aromatic amine may be used.

Step B

In the step B, a solution containing an acid or a thermoacid generator is applied to the substrate whereon the first resist pattern is formed to cover the first resist pattern, so as to obtain a structure having the first resist pattern and a first layer covering it.

The first layer formed in the step B by applying a solution containing an acid or a thermoacid generator is formed so as to contact with the first resist pattern surface. As a result, the solubility of the first resist pattern surface in a developing solution changes in the step C.

The first layer formed by applying a solution containing an acid or a thermoacid generator is soluble in an organic solvent used in an organic solvent developing process.

The coating film thickness of the first layer is determined such that the first layer does not change the solubility of the first resist pattern surface in an organic solvent. Such coating film thickness of the first layer relative to 1 part of the first resist pattern height is, for example, preferably 0.5 to 1.5 parts, more preferably 0.8 to 1.4 parts, and most preferably 0.9 to 1.2 parts.

The solution containing an acid or a thermoacid generator used in the step B is the same as the solution containing an acid or a thermoacid generator described above in the first embodiment.

Step C

In the step C, the structure is heated, and the solubility of the first resist pattern in an organic solvent is changed under action of the acid or under action of acid generated from the thermoacid generator. As the heating process, for example, a method of heating at 90 to 150° C. for 50 to 120 seconds can be adopted.

In the step C, as shown in FIG. 3(C), the solubility of the first resist pattern surface in an organic solvent changes, and an organic solvent-insoluble region 1Pa" can be formed.

In the step A, the first resist pattern 1P'" is formed by an alkali development using a positive resist composition. That is, the first resist pattern is alkali-insoluble.

In the step C, the structure having the first resist pattern obtained in the step A to B is heated, and thus the acid or acid generated from the thermoacid generator acts on the base component (A) on the surface of the first resist pattern 1P, so as to form an organic solvent-insoluble region 1Pa" wherein the solubility in an organic solvent is decreased. That is, the outside of the first resist pattern 1P'" becomes an organic solvent-insoluble region 1Pa", and the inside thereof becomes an organic solvent-soluble region 1Pb".

In FIG. 3(C), a width of the organic solvent-insoluble region 1Pa" (line width) or a width of the organic solvent-soluble region 1Pb" (space width) is adjusted by a composition of the positive resist composition (a base component (A), an acid generator or the like), acid strength of the acid or an acid generated from the thermoacid generator, a heating condition in the step D, and the like.

When difference in pKa between the acid or an acid generated from the thermoacid generator used in the step C, and the acid contained in the acid diffusion control agent included in the positive resist composition for forming the first resist pattern is large, the split pattern having narrow line width can be formed. Here, the term "line width of the split pattern" means the width of the organic solvent-insoluble region 1Pa" in the cross-sectional view of FIG. 3(D).

Step D

Step D is a step in which the structure after heating is developed with an organic solvent to remove a region of the first resist pattern other than the region of the first resist pattern where the solubility in the organic solvent is changed, so as to form a split pattern. In the step D, the organic solvent-insoluble region 1Pb" and the first layer 2" are removed by an organic solvent development.

As a result, a split pattern finer than the first resist pattern can be formed.

FIG. 3(D) shows a case that a split pattern having a line width:space width:line width ratio of about 1:1:1 is formed.

The organic solvent used in the step D is the same as defined for the organic solvents aforementioned in the first embodiment.

By the method of forming resist pattern according to the embodiment 3-1, the second resist pattern (a split pattern) split from the first resist pattern can be formed.

In the method of forming resist pattern according to the embodiment 3-1, by virtue of the acid diffusion control agent component contained in the positive resist composition for forming the first resist pattern in the step A containing the acid dissociation constant of 3.0 or more, the split pattern formed in the step D can be miniaturized and LWR can be lowered.

Further, by virtue of suppressing the excess deprotection on the surface of the first resist pattern, the split pattern formed in the step D can be miniaturized and LWR can be lowered.

Embodiment 3-2

Figure 4:
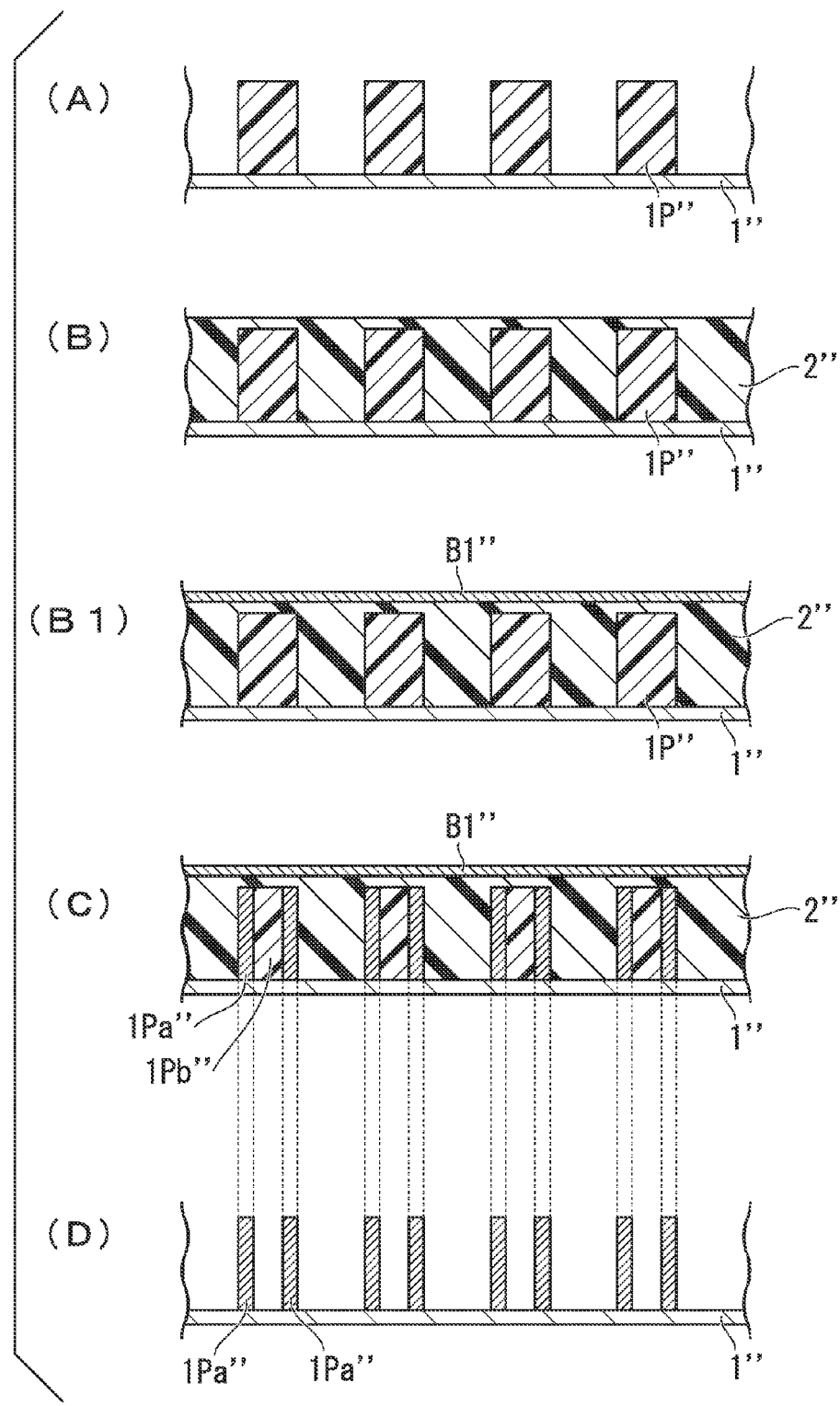
FIG. 4 shows schematic steps in the embodiment 3-2 of the method of forming a resist pattern (III) according to the present invention.

FIG. 4 shows schematic steps of the resist pattern forming method according to the embodiment 3-2. FIGS. 4(A) to (D) show a cross-sectional view. In this embodiment 3-2, a positive resist composition comprising an acid diffusion control agent containing an acid having the acid dissociation constant (pKa) of 3.0 or more, and a base component (A) which exhibits increased solubility in an alkali developing solution under action of acid.

Firstly as shown in FIG. 4(A), a resist pattern 1P'" having a line and space pattern is formed on a substrate 1" using the positive resist composition (step A).

Subsequently, as shown in FIG. 4(B), the resist pattern 1P'" is covered by coating a solution containing an acid or a thermoacid generator, so as to form a structure 3 composed of the first resist pattern 1P'" and a first layer 2" covering the first resist pattern (step B).

Subsequently, as shown in FIG. 4(B1), a solution containing an acid diffusion control agent is applied, so as to cover the structure 3 having the first resist pattern 1P'" and the first layer 2". As a result, as shown in FIG. 4(B1), a layer containing an acid diffusion control agent B1" is formed on the structure 3".

Then, as shown in FIG. 4(C), the solubility of the first resist pattern 1P'" surface in an organic solvent changes by heating the structure 3" and the layer containing the acid diffusion control agent B1".

Further, a development with an organic solvent is conducted to remove the region shown as 1Pb" in FIG. 4(C), so as to form a fine pattern in which the first resist pattern is split into line, space and line (hereafter, sometimes referred to as "split pattern") as shown in FIG. 4(D) (step D).

Step A and B

The step (A) and (B) shown in FIG. 4 can be performed in the same manner as in the step (A) and (B) in the aforementioned embodiment 3-1, respectively.

In the step (B) of the embodiment 3-1, the coating film thickness of the first layer is not particularly limited as long as at least a part of the first resist pattern is covered, and is, for example, preferably 0.5 to 2.0 parts relative to 1 part of the first resist pattern height, more preferably 0.8 to 1.6 parts, and most preferably 0.9 to 1.4 parts.

Step B1

The embodiment 3-2 has [step B1] after [step B].

The step B1 is a step in which a solution containing an acid diffusion control agent is applied to cover the first layer. The step B1 can be performed in the same manner as in the step B1 of the method of forming a resist pattern (I) according to the first embodiment described above.

As shown in FIG. 4(B1), a solution containing an acid diffusion control agent is applied, so as to cover the structure 3" having the first resist pattern 1P" and the first layer 2" covering it. As a result, as shown in FIG. 4(B1), a layer containing an acid diffusion control agent B1" is formed on the structure 3".

By virtue of forming the layer containing an acid diffusion control agent B1", act of the acid or an acid generated from the thermoacid generator contained in the first layer 2" formed in the [step B] on the base component (A) contained in the first resist pattern 1P" is weakened, especially at the upper portion of the first resist pattern 1P". The solution containing the acid diffusion control agent is applied to cover the first layer 2", however the solution can be partly mixed with the upper portion of the first layer.

By virtue of coating the solution containing the acid diffusion control agent to cover the first layer 2" in the step B1, the acid of the first layer which exists on the first resist pattern is suppressed to act on the base component (A) contained in the first resist pattern 1P", and the acid or an acid generated from the thermoacid generator contained in the first layer which exists on the side surface of the first resist pattern can act. Thus, the solubility of the first resist pattern in the top surface portion and side wall portion can be adjusted in a developing solution. As a result, the pattern can separate satisfactorily and an excellent split pattern can be formed.

Steps (C) and (D)

The step (C) and (D) shown in FIG. 4 can be performed in the same manner as in the step (C) and (D) in the aforementioned embodiment 3-1, respectively.

Other Embodiments

In the aforementioned embodiment 3-1 and the embodiment 3-2, explanation was given taking example of the case that a line and space pattern is formed. However, the present invention is not limited thereto, and a dot pattern, another desired graphic pattern or the like can be formed.

<<Second Aspect: Resist Pattern Splitting Agent>>

According to a second aspect of the present invention, there is provided a resist pattern splitting agent, which is used to cover a resist pattern and split the resist pattern, including at least: a solvent; and an acid or a thermoacid generator.

According to the resist pattern splitting agent of the present invention, a finer pattern can be formed by splitting (dividing) the formed resist pattern.

Descriptions of the resist pattern covered with the resist pattern splitting agent of the present invention and the resist composition used for forming this resist pattern are the same as the descriptions of the first resist pattern and the resist composition used for forming the first resist pattern in the method of forming a resist pattern (I) according to the first aspect of the present invention.

A description of the resist pattern splitting agent of the present invention is the same as the description of the solution containing an acid or a thermoacid generator used in the [step B] in the method of forming a resist pattern (I) according to the first aspect of the present invention.

That is, a description of a solvent contained in the resist pattern splitting agent of the present invention is the same as the description of the solvent (B). Preferably, the solvent contained in the resist pattern splitting agent contains a linear or branched monohydric alcohol having 1 to 10 carbon atoms. A description of the linear or branched monohydric alcohol having 1 to 10 carbon atoms is the same as the description of the solvent (B).

A description of an acid or a thermoacid generator contained in the resist pattern splitting agent of the present invention is the same as the description of the component (T0) or the component (T1).

Further, it is preferable that the resist pattern splitting agent of the present invention contains a polymeric compound in order to improve coating properties and such that it can be removed in the developing treatment after the splitting.

As the preferable polymeric compound contained in the resist pattern splitting agent of the present invention, the polymeric compound (Tp) is exemplified.

<<Third Aspect: Split Pattern Improving Agent>>

According to a third aspect of the present invention, there is provided a split pattern improving agent. The split pattern improving agent of the present invention is used to further cover a resist pattern after covering the resist pattern using the resist pattern splitting agent, and includes at least: an organic solvent; and an acid diffusion control agent.

A description of the split pattern improving agent of the present invention is the same as the description of the solvent-containing solution used in the [step B1] in the method of forming a resist pattern (I) according to the first aspect of the present invention.

That is, a description of a solvent contained in the split pattern improving agent of the present invention is the same as the description of the solvent (C). It is preferable that the split pattern improving agent contains an acid diffusion control agent and a polymeric compound. A description of the acid diffusion control agent is the same as the description of the acid diffusion control agent described in the [step B1].

Further, it is preferable that the polymeric compound contained in the split pattern improving agent of the present invention is the polymeric compound (Cp).

<<Fourth Aspect: Resist Pattern Splitting Material>>

According to a fourth aspect of the present invention, there is provided a resist pattern splitting material, including: the resist pattern splitting agent according to the second aspect; and the split pattern improving agent. Descriptions of the resist pattern splitting agent is the same as the resist pattern splitting agent described in the second aspect. As the split pattern improving agent, the same agent described above in the third aspect can be used.

When the resist pattern splitting agent according to the second aspect is used in combination with the split pattern improving agent according to the third aspect, satisfactory pattern separation (splitting) can be achieved. In addition, the overall mixing of the resist pattern splitting agent with the split pattern improving agent does not easily occur, and the resist pattern splitting agent and the split pattern improving agent can be removed in the developing step, so that the resist pattern splitting agent and the split pattern improving agent are also excellent in handling properties.

133

<<Fifth Aspect: Positive Resist Composition for Forming Split Pattern>>

A fifth aspect of the present embodiment is a positive resist composition for forming a split pattern, which is used in the method of forming a resist pattern according to the first aspect of the present invention, and the positive resist composition generating acid upon exposure and exhibiting increased solubility in a developing solution under action of acid, wherein the positive resist composition comprises an acid diffusion control agent, and the acid diffusion control agent contains an acid having an acid dissociation constant (pKa) of 3.0 or more.

The resist composition for forming a split pattern according to the fifth aspect of the present embodiment is the same as the resist composition described in the step A of the method of forming a resist pattern (III) according to the first aspect of the present invention.

The resist composition for forming a split pattern according to the present embodiment can be preferably used in the formation of a fine pattern, called a split pattern, which is formed by splitting the first resist pattern.

EXAMPLES

Hereinafter, the present invention will be described in more detail with reference to the following Examples. However, the present invention is not limited to these Examples.

Examples 1-1 to 1-30

Step A

<Preparation of Resist Composition>

100 parts by weight of polymeric compound (A)-1 below, 10 parts by weight of compound (B)-1 below, 7 parts by weight of compound (D)-1 below, 2 parts by weight of compound (F)-1 below (in the formula, l/m=23/77 (molar ratio), Mw=23100, and Mw/Mn=1.78), 2 parts by weight of salicylic acid, and 4000 parts by weight of a solvent (a mixed solvent of PGMEA/PGME/cyclohexanone (weight ratio: 45/30/25)) were mixed to prepare a resist composition.

[Chemical Formula 63]

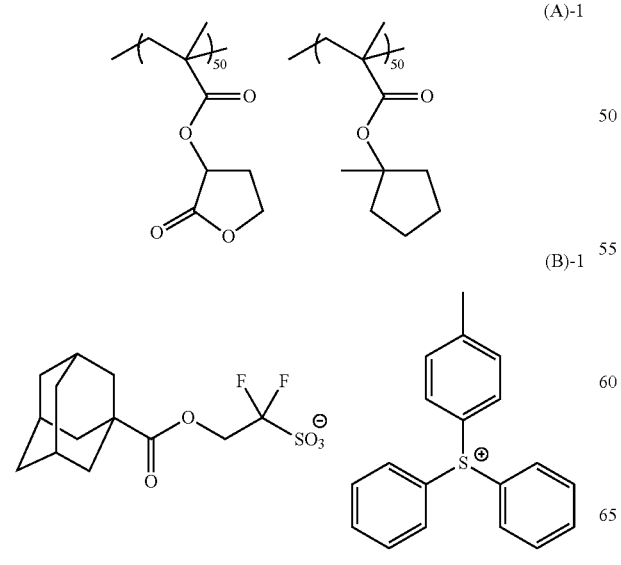

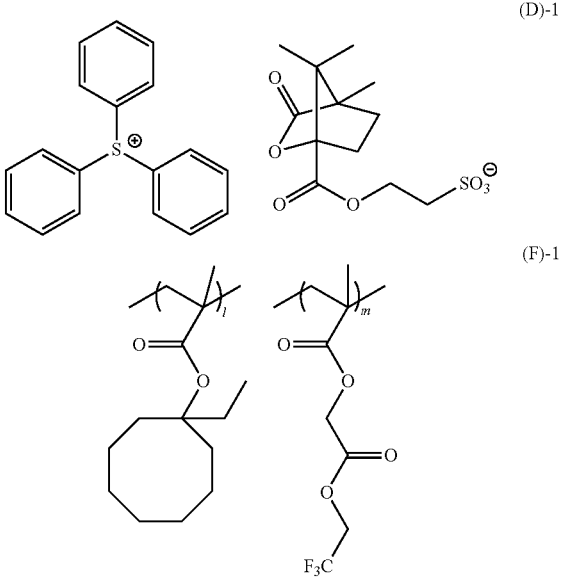

<Formation of First Resist Pattern: Alkali-Developed Positive-Type Pattern>

An organic anti-reflection film composition "ARC29A" (trade name, manufactured by Brewer Science Inc.) was applied onto a 12-inch silicon wafer by a spinner, and baked on a hot plate at 205° C. for 60 seconds to be dried, thereby forming an organic anti-reflection film with a film thickness of 85 nm.

Subsequently, the above resist composition was applied onto the organic anti-reflection film by a spinner, and prebaked (PAB) on a hot plate at 90° C. for 60 seconds to be dried, thereby forming a resist film with a film thickness of 60 nm.

Subsequently, the resist film was selectively irradiated with an ArF excimer laser (193 nm) through a mask pattern (binary mask), using an exposure apparatus NSR-S609B (manufactured by Nikon Corporation: NA (numerical aperture)=1.07; Dipole 0.97/0.78 with polano).

Subsequently, alkali development was carried out at 23° C. for 30 seconds, using 2.38% by weight of an aqueous tetramethylammonium hydroxide (TMAH) solution "NMD-3" (trade name, manufactured by Tokyo Ohka Kogyo Co., Ltd.).

Then, heat treatment after exposure was carried out at 100° C. (PEB(° C.)) for 60 seconds.

As a result, a line & space pattern (hereinafter, referred to as "LS pattern") having a space width of 40 nm and a line width of 120 nm was formed.

Step B

<Preparation of Acid Component-Containing Solution>

As shown in Table below, an acid component, a polymer, and a solvent were mixed to prepare an acid component-containing solution (hereinafter, referred to as a "first solution").

<Formation of First Layer>

The first solution was applied onto the first resist pattern obtained in the [step A] by a spinner to form a first layer. The coating thickness of the acid component-containing solution is given in Table below.

Step B1

<Preparation of Solvent-Containing Solution>
As shown in Table below, an acid component, a polymer, and a solvent were mixed to prepare a solvent-containing solution (hereinafter, referred to as a "second solution").
<Application of Solvent-Containing Solution>
The second solution was applied by a spinner to cover the first layer obtained in the [step B].

Step C

A structure including the first resist pattern obtained in the steps A to C was baked at each temperature given in Table below for 60 seconds.

Step D

After the [step C], development treatment was carried out for 13 seconds using butyl acetate, thereby forming a split pattern.

Comparative Examples 1-1 to 1-6

[Step A] and [step B] were carried out in the same manner as in Examples 1-1 to 1-30 to form each first layer. Then, a structure containing the first resist pattern was baked at each temperature given in Table below for 60 seconds, and was developed using butyl acetate for 13 seconds.

TABLE 1

|  | First solution | | | First layer | Second solution | | | Baking |
|---|---|---|---|---|---|---|---|---|
|  | Acid component | Polymer | Solvent | thickness [nm] | Quencher | Polymer | Solvent | temperature (° C.) |
| Example 1-1 | (T0)-1 [0.4] | P1 [1.6] | S1 [98.0] | 50 | (D2)-1 [0.3] | P3 [0.9] | S3 [98.8] | 110 |
| Example 1-2 | (T0)-2 [0.5] | P1 [1.6] | S1 [97.9] | 50 | (D2)-1 [0.3] | P3 [0.9] | S3 [98.8] | 110 |
| Example 1-3 | (T1)-1 [0.5] | P1 [1.6] | S1 [97.9] | 50 | (D2)-1 [0.3] | P3 [0.9] | S3 [98.8] | 110 |
| Example 1-4 | (T1)-2 [0.7] | P1 [1.6] | S1 [97.7] | 50 | (D2)-1 [0.3] | P3 [0.9] | S3 [98.8] | 110 |
| Example 1-5 | (T1)-3 [0.6] | P1 [1.6] | S1 [97.8] | 50 | (D2)-1 [0.3] | P3 [0.9] | S3 [98.8] | 110 |
| Example 1-6 | (T1)-4 [0.4] | P1 [1.6] | S1 [98.0] | 50 | (D2)-1 [0.3] | P3 [0.9] | S3 [98.8] | 110 |
| Example 1-7 | (T0)-1 [0.6] | P2 [2.2] | S1 [97.2] | 50 | (D2)-1 [0.3] | P3 [0.9] | S3 [98.8] | 110 |
| Example 1-8 | (T1)-2 [1.0] | P2 [2.2] | S1 [96.8] | 50 | (D2)-1 [0.3] | P3 [0.9] | S3 [98.8] | 110 |
| Example 1-9 | (T0)-1 [0.4] | P1 [1.6] | S2 [98.0] | 50 | (D2)-1 [0.3] | P3 [0.9] | S3 [98.8] | 110 |
| Example 1-10 | (T1)-2 [0.7] | P1 [1.6] | S2 [97.7] | 50 | (D2)-1 [0.3] | P3 [0.9] | S3 [98.8] | 110 |

TABLE 2

|  | First solution | | | First layer | Second solution | | | Baking |
|---|---|---|---|---|---|---|---|---|
|  | Acid component | Polymer | Solvent | thickness [nm] | Quencher | Polymer | Solvent | temperature (° C.) |
| Example 1-11 | (T1)-2 [0.7] | P1 [1.6] | S1 [97.7] | 50 | (D2)-2 [0.1] | P3 [0.9] | S3 (99.0) | 110 |
| Example 1-12 | (T1)-2 [0.7] | P1 [1.6] | S1 [97.7] | 50 | (Cd)-1 [0.3] | P3 [0.9] | S3 [98.8] | 110 |
| Example 1-13 | (T1)-2 [0.7] | P1 [1.6] | S1 [97.7] | 50 | (D2)-1 [0.3] | P4 [0.9] | S3 [98.8] | 110 |
| Example 1-14 | (T1)-2 [0.7] | P1 [1.6] | S1 [97.7] | 50 | (D2)-1 [0.3] | P3 [0.9] | S4 [98.8] | 110 |
| Example 1-15 | (T1)-2 [0.7] | P1 [1.6] | S1 [97.7] | 50 | (D2)-1 [0.3] | P4 [0.9] | S4 [98.8] | 110 |
| Example 1-16 | (T1)-2 [0.7] | P1 [1.6] | S1 [97.7] | 50 | (D2)-1 [0.3] | — | S3 [99.7] | 110 |
| Example 1-17 | (T1)-2 [0.7] | P1 [1.6] | S1 [97.7] | 50 | (D2)-1 [0.3] | — | S4 [99.7] | 110 |
| Example 1-18 | (T1)-2 [0.7] | P1 [1.6] | S1 [97.7] | 50 | — | — | S3 [100] | 110 |
| Example 1-19 | (T1)-2 [0.7] | P1 [1.6] | S1 [97.7] | 50 | — | — | S4 [100] | 110 |

TABLE 3

| | First solution | | | First layer thickness [nm] | Second solution | | | Baking temperature (° C.) |
|---|---|---|---|---|---|---|---|---|
| | Acid component | Polymer | Solvent | | Quencher | Polymer | Solvent | |
| Example 1-20 | (T1)-2 [1.1] | P1 [2.6] | S1 [96.3] | 100 | (D2)-1 [0.3] | P3 [0.9] | S3 [98.8] | 110 |
| Example 1-21 | (T1)-2 [0.2] | P1 [0.5] | S1 [99.3] | 20 | (D2)-1 [0.3] | P3 [0.9] | S3 [98.8] | 110 |
| Example 1-22 | (T1)-2 [0.7] | P1 [1.6] | S1 [97.7] | 50 | (D2)-1 [0.3] | P3 [0.9] | S3 [98.8] | 100 |
| Example 1-23 | (T1)-2 [0.7] | P1 [1.6] | S1 [97.7] | 50 | (D2)-1 [0.3] | P3 [0.9] | S3 [98.8] | 90 |
| Example 1-24 | (T1)-2 [0.9] | P3 [2.2] | S3 [96.9] | 50 | (D2)-1 [0.3] | P1 [0.9] | S1 [98.8] | 110 |
| Example 1-25 | (T1)-2 [0.7] | P1 [1.6] | S1 [97.7] | 50 | (D2)-1 [0.3] | P1 [0.9] | S1 [98.8] | 110 |
| Example 1-26 | (T1)-2 [0.3] | P3 [0.7] | S3 [99.0] | 20 | (D2)-1 [0.3] | P3 [0.9] | S3 [98.8] | 110 |
| Example 1-27 | (T1)-2 [0.2] | P1 [0.5] | S1 [99.3] | 20 | — | — | S3 [100] | 110 |
| Example 1-28 | (T1)-2 [0.7] | P1 [1.6] | S1 [97.7] | 50 | — | — | S4 [100] | 110 |
| Example 1-29 | (T0)-1 [0.6] | P5 [1.4] | water [98.0] | 50 | (D2)-1 [0.3] | P3 [0.9] | S3 [98.8] | 110 |
| Example 1-30 | (T1)-2 [0.6] | P1 [1.4] | S1 [98.0] | 50 | (D2)-1 [0.3] | P5 [0.9] | water [98.8] | 110 |

TABLE 4

| | First Solution | | | First layer thickness [nm] | Baking temperature (° C.) |
|---|---|---|---|---|---|
| | Acid component | Polymer | Solvent | | |
| Comparative Example 1-1 | (T1)-2 [0.7] | P1 [1.6] | S1 [97.7] | 50 | 110 |
| Comparative Example 1-2 | (T1)-2 [0.7] | P1 [1.6] | S1 [97.7] | 50 | 100 |
| Comparative Example 1-3 | (T1)-2 [0.7] | P1 [1.6] | S1 [97.7] | 50 | 90 |
| Comparative Example 1-4 | (T1)-2 [0.2] | P1 [0.5] | S1 [99.3] | 20 | 110 |
| Comparative Example 1-5 | (T1)-2 [0.2] | P1 [0.5] | S1 [99.3] | 20 | 100 |
| Comparative Example 1-6 | (T1)-2 [0.2] | P1 [0.5] | S1 [99.3] | 20 | 90 |

In Tables above, abbreviations have the following meanings or are compounds represented by formulae shown below. Further, the numerical value in parenthesis indicates a blended amount (parts by weight)

(S4): mixed solvent of (S3)/PGMEA=95/5 (weight ratio)

[Chemical Formula 64]

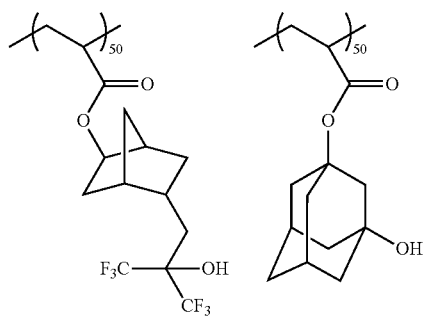
(P1)

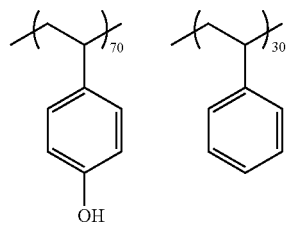
(P2)

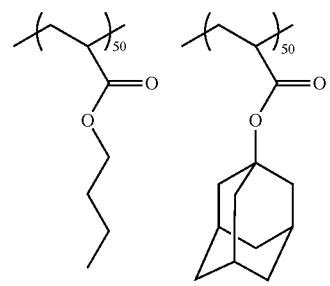
(P3)

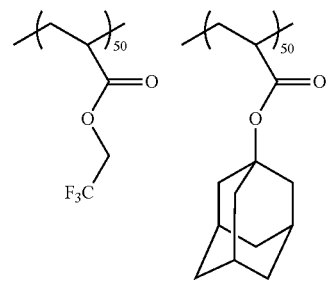
(P4)

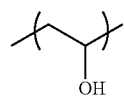
(P5)

-continued

[Chemical Formula 65]

(T0)-1

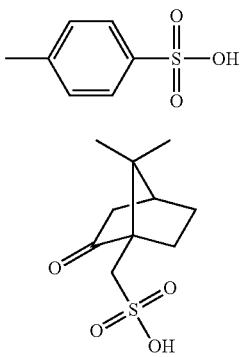

(T0)-2

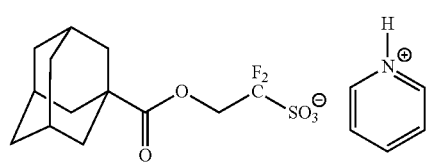

(T1)-1

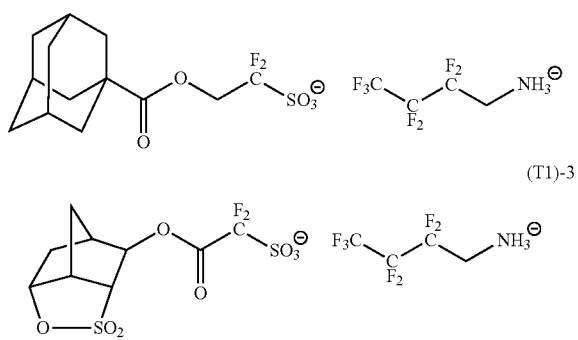

(T1)-2

(T1)-3

(T1)-4

[Chemical Formula 66]

(D2)-1

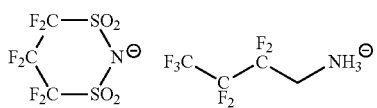

(D2)-2

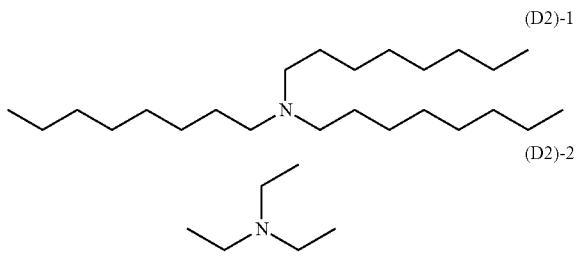

(Cd)-1

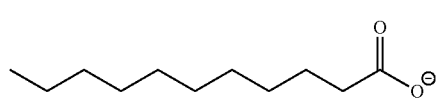

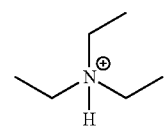

-continued

[Chemical Formula 67]

(S1)

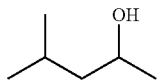

(S2)

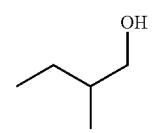

(S3)

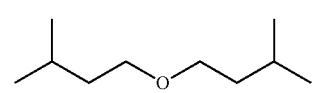

<Evaluation of Split Pattern>

The pattern separation and CD of the formed split pattern were evaluated.

[Pattern Separation]

The split pattern was observed with a length measuring scanning electron microscope (SEM) (trade name: S-9380, manufactured by Hitachi High-Technologies Corporation; acceleration voltage: 300 V), and the evaluation of pattern separation was carried out according to the following five-point scale. The results thereof are summarized in Table below.

[Pattern Separation Evaluation Criteria]

1: Patterns cannot be observed because they are almost dissolved.

2: Split patterns are obtained, but some of the patterns are collapsed.

3: Split patterns are obtained, and there is no collapse and no connection between the patterns.

4: Split patterns are obtained, but some of the patterns are connected.

5: Split pattern cannot be formed because first resist pattern is maintained.

[Evaluation of Pattern Dimension]

100 points in the pattern were observed from the upper side thereof using a length measuring scanning electron microscope (SEM) (product name: S-9380, manufactured by Hitachi High-Technologies Corporation; acceleration voltage: 300 V) to measure each line width (nm). The results thereof are summarized as "CD (nm)" in Table below.

TABLE 5

| | Split pattern | |
| --- | --- | --- |
| | Pattern separation | CD(nm) |
| Example 1-1 | 3 | 30 |
| Example 1-2 | 3 | 27 |
| Example 1-3 | 3 | 29 |
| Example 1-4 | 3 | 25 |
| Example 1-5 | 3 | 25 |
| Example 1-6 | 3 | 28 |
| Example 1-7 | 3 | 30 |
| Example 1-8 | 3 | 25 |
| Example 1-9 | 3 | 31 |
| Example 1-10 | 3 | 25 |

TABLE 6

| | Split pattern | |
| | Pattern separation | CD(nm) |
|---|---|---|
| Example 1-11 | 3 | 27 |
| Example 1-12 | 3 | 26 |
| Example 1-13 | 3 | 25 |
| Example 1-14 | 3 | 28 |
| Example 1-15 | 3 | 24 |
| Example 1-16 | 3 | 26 |
| Example 1-17 | 3 | 26 |
| Example 1-18 | 4 | 41 |
| Example 1-19 | 4 | 37 |

TABLE 7

| | Split pattern | |
| | Pattern separation | CD(nm) |
|---|---|---|
| Example 1-20 | 4 | 38 |
| Example 1-21 | 3 | 21 |
| Example 1-22 | 2 | 24 |
| Example 1-23 | 2 | 23 |
| Example 1-24 | 3 | 25 |
| Example 1-25 | 2 | 33 |
| Example 1-26 | 2 | 35 |
| Example 1-27 | 4 | 38 |
| Example 1-28 | 3 | 32 |
| Example 1-29 | 3 | 31 |
| Example 1-30 | 3 | 26 |

TABLE 8

| | Split pattern | |
| | Pattern separation | CD(nm) |
|---|---|---|
| Comparative Example 1-1 | 5 | — |
| Comparative Example 1-2 | 5 | — |
| Comparative Example 1-3 | 1 | — |
| Comparative Example 1-4 | 5 | — |
| Comparative Example 1-5 | 5 | — |
| Comparative Example 1-6 | 1 | — |

From the results shown in Tables above, in Examples 1-1 to 1-30, in each of which the second solution was applied to cover the first layer, a split pattern was formed, and the pattern dimension thereof was satisfactory. In contrast, in Comparative Examples 1-1 to 1-6, in each of which the second solution was not applied, a split pattern was not formed because a pattern was not separated, or the first resist pattern was dissolved.

Examples 1-31 to 1-39

Preparation of Resist Composition

The polymeric compounds 1-1 to 1-9 having the structures shown in Table 9 were synthesized by a conventional method, with using monomers (1) to (9) corresponding to the structural units constituting the respective polymeric compounds in the molar ratio shown in Table 9.

TABLE 9

| | | Polymeric compounds | | | | | | | | |
| | | 1-1 | 1-2 | 1-3 | 1-4 | 1-5 | 1-6 | 1-7 | 1-8 | 1-9 |
|---|---|---|---|---|---|---|---|---|---|---|
| monomer | (1) | 5 | 5 | | | | | | | |
| | (2) | 5 | | | | | | | | |
| | (3) | | 5 | 5 | 5 | 5 | 5 | 5 | 4 | 3 |
| | (4) | | | | 5 | | | | | |
| | (5) | | | | | 5 | | | | |
| | (6) | | | | | | 5 | | | |
| | (7) | | | | | | | 5 | 4 | 4 |
| | (8) | | | | | | | | 1 | 2 |
| | (9) | | | | | | | 1 | 1 | 1 |
| Mw | | 7000 | 7000 | 7000 | 7000 | 7000 | 7000 | 7000 | 7000 | 7000 |
| Mw/Mn | | 1.6 | 1.6 | 1.6 | 1.6 | 1.6 | 1.6 | 1.6 | 1.6 | 1.6 |

[Chemical Formula 68]

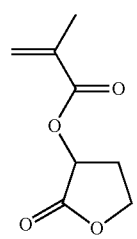

(1)

-continued
(2)
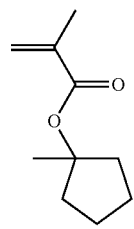
(3)
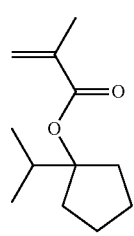
(4)
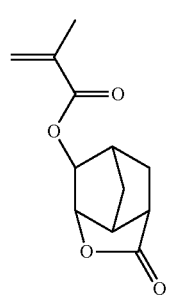
(5)
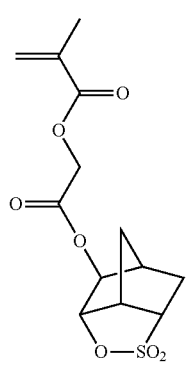
-continued
(6)
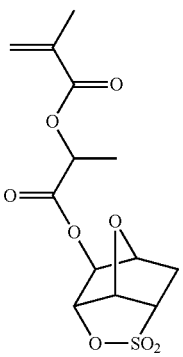
(7)
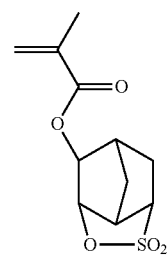
(8)
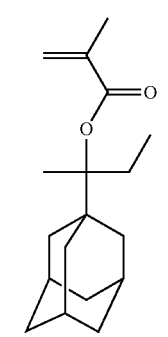
(9)
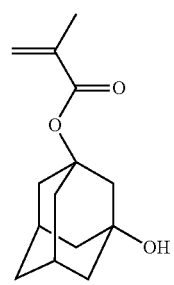
The components shown in Table 10 were mixed together and dissolved to obtain resist compositions 1-2 to 1-10.
TABLE 10
|  | Component (A) | Component (B) | Component (D) | Component (F) | Component (S) | Rmax (nm/s) | Rmin (nm/s) |
|---|---|---|---|---|---|---|---|
| Resist Composition 1-2 | (A)-2 [100] | (B)-1 [10] | (D)-1 [7] | (F)-1 [2] | (S)-1 [4000] | 14 | 0.1 |
| Resist Composition 1-3 | (A)-3 [100] | (B)-1 [10] | (D)-1 [7] | (F)-1 [2] | (S)-1 [4000] | 22 | 0.1 |
| Resist Composition 1-4 | (A)-4 [100] | (B)-1 [10] | (D)-1 [7] | (F)-1 [2] | (S)-1 [4000] | 53 | 0.1 |
| Resist | (A)-5 | (B)-1 | (D)-1 | (F)-1 | (S)-1 | 6 | 0.0 |

TABLE 10-continued

| | Component (A) | Component (B) | Component (D) | Component (F) | Component (S) | Rmax (nm/s) | Rmin (nm/s) |
|---|---|---|---|---|---|---|---|
| Composition 1-5 | [100] | [10] | [7] | [2] | [4000] | | |
| Resist Composition 1-6 | (A)-6 [100] | (B)-1 [10] | (D)-1 [7] | (F)-1 [2] | (S)-1 [4000] | 40 | 0.4 |
| Resist Composition 1-7 | (A)-7 [100] | (B)-1 [10] | (D)-1 [7] | (F)-1 [2] | (S)-1 [4000] | 14 | 0.0 |
| Resist Composition 1-8 | (A)-8 [100] | (B)-1 [10] | (D)-1 [7] | (F)-1 [2] | (S)-1 [4000] | 17 | 0.4 |
| Resist Composition 1-9 | (A)-9 [100] | (B)-1 [10] | (D)-1 [7] | (F)-1 [2] | (S)-1 [4000] | 28 | 0.5 |
| Resist Composition 1-10 | (A)-10 [100] | (B)-1 [10] | (D)-1 [7] | (F)-1 [2] | (S)-1 [4000] | 46 | 1.5 |

In Table 10, the reference characters indicate the following. Further, the values in brackets [ ] indicate the amount (in terms of parts by weight) of the component added.

(A)-2 to (A)-10: aforementioned polymeric compounds 1-1 to 1-9

(B)-1: aforementioned compound (B)-1

(D)-1: aforementioned compound (D)-1

(F)-1: aforementioned polymeric compound (F)-1

(S)-1: a mixed solvent of PGMEA/PGME/cyclohexanone (45/30/25 by weight ratio)

With respect to the resist compositions 1-2 to 1-10, the maximum value ($R_{max}$, unit: nm/s) of the dissolution rate (an amount of thickness loss per immersing time) in butyl acetate and the minimum value ($R_{min}$, unit: nm/s) thereof were determined in the method described below, and the results are shown in Table 10.

[Evaluation of Dissolution Rate]

Each of the resist compositions 1-2 to 1-10 was uniformly applied to an 8-inch silicon substrate using a spinner, and the composition was then subjected to a prebake (PAB) treatment on a hot plate at 110° C. for 60 seconds, thereby forming a resist film having a film thickness of 160 nm.

The resist film was immersed in butyl acetate at 23° C. for 10 seconds, and then the maximum value ($R_{max}$, unit: nm/s) of the dissolution rate (an amount of thickness loss per immersing time) and the minimum value ($R_{min}$, unit: nm/s) thereof were determined using RDA-808RB (product name; manufactured by Litho Tech Japan Corporation).

Step A

<Formation of First Resist Pattern: Alkali-Developed Positive-Type Pattern>

An organic anti-reflection film composition "ARC29A" (product name, manufactured by Brewer Science Inc.) was applied onto a 12-inch silicon wafer by a spinner, and baked on a hot plate at 205° C. for 60 seconds to be dried, thereby forming an organic anti-reflection film with a film thickness of 85 nm.

Subsequently, each of the above resist compositions 1-2 to 1-10 was applied onto the organic anti-reflection film by a spinner, and prebaked (PAB) on a hot plate at 90° C. for 60 seconds to be dried, thereby forming a resist film with a film thickness of 60 nm.

Subsequently, the resist film was selectively irradiated with an ArF excimer laser (193 nm) through a mask pattern (binary mask), using an exposure apparatus NSR-S609B (manufactured by Nikon Corporation: NA (numerical aperture)=1.07; Dipole 0.97/0.78 with polano).

Subsequently, alkali development was carried out at 23° C. for 10 seconds, using 2.38% by weight of an aqueous tetramethylammonium hydroxide (TMAH) solution "NMD-3" (trade name, manufactured by Tokyo Ohka Kogyo Co., Ltd.).

Then, heat treatment after exposure was carried out at 90° C. (PEB(° C.)) for 60 seconds.

As a result, a line and space pattern (hereinafter, referred to as "LS pattern") having a pitch width of 160 nm and a line width of 120 nm was formed.

Step B

<Preparation of Acid Component-Containing Solution>

The same acid component, the same polymer and the same solvent as the above Example 1-21 were mixed to prepare an acid component-containing solution (hereinafter, referred to as a "first solution").

<Formation of First Layer>

The first solution was applied onto the first resist pattern obtained in the [step A] by a spinner (1500 rpm) to form a first layer. The coating thickness of the acid component-containing solution was 20 nm Step B1

<Preparation of Solvent-Containing Solution>

The same acid component, the same polymer and the same solvent as the above Example 1-21 were mixed to prepare a solvent-containing solution (hereinafter, referred to as a "second solution").

<Application of Solvent-Containing Solution>

The second solution was applied by a spinner to cover the first layer obtained in the [step B].

Step C

A structure including the first resist pattern obtained in the steps A to C was subjected to a bake treatment at 110° C. for 60 seconds.

Step D

After the [step C], a development treatment was carried out for 13 seconds using butyl acetate, thereby forming a split pattern. Thereafter, heat treatment after exposure was carried out at 100° C. for 45 seconds.
<Evaluation of Split Pattern>
The pattern separation of the formed split pattern was evaluated.
[Pattern Separation]
The split pattern was observed with a length measuring scanning electron microscope (SEM) (trade name: S-9380, manufactured by Hitachi High-Technologies Corporation; acceleration voltage: 300 V), and the evaluation of pattern separation was carried out according to the following five-point scale. The results thereof are summarized in Table below.
[Pattern Separation Evaluation Criteria]
1: Patterns cannot be observed because they are almost dissolved.
2: Split patterns are obtained, but some of the patterns are collapsed.
3: Split patterns are obtained, and there is no collapse and no connection between the patterns.
4: Split patterns are obtained, but some of the patterns are connected.
5: Split pattern cannot be formed because first resist pattern is maintained.

TABLE 11

|  | Resist composition | Pattern separation |
| --- | --- | --- |
| Ex. 1-31 | Resist composition 1-2 | 3 |
| Ex. 1-32 | Resist composition 1-3 | 3 |
| Ex. 1-33 | Resist composition 1-4 | 3 |
| Ex. 1-34 | Resist composition 1-5 | 4 |
| Ex. 1-35 | Resist composition 1-6 | 2 |
| Ex. 1-36 | Resist composition 1-7 | 3 |
| Ex. 1-37 | Resist composition 1-8 | 2 |
| Ex. 1-38 | Resist composition 1-9 | 2 |
| Ex. 1-39 | Resist composition 1-10 | 2 |

As shown in Table 11, when the resist composition forming the first resist pattern had the dissolution rate maximum value of 5 nm/is or more and the minimum value of 1 nm/s or less, the pattern separated satisfactorily.

Examples 2-1 to 2-8, Comparative Example 2-1

Step A

<Production of Resist Composition>
100 parts by weight of a polymeric compound (A)-1' shown below (Mw: 7000), 10 parts by weight of a compound (B)-1' shown below, 7 parts by weight of a compound (D)-1' shown below, 2 parts by weight of a compound (F)-1' shown below (l/m=77/23 (molar ratio), Mw: 23100, Mw/Mn: 1.78), 2 parts by weight of salicylic acid, and 4000 parts by weight of a solvent (a mixed solvent of PGMEA/ PGME/cyclohexanone=45/30/25 (weight ratio)) were mixed together to obtain a resist composition.

[Chemical Formula 69]

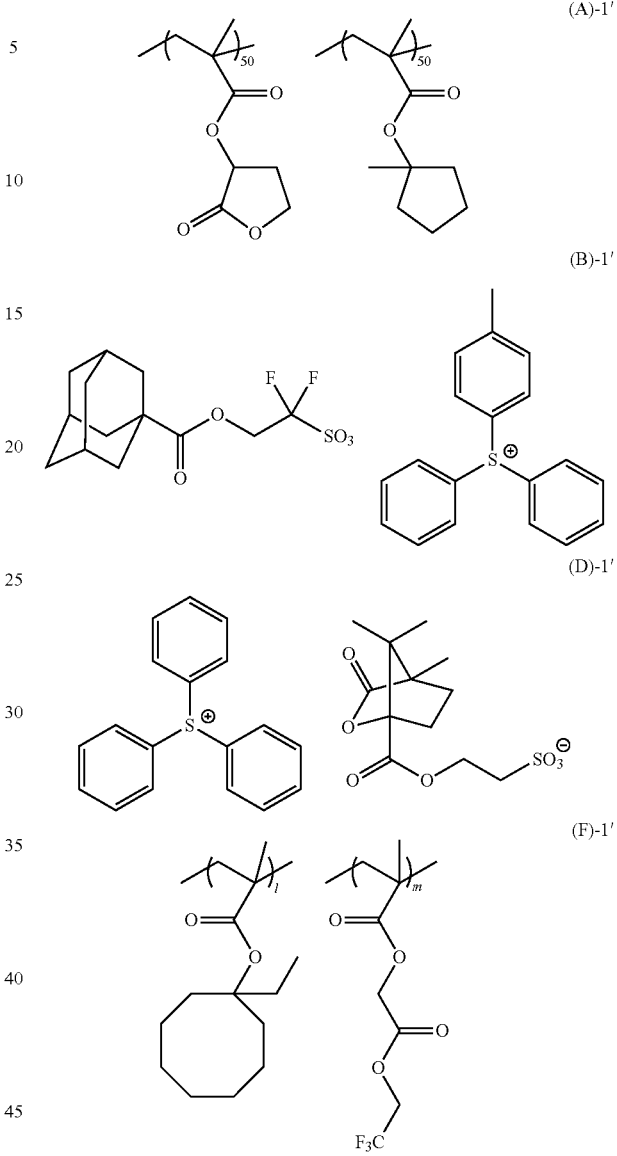

<Formation of Positive Resist Pattern by Alkali Development>
An organic anti-reflection film composition (product name: ARC29A, manufactured by Brewer Science Ltd.) was applied to an 12-inch silicon wafer using a spinner, and the composition was then baked at 205° C. for 60 seconds, thereby forming an organic anti-reflection film having a film thickness of 95 nm.
Then, the resist composition obtained above was applied to the undercoat agent using a spinner, and was then prebaked (PAB) on a hotplate at 90° C. for 60 seconds and dried, thereby forming a resist film having a film thickness of 90 nm.
Subsequently, the resist film was selectively irradiated with an ArF excimer laser (193 nm) through a mask pattern (a binary mask), using an exposure apparatus NSR-S610S (manufactured by Nikon Corporation, NA (numerical aperture)=1.30, Dipole with POLANO).
Thereafter, alkali developing was conducted for 10 seconds at 23° C. in a 2.38% by weight aqueous solution of tetramethylammonium hydroxide (TMAH) (product name: NMD-3; manufactured by Tokyo Ohka Kogyo Co., Ltd.).

Further, a post exposure bake treatment was conducted at 80° C. (PEB(° C.)) for 60 seconds.

As a result, a line and space pattern (hereafter, referred to as "LS pattern") as shown below was formed.

LS pattern 1: 120 nm pitch/83 nm line, mask size: 60 nm
LS pattern 2: 160 nm pitch/105 nm line, mask size: 80 nm Step B <Production of Solution Containing Acid Component>

100 parts by weight of a polymeric compound (AP)-1' shown below (Mw: 9000), 40 parts by weight of a compound (T)-1' shown below, and 17000 parts by weight of a solvent (4-methyl-2-pentanol) were mixed together to obtain a solution containing an acid component.

[Chemical Formula 70]

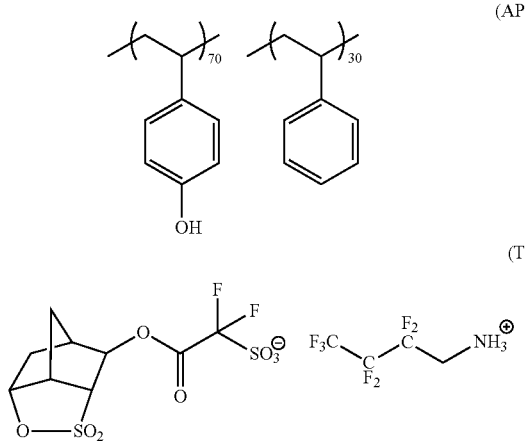

<Formation of First Layer>

The solution containing an acid component obtained above was applied to the first resist pattern formed in the [step A] using a spinner (1500 rpm), thereby forming a first layer.

Step B1

<Production of Solution Containing Basic Component>

100 parts by weight of a polymeric compound (BP)-1' shown below (Mw: 15000), 20 parts by weight of trioctylamine and 10000 parts by weight of a solvent (isoamyl ether) were mixed together to obtain a solution containing a basic component.

[Chemical Formula 71]

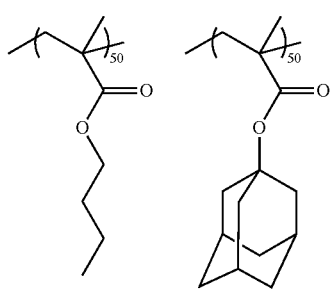

The solution containing a basic component obtained above was applied onto the first layer formed in the [step B] using a spinner (1500 rpm).

Step C

A structure including the first resist pattern obtained in the steps A to B was subjected to a bake treatment at 110° C. for 60 seconds.

Step D

Then, a development treatment was conducted using butyl acetate for 13 seconds, thereby forming a second resist pattern.

Step E

<Production of Pattern Reversing Composition>
<Synthesis of Polymeric Compound 2-1>

In a separable flask equipped with a thermometer, a reflux tube and a nitrogen feeding pipe, 20.00 g (123.3 mmol) of Pre-M1 and 5.50 g (52.8 mmol) of M2 were dissolved in 38.25 g of methyl ethyl ketone (MEK) to obtain a solution.

Then, 2.027 g (8.81 mmol) of dimethyl azobisisobutyrate as a radical polymerization initiator was added to and dissolved to obtain a dripping solution.

21.25 g of MEK was heated to 80° C. and refluxed, and then the dripping solution was dropwise added to MEK in a nitrogen atmosphere over 4 hours. The resulting reaction solution was heated while stirring for 1 hour, and then cooled to room temperature.

The obtained reaction polymer solution was dropwise added to 340 g of heptane, and an operation to deposit a polymer was conducted. Thereafter, the precipitated white powder was separated by filtration, followed by washing with methanol and drying, thereby obtaining 17.88 g of Pre-P1.

Thereafter, 41.72 g of methanol was added to Pre-P1, further adding 2.12 g (17.3 mmol) of N,N-dimethyl-4-aminopyridine. This reaction system was heated to 70° C. with refluxing methanol, and reaction was conducted in a nitrogen atmosphere over 12 hours. The obtained solution was dropwise added to 238.4 g of heptane, followed by drying, thereby obtaining 12.80 g of a polymeric compound 1. The reaction formula is shown below.

Polymeric compounds 2-2 to 2-4 were synthesized in the same manner.

The weight average molecular weight (Mw) and the molecular weight dispersity (Mw/Mn) of these polymeric compounds determined by the polystyrene equivalent value as measured by gel permeation chromatography (GPC) and the compositional ratios of these polymeric compounds as measured by carbon 13 nuclear magnetic resonance spectroscopy (600 MHz, $^{13}$C-NMR) are shown in Table 12.

[Chemical Formula 72]

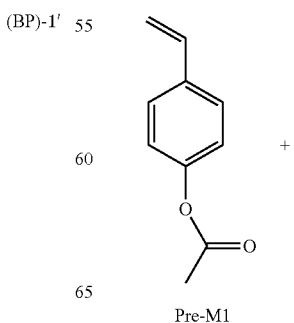

Pre-M1

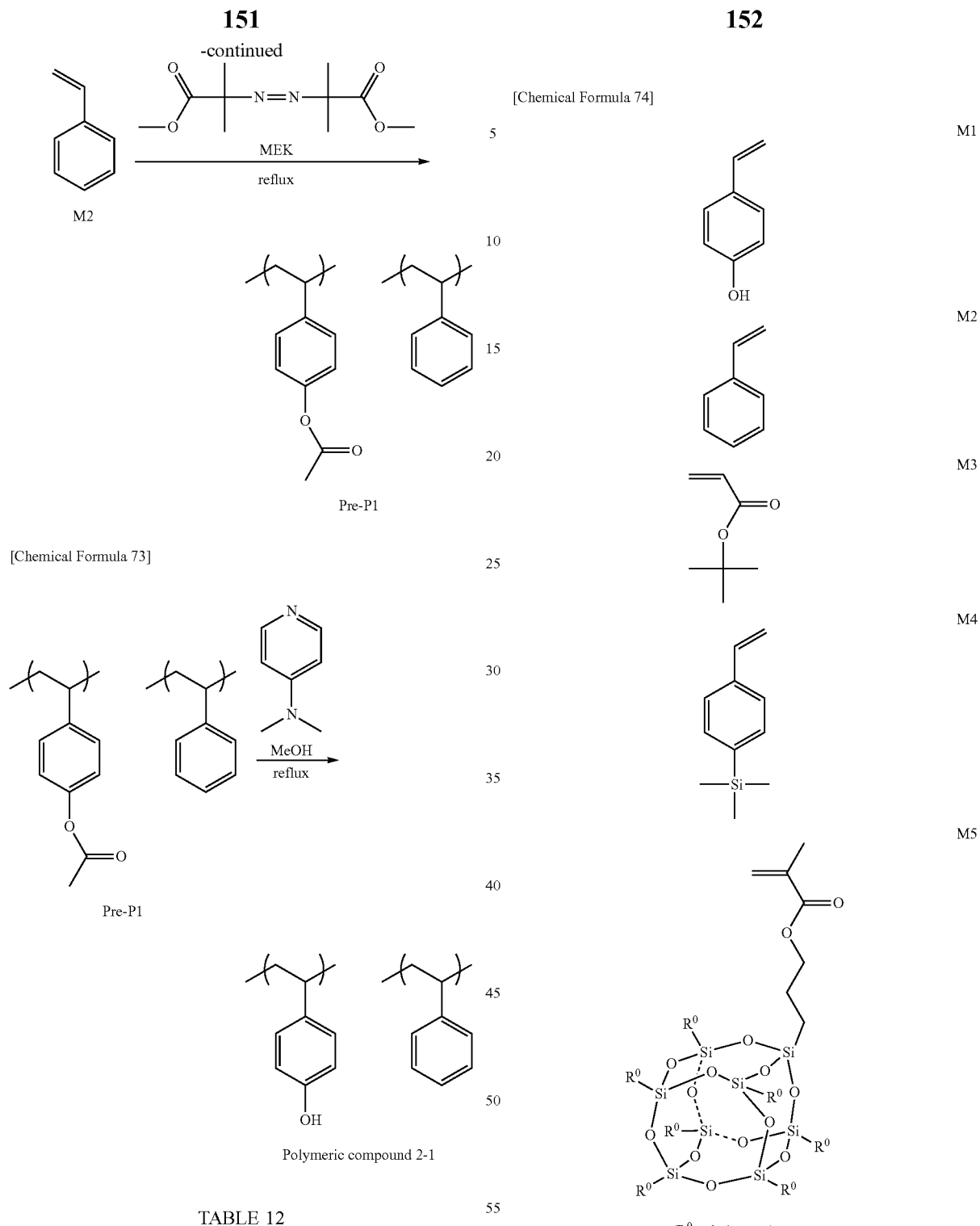

| | | Mw | Mw/Mn |
|---|---|---|---|
| Polymeric Compound 2-1 | M1/M2 [68/32] | 9200 | 1.7 |
| Polymeric Compound 2-2 | M1/M3 [73/27] | 10700 | 1.6 |
| Polymeric Compound 2-3 | M1/M4 [80/20] | 9600 | 1.6 |
| Polymeric Compound 2-4 | M1/M5 [94/6] | 10200 | 1.8 |

In Table 12, M1 to M5 represent a monomer shown blow.

Each of the polymeric compounds 2-1 to 2-4 was dissolved in butyl acetate (resin concentration: 1.2% by weight), thereby producing pattern reversing compositions 2-1 to 2-4.

<Formation of Reversing Pattern>

Each of the pattern reversing compositions 2-1 to 2-4 was applied onto the second resist pattern formed in the [step D], thereby forming a pattern reversing film.

Among the second resist patterns, the examples applied the pattern reversing compositions 2-1 to 2-4 to the LS pattern 1 are mentioned as Examples 2-1 to 2-4, respectively.

On the other hand, among the second resist patterns, the examples applied the pattern reversing compositions 2-1 to 2-4 to the LS pattern 2 are mentioned as Examples 2-5 to 2-8, respectively.

Thereafter, after heating at 90° C. for 60 seconds, alkali developing was conducted for 30 seconds at 23° C. in a 2.38% by weight aqueous solution of tetramethylammonium hydroxide (TMAH) (product name: NMD-3; manufactured by Tokyo Ohka Kogyo Co., Ltd.).

As a result of the development, a third pattern was formed. With respect to the third pattern, pattern length was measured using a length measuring SEM (CG-5000, manufactured by Hitachi Corporation), and the size was determined.

The results thereof are shown in Tables 13 to 14.

TABLE 13

|  |  | Size (nm) | | |
| --- | --- | --- | --- | --- |
|  |  | Line | Space | Pitch |
|  | First resist pattern | 83 | 37 | 120 |
|  | Second resist pattern | 23 | 37 | 60 |
| Ex. 2-1 | Pattern reversing composition 2-1 | 37 | 23 | 60 |
| Ex. 2-2 | Pattern reversing composition 2-2 | 37 | 23 | 60 |
| Ex. 2-3 | Pattern reversing composition 2-3 | 37 | 23 | 60 |
| Ex. 2-4 | Pattern reversing composition 2-4 | 37 | 23 | 60 |

TABLE 14

|  |  | Size (nm) | | |
| --- | --- | --- | --- | --- |
|  |  | Line | Space | Pitch |
|  | First resist pattern | 105 | 55 | 160 |
|  | Second resist pattern | 25 | 55 | 80 |
| Ex. 2-5 | Pattern reversing composition 2-1 | 55 | 25 | 80 |
| Ex. 2-6 | Pattern reversing composition 2-2 | 55 | 25 | 80 |
| Ex. 2-7 | Pattern reversing composition 2-3 | 55 | 25 | 80 |
| Ex. 2-8 | Pattern reversing composition 2-4 | 55 | 25 | 80 |
| Comp. Ex. 2-1 | First resist pattern | 44 | 36 | 80 |

In the Comparative Example 2-1, the "first resist pattern" shows a minimum space size formed in the first resist pattern formation.

The critical resolution in ArF immersing lithography is about 80 nm space in LS pattern. On the other hand, the present invention enabled to form a pattern in fine pitch size, such as 60 nm pitch.

Further, even in 80 nm pitch, a space was able to be formed at a size that was ordinarily impossible to resolve using ArF exposure.

<Evaluation of Dry Etching>

With respect to the resist composition and the pattern reversing compositions 2-1 to 2-4 shown above, dry etching was evaluated.

Each of the resist composition and the pattern reversing compositions 2-1 to 2-4 was applied to silicon substrate and the composition was baked at 90° C. for 60 seconds, thereby forming a resin film.

The obtained resin film was conducted etching under the following conditions.

Apparatus: TCA-3822
Output power: 400 W
Chamber pressure: 40 Pa
Stage temperature: 40° C.
Gaseous species: $CF_4$
Gas flow rate: 20 mL/min
Period of etching: 30 seconds From the difference between before and after etching, the amount of thickness loss per 1 second was calculated as an etching rate (mn/s). The results are shown in Table 15.

TABLE 15

|  | etching rate(nm/s) |
| --- | --- |
| pattern reversing composition 2-1 | 0.8 |
| pattern reversing composition 2-2 | 1.1 |
| pattern reversing composition 2-3 | 0.6 |
| pattern reversing composition 2-4 | 0.5 |
| resist composition | 1.8 |

The smaller this etching rate is, the more resistant is the pattern to etching, thereby indicating that the substrate is easy to fabricate. As seen from the results, the pattern reversing compositions exhibited improved etching resistance, as compared to the resist compositions. Further, the pattern reversing compositions containing Si unit exhibited more improved etching resistance.

Examples 3-1 to 3-6

Production of Positive Resist Composition

Each positive resist compositions 3-1 to 3-6 (in the table shown below, referred to as "resist composition 3-1 to 3-6") shown in Table 16 was produced.

TABLE 16

|  | Component (A) | Component (B) | Component (D) | Component (F) | Component (E) | Component (S) | |
| --- | --- | --- | --- | --- | --- | --- | --- |
| Resist Composition 3-1 | (A)-1" [100] | (B)-1" [10] | (D)-1" [7] | (F)-1" [2] | (E)-1" [2] | (S)-1" [4000] | (S)-2" [25] |
| Resist Composition 3-2 | (A)-1" [100] | (B)-1" [10] | (D)-2" [7] | (F)-1" [2] | (E)-1" [2] | (S)-1" [4000] | (S)-2" [25] |
| Resist Composition 3-3 | (A)-1" [100] | (B)-1" [10] | (D)-3" [7] | (F)-1" [2] | (E)-1" [2] | (S)-1" [4000] | (S)-2" [25] |
| Resist Composition 3-4 | (A)-1" [100] | (B)-1" [10] | (D)-4" [7] | (F)-1" [2] | (E)-1" [2] | (S)-1" [4000] | (S)-2" [25] |

TABLE 16-continued

| | Component (A) | Component (B) | Component (D) | Component (F) | Component (E) | Component (S) | |
|---|---|---|---|---|---|---|---|
| Resist Composition 3-5 | (A)-1" [100] | (B)-1" [10] | (D)-5" [7] | (F)-1" [2] | (E)-1" [2] | (S)-1" [4000] | (S)-2" [25] |
| Resist Composition 3-6 | (A)-1" [100] | (B)-1" [10] | (D)-6" [7] | (F)-1" [2] | (E)-1" [2] | (S)-1" [4000] | (S)-2" [25] |

In Table 16, the reference characters indicate the following. Further, the values in brackets [ ] indicate the amount (in terms of parts by weight) of the component added.

(A)-1": a polymeric compound (A)-1" shown below (Mw: 7300, Mw/Mn: 1.67, l/m/n/o=40/10/40/10 (molar ratio))
(B)-1": a compound (B)-1" shown below
(D)-1" to (D)-6": a compound (D)-1" to (D)-6" shown below
(F)-1": a polymeric compound (F)-1" shown below (l/m=20/80 (molar ratio), Mw: 23100, Mw/Mn: 1.78)
(E)-1": salicylic acid
(S)-1": a mixed solvent of PGMEA/PGME/cyclohexanone=45/30/25 (weight ratio)
(S)-2": γ-butyrolactone

[Chemical Formula 75]

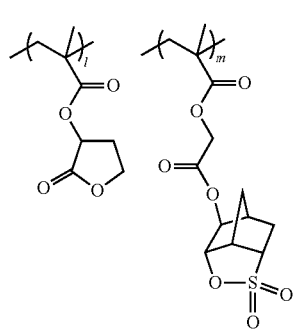

(A)-1"

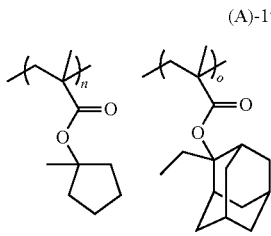

(B)-1"

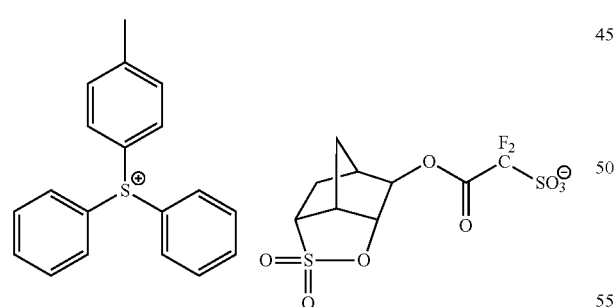

(D)-1"

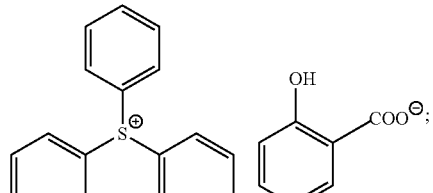

pKa = 3.01

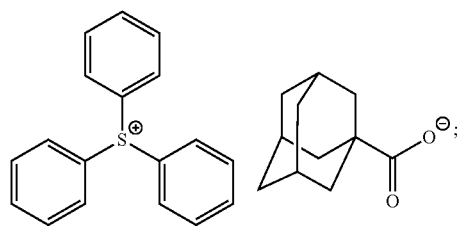

(D)-2"

pKa = 4.86

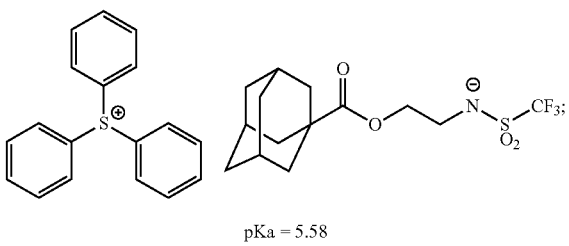

(D)-3"

pKa = 5.58

[Chemical Formula 76]

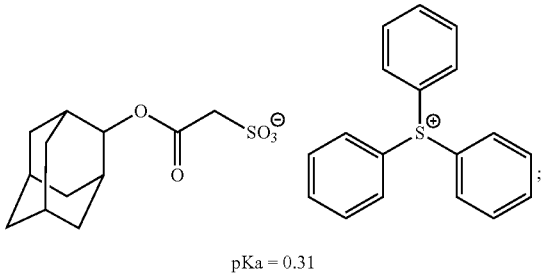

(D)-4"

pKa = 0.31

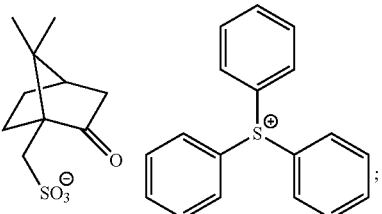

(D)-5"

pKa = 1.17

-continued (D)-6″

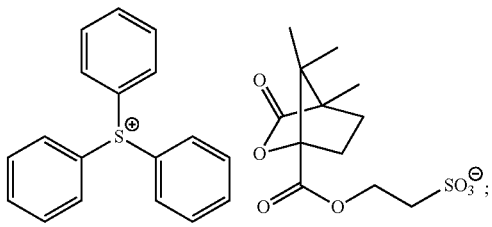

pKa = 1.44

(F)-1″

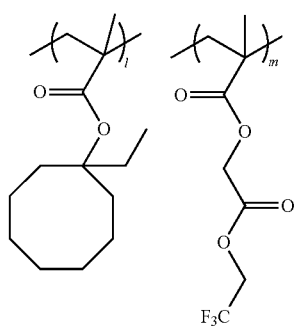

<Production of Solution Containing Acid>

100 parts by weight of a polymeric compound (AP)-1″ shown below (Mw: 3000), 40 parts by weight of a compound (T)-1″ shown below (pKa: −2.0 to −4.0), and 17000 parts by weight of a solvent (4-methyl-2-pentanol) were mixed together to obtain a solution containing an acid component.

[Chemical Formula 77]

(AP)-1″

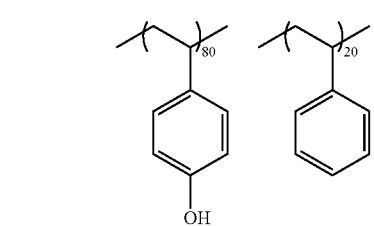

(T)-1″

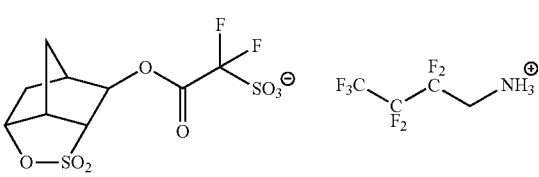

<Production of Solution Containing Acid Diffusion Control Agent>

100 parts by weight of a polymeric compound (BP)-1″ shown below (Mw: 15000), 20 parts by weight of trioc-tylamine and 10000 parts by weight of a solvent (isoamyl ether) were mixed together to obtain a solution containing an acid diffusion control agent.

[Chemical Formula 78]

(BP)-1″

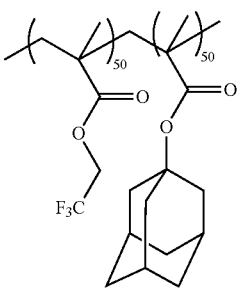

<Formation of Resist Pattern>

Using each of the produced resist compositions 3-1 to 3-6, a split pattern was formed according to the embodiment of the resist pattern forming method shown in FIG. 4.

In the method of forming a resist pattern of Examples 3-1 to 3-6, the positive resist compositions 1-6 were used, respectively. Among these Examples 3-1 to 3-6, Examples 3-1 to 3-3 were according to the present invention.

Step A

An organic anti-reflection film composition (product name: ARC29A, manufactured by Brewer Science Ltd.) was applied to an 12-inch silicon wafer using a spinner, and the composition was then baked at 205° C. for 60 seconds, thereby forming an organic anti-reflection film having a film thickness of 89 nm.

Then, each of the resist compositions 1 to 6 obtained above was applied to the organic anti-reflection film using a spinner, and was then prebaked (PAB) on a hotplate at 110° C. for 60 seconds and dried, thereby forming a resist film having a film thickness of 90 nm.

Subsequently, the resist film was selectively irradiated with an ArF excimer laser (193 nm) through a mask pattern (a binary mask; mask size: 59 nm), using an exposure apparatus NSR-S609B (manufactured by Nikon Corporation, NA=1.07, Dipole with POLANO).

Thereafter, alkali developing was conducted for 10 seconds at 23° C. in a 2.38% by weight aqueous solution of tetramethylammonium hydroxide (TMAH) (product name: NMD-3; manufactured by Tokyo Ohka Kogyo Co., Ltd.).

Further, a post exposure bake treatment (PEB) was conducted at 85° C. for 60 seconds.

As a result, a first resist pattern of a line and space pattern (hereafter, referred to as "LS pattern") having a pitch of 118 nm and a line width of 73 nm was formed.

Step B

The solution containing an acid obtained above was applied to the silicon wafer whereon the first resist pattern was formed in the [step A], using a spinner (1500 rpm) so as to cover the first resist pattern, thereby forming a structure composed of the first resist pattern and a first layer covering the first resist pattern.

Step B1

The solution containing an acid diffusion control agent was spin-coated so as to cover the structure obtained in [step B].

Step C

The structure coated with the solution containing an acid diffusion control in the [step B1] was baked at 110° C. for 60 seconds.

Step D

After the [step C], the structure conducted a bake treatment was subjected to an organic solvent developing treatment using butyl acetate for 13 seconds. As a result, a split pattern was formed.

With respect to the obtained split pattern, evaluations were performed as follows.

[Evaluation of Pattern Size]

With respect to the obtained split pattern, the each line width (nm) at 100 points in the split pattern was observed and measured from the upper side thereof using a measuring scanning electron microscope (SEM) (acceleration voltage: 300V; product name: S-9380, manufactured by Hitachi High-Technologies Corporation). The results are indicated "CD (nm)" in Table 17 below.

The term "line width" refers to a width of the organic solvent-insoluble region 1Pa" in the cross-sectional view of the pattern shown in FIG. 4(D).

[Evaluation of Pattern Height]

With respect to the obtained split pattern, the each line height (nm) was measured using a measuring scanning electron microscope (SEM) (acceleration voltage: 300V; product name: S-9380, manufactured by Hitachi High-Technologies Corporation). The results are indicated "Pattern Height (nm)" in Table 17 below.

The term "pattern height" refers to a height of the organic solvent-insoluble region 1Pa in the cross-sectional view of the pattern shown in FIG. 4(D).

[Evaluation of Line Width Roughness (LWR)]

With respect to the split patterns formed as above, 3σ was calculated as a yardstick of LWR.

"3σ" shows a value of 3 times the standard deviation σ (i.e., 3σ; unit: nm), which is calculated by measuring the line position at 400 points in the lengthwise direction of the top side view of the line pattern (the developing solution-insoluble region 1Pa" in the cross-sectional view of the pattern shown in FIG. 4(D)) using a scanning electron microscope (acceleration voltage: 800V; product name: S-9380; manufactured by Hitachi High-Technologies Corporation).

The smaller this 3σ value is, the lower the level of roughness of the line pattern side wall, indicating that a split pattern with a uniform width was obtained. The results are indicated "LWR (nm)" in Table 17.

TABLE 17

| | Resist Composition | CD (nm) | Pattern Height (nm) | LWR (nm) |
|---|---|---|---|---|
| Ex. 3-1 | Resist Composition 3-1 | 24.5 | 36.2 | 4.24 |
| Ex. 3-2 | Resist Composition 3-2 | 24.5 | 37.1 | 4.01 |
| Ex. 3-3 | Resist Composition 3-3 | 24.4 | 39.3 | 3.76 |
| Ex. 3-4 | Resist Composition 3-4 | 27.2 | 35.5 | 5.30 |
| Ex. 3-5 | Resist Composition 3-5 | 26.7 | 35.5 | 5.20 |
| Ex. 3-6 | Resist Composition 3-6 | 27.0 | 35.8 | 5.40 |

As shown in Table 17, the split patterns formed using the positive resist compositions of Examples 3-1 to 3-3 containing the acid diffusion control agent component containing an acid having an acid dissociation constant (pKa) of 3.0 or more exhibited fine pattern size, excellent pattern height and excellent LWR.

While preferred embodiments of the invention have been described and illustrated above, it should be understood that these are exemplary of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

EXPLANATION OF REFERENCES

1: substrate, 2: first resist pattern, 3: first layer, 4: solution consisted of a solvent, 2a: region exhibiting decreased solubility in an organic solvent, 2b: region exhibiting solubility in an organic solvent, 1': substrate, 1P': first resist pattern, 2': first layer, B1': layer, 1Pa': developing solution-insoluble region, 1Pb': region exhibiting solubility in an organic solvent, 3': pattern reversing film, 3P': third pattern, 1": substrate, 1P": first resist pattern, 2": first layer, 3": structure, B1": layer, 1Pa": organic developing solution-insoluble region, 1Pb": organic developing solution-soluble region

What is claimed is:
1. A method of forming a resist pattern, including:
applying a positive resist composition to a substrate to form a positive resist film, exposing the positive resist film and subjecting the positive resist film to an alkali development to form a first resist pattern;
applying a solution containing an acid or a thermoacid generator to the substrate on which the first resist pattern is formed, so as to cover the first resist pattern, to form a structure having the first resist pattern and a first layer covering the first resist pattern;
heating the structure to change the solubility of the first resist pattern in an organic solvent under action of the acid or under action of acid generated from the thermoacid generator; and
after the heating, developing the structure with the organic solvent to remove a region of the first resist pattern other than the region of the first resist pattern where the solubility in the organic solvent is changed, so as to form a second resist pattern.

2. The method of forming a resist pattern according to claim 1, including:
applying a positive resist composition to a substrate to form a positive resist film, exposing the positive resist film and subjecting the positive resist film to an alkali development to form a first resist pattern;
applying a solution containing an acid or a thermoacid generator to the substrate on which the first resist pattern is formed, so as to cover the first resist pattern, to form a structure having the first resist pattern and a first layer covering the first resist pattern;
applying a solution containing a solvent to cover the structure;
heating the structure to change the solubility of the first resist pattern in an organic solvent under action of the acid or under action of acid generated from the thermoacid generator; and
after the heating, developing the structure with the organic solvent to remove a region of the first resist pattern other than the region of the first resist pattern where the solubility in the organic solvent is changed, so as to form a second resist pattern.

3. The method of forming a resist pattern according to claim 2, wherein the solution containing a solvent further contains an acid diffusion control agent.

4. The method of forming a resist pattern according to claim 3, wherein the acid diffusion control agent contains a nitrogen-containing organic compound.

5. The method of forming a resist pattern according to claim 3, wherein the solution containing the acid diffusion control agent contains a structural unit (a4) having an acid non-dissociable cyclic group.

6. The method of forming a resist pattern according to claim 3, wherein the solution containing the acid diffusion control agent contains a low-polarity solvent.

7. The method of forming a resist pattern according to claim 1, including:
applying a positive resist composition to a substrate to form a positive resist film, exposing the positive resist film and subjecting the positive resist film to an alkali development to form a first resist pattern;
applying a solution containing an acid or a thermoacid generator to the substrate on which the first resist pattern is formed, so as to cover the first resist pattern, to form a structure having the first resist pattern and a first layer covering the first resist pattern;
heating the structure to change the solubility of the first resist pattern in an organic solvent under action of the acid or under action of acid generated from the thermoacid generator;
after the heating, developing the structure with the organic solvent to remove a region of the first resist pattern other than the region of the first resist pattern where the solubility in the organic solvent is changed, so as to form a second resist pattern; and
applying a pattern reversing composition containing an organic solvent that does not dissolve the second resist pattern to form a pattern reversing film, and subjecting the pattern reversing film to an alkali development using an alkali developing solution to remove the second resist pattern and conduct patterning of the pattern reversing film, so as to form a third pattern.

8. The method of forming a resist pattern according to claim 7, wherein the pattern reversing composition contains a resin component (A"1), and the resin component (A"1) comprises a structural unit having a silicon atom.

9. The method of forming a resist pattern according to claim 1, including:
applying a positive resist composition to a substrate to form a positive resist film, exposing the positive resist film and subjecting the positive resist film to an alkali development to form a first resist pattern;
applying a solution containing an acid or a thermoacid generator to the substrate on which the first resist pattern is formed, so as to cover the first resist pattern, to form a structure having the first resist pattern and a first layer covering the first resist pattern;
heating the structure to change the solubility of the first resist pattern in an organic solvent under action of the acid or under action of acid generated from the thermoacid generator; and
after the heating, developing the structure with the organic solvent to remove a region of the first resist pattern other than the region of the first resist pattern where the solubility in the organic solvent is changed, so as to form a second resist pattern as a split pattern, wherein the positive resist composition comprises an acid diffusion control agent, and
the acid diffusion control agent contains an acid having an acid dissociation constant (pKa) of 3.0 or more.

10. The method of forming a resist pattern according to claim 9, including:
applying a positive resist composition to a substrate to form a positive resist film, exposing the positive resist film, and subjecting the positive resist film to an alkali development to form a first resist pattern;
applying a solution containing an acid or a thermoacid generator to the substrate on which the first resist pattern is formed, so as to cover the first resist pattern, to form a structure having the first resist pattern and a first layer covering the first resist pattern;
applying a solution containing an acid diffusion control agent to cover the structure;
heating the structure to change the solubility of the first resist pattern in an organic solvent under action of the acid or under action of acid generated from the thermoacid generator; and
after the heating, developing the structure with the organic solvent to remove a region of the first resist pattern other than the region of the first resist pattern where the solubility in the organic solvent is changed, so as to form a second resist pattern as a split pattern.

11. The method of forming a resist pattern according to claim 9, wherein the acid diffusion control agent comprises a compound represented by any one of general formulae (d1-1) to (d1-3) shown below:

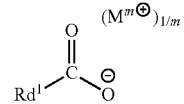

(d1-1)

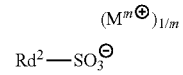

(d1-2)

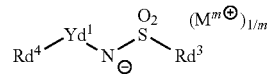

(d1-3)

wherein in the general formulae (d1-1) to (d1-3),
$Rd^1$ to $Rd^4$ each independently represents a cyclic group which may have a substituent, a chain-like alkyl group which may have a substituent or a chain-like alkenyl group which may have a substituent, provided that, the carbon atom adjacent to the sulfur atom within the $Rd^2$ in the formula (d1-2) does not have more than two fluorine atoms bonded thereto; $Yd^1$ represents a single bond or a divalent linking group; $M^{m+}$ each independently represents an organic cation having a valency of m; and m represents 1.

12. The method of forming a resist pattern according to claim 1, wherein the thermoacid generator comprises a compound represented by any one of general formulae (T1-1) to (T1-3) shown below:

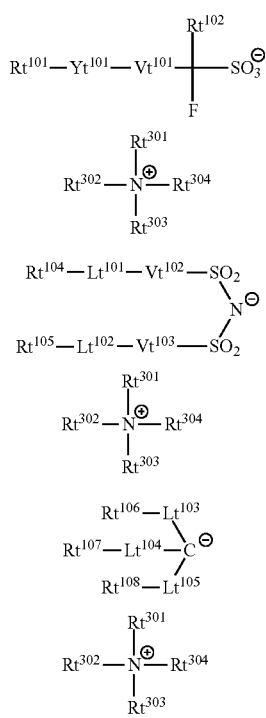

wherein $Rt^{101}$ and $Rt^{104}$ to $R^{108}$ each independently represents a cyclic group which may have a substituent, a chain-like alkyl group which may have a substituent, or a chain-like alkenyl group which may have a substituent; $Rt^{104}$ and $Rt^{105}$ may be mutually bonded to form a ring; $Rt^{106}$ and $Rt^{107}$ may be mutually bonded to form a ring; $Rt^{102}$ represents a fluorine atom or a fluorinated alkyl group having 1 to 5 carbon atoms; $Yt^{101}$ represents a single bond or a divalent linking group containing an oxygen atom; $Vt^{101}$ to $Vt^{103}$ each independently represents a single bond, an alkylene group or a fluorinated alkylene group; $Lt^{101}$ and $Lt^{102}$ each independently represents a single bond or an oxygen atom; $Lt^{103}$ to $Lt^{105}$ each independently represents a single bond, —CO—, or —SO$_2$—; $Rt^{301}$ to $Rt^{304}$ each independently represents a hydrogen atom or a linear, branched, or cyclic fluorinated alkyl group having 1 to 12 carbon atoms; and $Rt^{301}$ to $Rt^{303}$ may be bonded to each other to form a ring together with a nitrogen atom in the formula.

13. The method of forming a resist pattern according to claim 1, wherein the solution containing an acid or a thermoacid generator contains a structural unit (a3) having a polar group-containing aliphatic hydrocarbon group.

14. The method of forming a resist pattern according to claim 1, wherein the solution containing an acid or a thermoacid generator contains a linear or branched monohydric alcohol having 1 to 10 carbon atoms.

* * * * *